United States Patent
Walensky et al.

(10) Patent No.: US 10,822,374 B2
(45) Date of Patent: Nov. 3, 2020

(54) CANCER THERAPIES AND DIAGNOSTICS

(75) Inventors: Loren D. Walensky, Newton Center, MA (US); Federico Bernal, Gaithersburg, MD (US); Geoffrey Wahl, San Diego, CA (US); Mark Wade, Gorizia (IT)

(73) Assignees: Dana-Farber Cancer Institute, Inc., Boston, MA (US); Salk Institute for Biological Studies, San Diego, CA (US)

(*) Notice: Subject to any disclaimer, the term of this patent is extended or adjusted under 35 U.S.C. 154(b) by 363 days.

(21) Appl. No.: 13/884,709

(22) PCT Filed: Nov. 14, 2011

(86) PCT No.: PCT/US2011/060647
§ 371 (c)(1),
(2), (4) Date: Sep. 20, 2013

(87) PCT Pub. No.: WO2012/065181
PCT Pub. Date: May 18, 2012

(65) Prior Publication Data
US 2014/0018302 A1    Jan. 16, 2014

Related U.S. Application Data

(60) Provisional application No. 61/413,199, filed on Nov. 12, 2010.

(51) Int. Cl.
C07K 4/12 (2006.01)
A61K 38/17 (2006.01)

(52) U.S. Cl.
CPC ........... *C07K 4/12* (2013.01); *A61K 38/1709* (2013.01)

(58) Field of Classification Search
CPC .......................... C07K 4/12; A61K 38/1709
See application file for complete search history.

(56) References Cited

U.S. PATENT DOCUMENTS

| | | | |
|---|---|---|---|
| 7,611,870 B2 | 11/2009 | Feinberg | |
| 7,723,468 B2 | 5/2010 | Daffre et al. | |
| 8,889,632 B2 | 11/2014 | Bernal et al. | |
| 9,527,896 B2 | 12/2016 | Bernal et al. | |
| 10,202,431 B2 | 2/2019 | Bernal et al. | |
| 2005/0250689 A1 | 11/2005 | Brooks et al. | |
| 2006/0008848 A1 | 1/2006 | Verdine et al. | |
| 2008/0262200 A1 | 10/2008 | Nash | |
| 2008/0280769 A1 | 11/2008 | Doemling | |
| 2009/0047711 A1 | 2/2009 | Nash | |
| 2009/0069334 A1 | 3/2009 | Rebek, Jr. et al. | |
| 2009/0088533 A1 | 4/2009 | Ameduri et al. | |
| 2009/0275519 A1 | 11/2009 | Nash et al. | |
| 2009/0326192 A1 | 12/2009 | Nash et al. | |
| 2010/0022549 A1 | 1/2010 | Rebek, Jr. et al. | |
| 2010/0075949 A1 | 3/2010 | Burdack et al. | |
| 2010/0113466 A1 | 5/2010 | Rebek, Jr. et al. | |
| 2010/0168388 A1 | 7/2010 | Bernal et al. | |
| 2010/0184628 A1 | 7/2010 | Nash | |
| 2010/0216688 A1 | 8/2010 | Nash et al. | |
| 2011/0318352 A1 | 12/2011 | Walensky | |

FOREIGN PATENT DOCUMENTS

| | | | |
|---|---|---|---|
| WO | WO 1999/14259 | 3/1999 | |
| WO | WO 1999/34833 | 7/1999 | |
| WO | WO 2005/044839 | 5/2005 | |
| WO | WO 2008/095063 | * 8/2008 | ............... C07K 7/54 |
| WO | WO08/106507 | 9/2008 | |
| WO | WO 2008/121767 A2 | 10/2008 | |
| WO | WO 2008121767 | 10/2008 | |
| WO | WO 2009/108261 | 9/2009 | |
| WO | WO 2009/126292 A2 | 10/2009 | |
| WO | WO 2010/068684 | 6/2010 | |
| WO | WO 2010/148335 | 12/2010 | |

OTHER PUBLICATIONS

Reed et al. (Journal of Biological Chemistry, 285(14): 10786-10796, Apr. 2010).*
Tsuganezawa et al. (Journal of Biomolecular Screening, 18: 191-198, 2013).*
Berberich et al. (Cell Cycle, 9(18): 3640-3641, 2010).*
Stancovski et al. (PNAS, 88: 8691-8695, 1991).*
Jiang et al. (J. Biol. Chem., 280: 4656-4662, 2005).*
Bernal et al., *A Stapled p53 Helix Targets HDMX to Overcome Nutlin-3 Resistance and Reactivate the p53 Tumor Suppressor Pathway in Cancer*, Blood, 112(11):915 (Nov. 2008).
Patton, *Levels of HdmX Expression Dictate the Sensitivity of Normal and Transformed Cells to Nutlin-3*, Cancer Research, 66(6):3169-3176 (Mar. 2006).
EPO Communication and Search Report, EP Application No. 11840559.6-1456 / 2637680, dated Jun. 13, 2014.
International Search Report and Written Opinion dated Jul. 10, 2012 from corresponding application PCT/US2011060647.
Reed, et al. Identification and characterization of the first small molecule inhibitor of MDMX. J Biol Chem. Apr. 2010, 285(14):10786-96; Abstract, p. 10787, col. 2, Fig. 1B.
Bernal, et al. Therapeutic reactivation of p53 through dual targeting of HDM2 and HDMX with a stapled p53 peptide. Molecular Cancer Therapeutics 2009, 8(12S):Abstract C174.
Hu, et al. Efficient p53 activation and apoptosis by simultaneous disruption of binding to MDM2 and MDMX. Cancer Res. 2007, 67(18):8810-8817.
Bernal, et al. A stapled p53 helix overcomes HDMX-mediated suppression of p53. Cancer Cell. Nov. 16, 2010, 18(5):411-422.
Bernal, et al. Reactivation of the p53 Tumor Suppressor Pathway by a Stapled p53 Peptide. J Am Chem Soc. 2007, 129(9);2456-7.
Toledo, et al. MDM2 and MDM4: p53 regulators as targets in anticancer therapy. Int J Biochem Cell Biol. 2007, 39(7-8):1476-82.
Anderson et al. *MDM2 RNA binding is blocked by novel monoclonal antibody h-MDM2-F4-14*, Int J. Oncol, 31(3):545-555 (2007).

(Continued)

*Primary Examiner* — Nelson B Moseley, II
(74) *Attorney, Agent, or Firm* — Fish & Richardson P.C.

(57) ABSTRACT

Compositions and methods for increasing p53-dependent transcriptional activity in a cell.

29 Claims, 25 Drawing Sheets
Specification includes a Sequence Listing.

(56) References Cited

OTHER PUBLICATIONS

Arya et al., *Nutlin-3, the small-molecule inhibitor of MDM2, promotes senescence and radiosensitises laryngeal carcinoma cells harbouring wild-type p53*, British J. Cancer, 103(2):186-195 (2010).
Baker et al., *Chromosome 17 deletions and p53 gene mutations in colorectal carcinomas*, Science, 244(4901):217-221 (1989).
Bang, et al., *Total chemical synthesis of crambin*, J. Am. Chem Soc. 126(5):1377-1383 (2004).
Bartel et al., *Significance of HDMX-S (or MDM4) mRNA splice variant overexpression and HDMX gene amplification on primary soft tissue sarcoma prognosis*, Int. J. Cancer, 117(3):469-475 (2005).
Bird et al., *Hydrocarbon double-stapling remedies the proteolytic instability of a lengthy peptide therapeutic* PNAS USA, 107(32):14093-14098, (2010).
Bird et. al., *Synthesis and biophysical characterization of stabilized alpha-helices of BCL-2 domains*, Methods in Enzyrnol., 446:369-386 (2008).
Blackwell et al., *Ring-closing metathesis of olefinic peptides: design, synthesis, and structural characterization of macrocyclic helical peptides*, J. Org. Chem., 66(16): 5291-5302, (2001).
Bottger et al., *Molecular characterization of the hdm2-p53 interaction*, J. Mol. Biol., 269(5):744-756 (1997).
Broglia et al., *Design of HIV-1-PR inhibitors that do not create resistance: blocking the folding of single monomers*, Protein Sci., 14(10):2668-81 (2005).
Brown et al., *Awakening guardian angels: drugging the p53 pathway*, Nat. Rev. Cancer, 9(12):862-873 (2009).
Bunz et al., *Disruption of p53 in human cancer cells alters the responses to therapeutic agents*, J. Clin. Invest., 104(3):263-269 (1999).
Danovi et al., *Amplification of Mdmx (or Mdm4) directly contributes to tumor formation by inhibiting p53 tumor suppressor activity*, Mol. Cell. Biol., 24(130:5835-5843 (2004).
Ding et al. *Structure-based design of potent non-peptide MDM2 inhibitors*, J. Am. Chem. Soc. 127(29): 10130-10131 (2005).
Drakos et al., *Inhibition of p53-murine double minute 2 interaction by nutlin-3A stabilizes p53 and induces cell cycle arrest and apoptosis in Hodgkin lymphoma*, Clin. Cancer Res., 13(11):3380-3387 (2007).
Grasberger et al. *Discovery and cocrystal structure of benzodiazepinedione HDM2 antagonists that activate p53 in cells*, J. Med. Chem. 48(4):909-912 (2005).
Hammond et al., *An Examination of Binding Motifs Associated With Inter-Particle Interactions between Facetted Nano-Crystals of Acetylsalicylic Acid and Ascorbic Acid through the Application of Molecular Grid-Based Search Methods*, J. Pharm. Sci., 98(1):4589-603, (2009).
Harker et al., *Beta-peptides with improved affinity for hDM2 and hDMX*, Bioorg. Med. Chem., 17(5):2038-2046 (2009).
Hayashi et al., *N-acylpolyamine inhibitors of HDM2 and HDMX binding to p53*, Bioorg. Med. Chem., 17(23):7884-7893 (2009).
Honda et al., *Oncoprotein MDM2 is a ubiquitin ligase E3 for tumor suppressor p53*, FEBS Lett., 420(1):25-27 (1997).
Hu et al., *MDMX overexpression prevents p53 activation by the MDM2 inhibitor Nutlin*, Cancer Res., J. Biol. Chem., 281(44):33030-33035 (2006).
Joseph et al., *Stapled peptides in the p53 pathway: computer simulations reveal novel interactions of the staples with the target protein*, Cell Cycle, 9(22):4560-4568 (2010).
Kallen et al., *Crystal Structures of Human MdmX (HdmX) in Complex with p53 Peptide Analogues Reveal Surprising Conformational Changes*, J. Biol. Chem., 284(13):8812-8821 (2009).
Kapust et al., *Tobacco etch virus protease: mechanism of autolysis and rational design of stable mutants with wild-type catalytic proficiency*, Protein Eng., 14(12):993-1000 (2001).
Kirsch et al., *p53 controls radiation-induced gastrointestinal syndrome in mice independent of apoptosis*, Science, 327(5965):593-596 (2010).

Koblish et al., *Benzodiazepinedione inhibitors of the Hdm2:p53 complex suppress human tumor cell proliferation in vitro and sensitize tumors to doxorubicin in vivo*, Mol. Cancer Ther., 5(1):160-169 (2006).
Kritzer et al. *Miniature protein inhibitors of the p53-hDM2 interaction*, Chem Bio Chem, 7(1):29-31 (2006).
Kritzer et al., *Helical beta peptide inhibitors of the p53-hDM2 interaction*, J. Am. Chem. Soc., 126(31):9468-9469 (2004).
Kussie et al. *Structure of the MDM2 oncoprotein bound to the p53 tumor suppressor transactivation domain*, Science, 274(5289):948-953 (1996).
Lane, *p53, guardian of the genome*, Nature, 358(6381):15-16 (1992).
Lau et al., *HDM2 antagonist Nutlin-3 disrupts p73-HDM2 binding and enhances p73 function*, Oncogene 27:997-1003 (2008).
Laurie et al. *Inactivation of the p53 pathway in retinoblastoma*, Nature, 444(7115):61-66 (2006).
Li et al., *Turning a scorpion toxin into an antitumor miniprotein*, J. Am. Chem. Soc., 130(41):13546-13548 (2008).
Li et al., *Identification of high quality cancer prognostic markers and metastasis network modules* Nature, 1:34 1-10 (2010).
Livak and Schmittgen, *Analysis of relative gene expression data using real-time quantitative PCR and the 2(-Delta Delta C(T)) Method*, Methods, 25(4):402-408 (2001).
Marine and Dyer, *MDMX: from bench to bedside*, J. Cell. Sci., 120(Pt3):371-378 (2007).
Michel et al., *In Silico Improvement of beta3-peptide inhibitors of p53 x hDM2 and p53 x hDMX*, J. Am. Chem. Soc., 131(18):6356-6357 (2009).
Moll et al., *Wild-type p53 protein undergoes cytoplasmic sequestration in undifferentiated neuroblastomas but not in differentiated tumors*, Proc. Natl. Acad. Sci. U.S.A., 92(10):4407-4411 (1995).
Momand et al., *The mdm-2 oncogene product forms a complex with the p53 protein and inhibits p53-mediated fransactivation*, Cell, 69(7):1237-1245 (1992).
Ng and Yang, *Revealing the way of self-complementary dimerization for a shape-persistent macrocycle using density functional theory calculations*, J. Phys. Chem. B., 111(50):13886-93, (2007).
Pazgier et al., *Structural basis for high-affinity peptide inhibition of p53 interactions with MDM2 and MDMX*, PNAS, 106(12):4665-4670 (2009).
Phan et al., *Structure-based design of high affinity peptides inhibiting the interaction of p53 with MDM2 and MDMX*, J. Biol. Chem., 285(3):2174-2183 (2010).
Pichiorri, et al *Downregulation of p53-inducible microRNAs 192, 194, and 215 impairs the p53/MDM2 autoregulatory loop in multiple myeloma development*, Cancer Cell, 18(4):367-381 (2010).
Pitter et al., *Dissection of the BCL-2 family signaling network with stabilized alpha-helices of BCL-2 domains*, Methods Enzymol., 446:387-408 (2008).
Ramos et al., *Aberrant expression of HDMX proteins in tumor cells correlates with wild-type p53*, Cancer Res., 61(5):1839-1842 (2001).
Schafmeister et al., *An All-Hydrocarbon Cross-Linking System for Enhancing the Helicity and Metabolic Stability of Peptides*, J. Am. Chem. Soc., 122:5891-5892 (2000).
Shangary et al., *Temporal activation of p53 by a specific MDM2 inhibitor is selectively toxic to tumors and leads to complete tumor growth inhibition*, Proc. Natl. Acad. Sci., U.S.A., 105(10):3933-3938 (2008).
Shangary et al., *Small-Molecule Inhibitors of the MDM2-p53 Protein-Protein Interaction to Reactivate p53 Function: A Novel Approach for Cancer Therapy*, Ann Rev Pharmacol Toxicol., 49:223-241 (2009).
Shaulian et al., *Identification of a minimal transforming domain of p53: negative dominance through abrogation of sequence-specific DNA binding*, Mol. Cell. Biol., 12(12):5581-5592 (1992).
Shvarts et al., *Isolation and identification of the human homolog of a new p53-binding protein, Mdmx*, Genomics, 43(1):34-42 (1997).
Stad et al., *Hdmx Stabilizes Mdm2 and p53*, J. Biol. Chem., 275(36):28039-28044 (Sep. 2000).
Stewart et al, *The MCL-1 BH3 helix is an exclusive MCL-1 inhibitor and apoptosis sensitizer*, Nature Chem. Biol., 6(8):595-601 (2010).
Tabe et al., *MDM2 antagonist nutlin-3 displays antiproliferative and proapoptotic activity in mantle cell lymphoma*, Clin. Cancer Res., 15(3):933-942 15 (2009).

(56) References Cited

OTHER PUBLICATIONS

Toledo and Wahl, *Regulating the p53 pathway: in vitro hypotheses, in vivo veritas*, Nat. Rev. Cancer, 6(12):909-923 (2006).
Vassilev et al., *In vivo activation of the p53 pathway by small-molecule antagonists of MDM2*, Science, 303(5659):844-848 (2004).
Vogelstein et al., *Surfing the p53 network*, Nature, 408(6810):307-310 (2000).
Wade et al., *BH3 activation blocks Hdmx suppression of apoptosis and cooperates with Nutlin to induce cell death*, Cell Cycle, 7(13):1973-1982 (2008).
Wade et al., *Hdmx modulates the outcome of p53 activation in human tumor cells*, J. Biol. Chem., 281(44):33036-33044 (2006).
Walensky et al., *A stapled BID BH3 helix directly binds and activates BAX*, Mol. Cell., 24:199-210 (2006).
Walensky et al., *Activation of apoptosis in vivo by a hydrocarbon-stapled BH3 helix*, Science, 305(5689):1466-1470 (2004).
Wang et al., *Quantitative analyses reveal the importance of regulated Hdmx degradation for p53 activation*, Proc. Natl. Acad. Sci. U.S.A., 104(30):12365-12370 25 (2007).
Williams et al. *Asymmetric Synthesis of Monosubstituted and α,α-Disubstituted α-Amino Acids via Diastereoselective Glycine Enolate Alkylations*, J. Am. Chem. Soc., 113:9276-9286 (1991).
Yang et al., *Calculation of Protein Conformation from Circular Dichroism*, Methods Enzymol. 130:208-269 (1986).
Yin et al., *Terphenyl-based helical mimetics that disrupt the p53/HDM2 interaction*, Angew. Chem. Int. Ed. Engl., 44(18):2704-2707 (2005).
International Preliminary Report on Patentability in International Appln. No. PCT/US2008/052580, dated Aug. 4, 2009, 7 pages.
International Search Report and Written Opinion in International Appln. PCT/US2008/052580, dated May 16, 2008, 2 pages.
Joerger et al., "The Tumor Suppressor p53: From Structures to Drug Discovery," Cold Spring Harb Perspect Biol, 2010, 2(6):a000919.
Li et al., "Systematic Mutational Analysis of Peptide Inhibition of the p53-MDM2/MDMX Interactions," J Mol Biol., 2010, 398(2):200-213.

\* cited by examiner

WT p53₁₄₋₂₉  Ac-LSQETF$DLWKLLPEN-NH₂
SAH-p53-8   Ac-QSQQTF*NLWRLL*QN-NH₂
SAH-p53-8_F19A  Ac-QSQQTA*NLWRLL*QN-NH₂

| Compound | Sequence * = R₅ / + = S₅ | Charge (@ pH 7.4) | α helicity (%) | K_D (nM) | Cell permeable | Cell death |
|---|---|---|---|---|---|---|
| WT | Ac- LSQETFSDLWKLLPENNH₂ LSQETFSDLWKLLPEN | -2 | 11 | 410 19 | NO | - |
| SAH-p53-1 | Ac- LSQETFSD*WKLLPE+NH₂ | -2 | 25 | 100 8 | NO | - |
| SAH-p53-2 | Ac- LSQE*FSDLWK+LPENNH₂ | -2 | 10 | 400 50 | NO | - |
| SAH-p53-3 | Ac- LSQ*TFSDLW+LLPENNH₂ | -2 | 12 | 1200 60 | NO | - |
| SAH-p53-4 | Ac- LSQETF*DLWKLL+ENNH₂ | -2 | 59 | 0.92 0.11 | NO | - |
| SAH-p53-5 | Ac- LSQETF*NLVVKLL+QNNH₂ | 0 | 20 | 0.80 0.05 | YES | - |
| SAH-p53-6 | Ac- LSQQTF*NLWRLL+QNNH₂ | +1 | 14 | 56 11 | YES | - |
| SAH-p53-7 | Ac- QSQQTF*NLWKLL+QNNH₂ | +1 | 36 | 50 10 | YES | - |
| SAH-p53-8 | Ac- QSQQTF*NLWRLL+QNNH₂ QSQQTF*NLWRLL+QN | +1 | 85 | 55 11 | YES | + |
| SAH-p53-8S_A | QS*QTF*NLWRLL+QN | | | | | |
| SAH-p53-8S_B | QS*QTF*NLW*LLPQN | | | | | |
| SAH-p53-8F19A | Ac- QSQQTA*NLWRLL+QNNH₂ | +1 | 39 | >4000 | YES | - |
| UAH-p53-8 | Ac- QSQQTF*NLWRKK+QNNH₂ | +1 | 36 | 100 10 | YES | - |
| SAH-p53-9 | LSQAAF*ALWALL*AN | | | | | |
| SAH-p53-10 | QTF*NLWRLL* | | | | | |
| SAH-p53-11 | QTF*DLWRLL* | | | | | |

FIG. 1C

| Compound | Sequence<br>* = $R_8$/ + = $S_5$ | Charge<br>(@ pH 7.4) | α helicity<br>(%) | $K_d$<br>(nM) | Cell<br>permeable | Cell<br>death |
|---|---|---|---|---|---|---|
| SAH-p53-12 | *TFS*LWKLL | | | | | |
| SAH-p53-13 | ETF*DLW*LL | | | | | |
| SAH-p53-14 | QTF*NLW*LL | | | | | |
| SAH-p53-15 | *SQE*FSNLWKLL | | | | | |

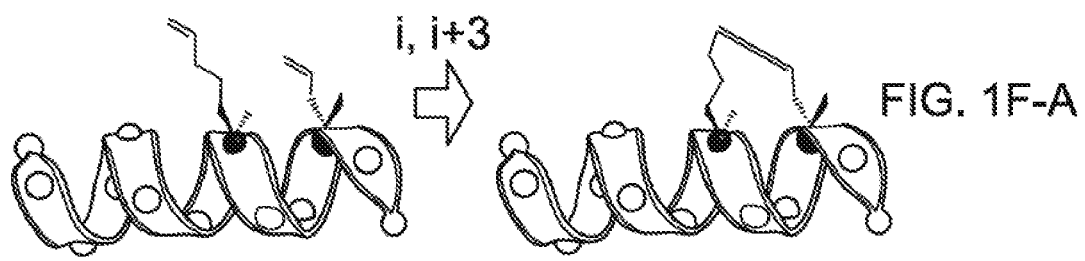
FIG. 1F-A
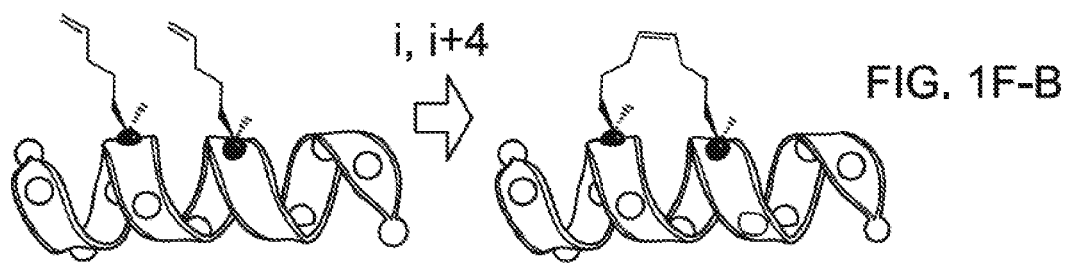
FIG. 1F-B
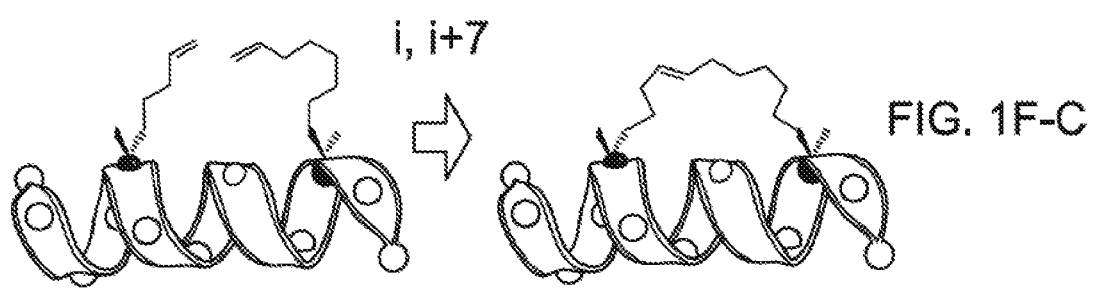
FIG. 1F-C
FIG. 1F-D

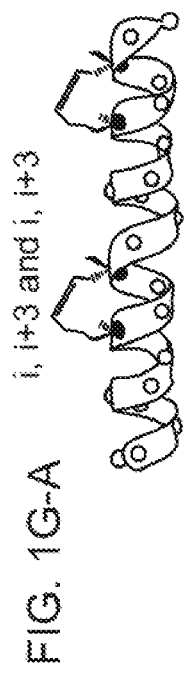
FIG. 1G-A i, i+3 and i, i+3
FIG. 1G-B i, i+4 and i, i+4
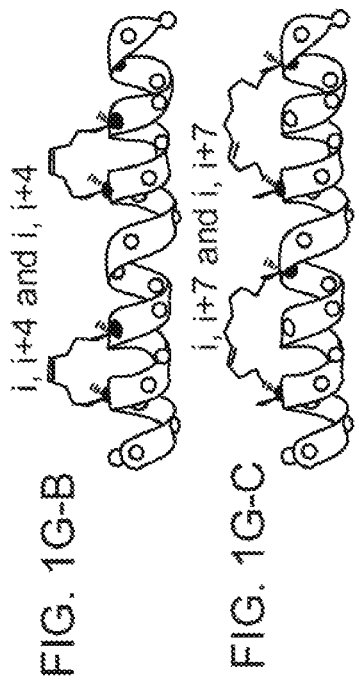
FIG. 1G-C i, i+7 and i, i+7
FIG. 1G-D i, i+3 and i, i+4
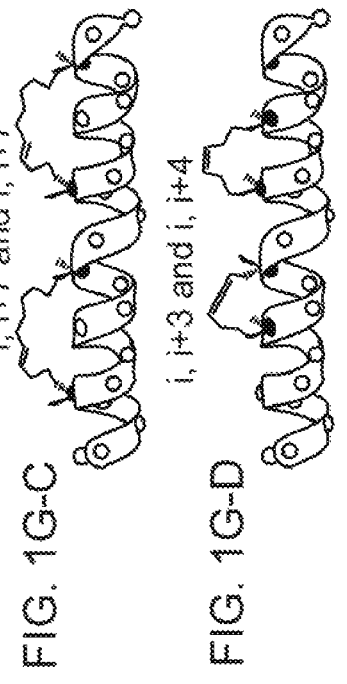
FIG. 1G-E i, i+4 and i, i+7
FIG. 1G-F i, i+4 and i, i+4
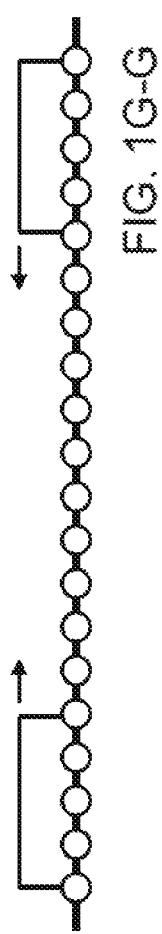
FIG. 1G-G
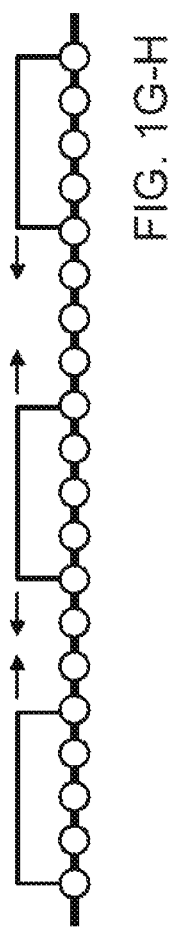
FIG. 1G-H HDM2i-Sensitive (Low cellular p53)

HDM2i-Resistant (Low cellular p53)

HDMXi-Sensitive (High cellular p53)

HDMXi-Resistent (Low cellular p53)

Synergy to Overcome Resistance (Low cellular p53)

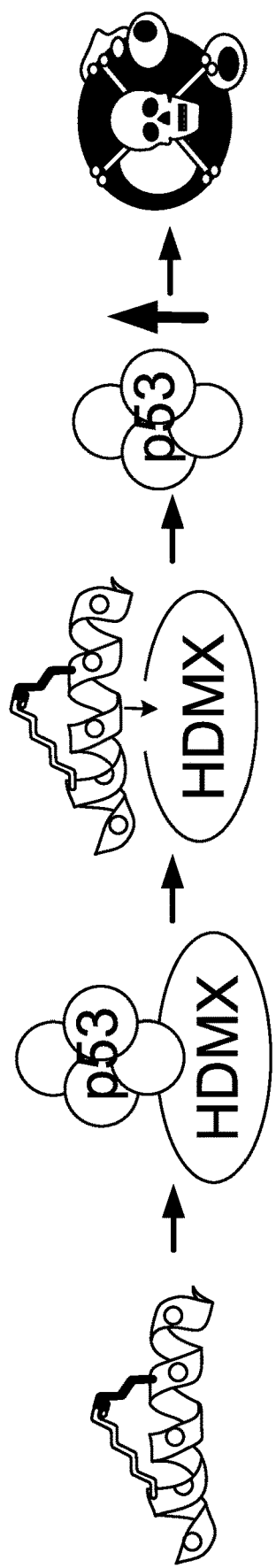

FIG. 12

```
1   meepqsdpsv epplsqetfs dlwkllpenn vlsplpsqam ddlmlspddi eqwftedpgp
61  deaprmpeaa prvapapaap tpaapapaps wplsssvpsq ktyqgsygfr lgflhsgtak
121 svtctyspal nkmfcqlakt cpvqlwvdst pppgtrvram aiykqsqhmt evvrrcphhe
181 rcsdsdglap pqhlirvegn lrveylddrn tfrhsvvvpy eppevgsdct tihynymcns
241 scmggmnrrp iltiitleds sgnllgrnsf evrvcacpgr drrteeenlr kkgephhelp
301 pgstkralpn ntssspqpkk kpldgeyftl qirgrerfem frelnealel kdaqagkepg
361 gsrahsshlk skkgqstsrh kklmfktegp dsd (SEQ ID NO:1)
```

FIG. 13

CANCER THERAPIES AND DIAGNOSTICS

RELATED APPLICATIONS

This application is a 371 US National Phase of PCT/US2011/060647, filed Nov. 14, 2011, which claims benefit of U.S. Provisional Application No. 61/413,199 filed Nov. 12, 2010, the entire content of which application is hereby expressly incorporated by reference herein in its entirety.

FEDERALLY SPONSORED RESEARCH OR DEVELOPMENT

This invention was made with government support under grant numbers K22 CA128886 and P01 CA092625 awarded by The National Institutes of Health. The government has certain rights in the invention.

TECHNICAL FIELD

The present disclosure relates to compositions and methods for cancer therapy and diagnostics.

BACKGROUND

As the "guardian of the genome," p53 prevents the emergence of genetically variant clones by activating defense mechanisms, such as induction of senescent-like arrest and apoptotic programs, to prevent replication of defective cells (Lane, Nature, 358:15-16 (1992); Vogelstein et al., Nature, 408:307-310 (2000)). Cancer cells have adopted a number molecular strategies to subvert p53 activity and achieve a pathologic survival advantage (see, e.g., Baker et al., Science, 244:217-221 (1989); Honda et al., FEBS Lett., 420:25-27 (1997); Momand et al., Cell, 69:1237-1245 (1992); Moll et al., Proc. Natl. Acad. Sci. U.S.A., 92:4407-4411 (1995).

Restoration of p53 activity is a strategy for cancer therapy (see, e.g., Brown et al., Nat. Rev. Cancer, 9:862-873 (2009)). The determination of the crystal structure of the p53-HDM2 binding interface contributed to the development of such strategies, e.g., by revealing that a hydrophobic cleft on the N-terminal surface of the E3 ubiquitin ligase HDM2 (Toledo and Wahl, Nat. Rev. Cancer, 6:909-923 (2006); Marine and Dyer, J. Cell. Sci., 120:371-378 (2007); Bartel et al., Int. J. Cancer, 117:469-475 (2005); Shvarts et al., Genomics, 43:34-42 (1997); Danovi et al., Mol. Cell. Biol., 24:5835-5843 (2004)) directly engages the amphipathic α-helix of the p53 transactivation domain (Kussie et al., Science, 274:948-953 (1996)). Consequently, small molecules and peptides that target the p53-binding pocket of HDM2 have been developed (see, e.g., Bernal et al., J. Am. Chem. Soc., 129:2456-2457 (2007); Grasberger et al., J. Med. Chem., 48:909-912 (2005); Koblish et al., Mol. Cancer. Ther., 5:160-169 (2006); Kritzer et al., J. Am. Chem. Soc., 126: 9468-9469 (2004); Shangary et al., Proc. Natl. Acad. Sci., U.S.A., 105:3933-3938 (2008); Vassilev et al., Science, 303:844-848 (2004); Yin et al., Angew. Chem. Int. Ed. Engl., 44:2704-2707 (2005)). One such agent is the small molecule MDM2 inhibitor, Nutlin-3 (Vassilev et al., Science, 303: 844-848 (2004)). It has been shown using these agents that targeting HDM2 in certain tumors that express p53 (e.g., wild-type p53) can lead to a therapeutic surge in p53 levels. Specifically, it has been shown that Nutlin-3 can trigger apoptosis in the absence of other therapeutics in certain tumors (see, e.g., Drakos et al., Clin. Cancer Res., 13:3380-3387 (2007); Tabe et al., Clin. Cancer Res., 15:933-942 (2009)). However, such effects do not occur in all tumors types. Specifically, certain tumors are resistant or more resistant than others to HDM2-targeting therapeutics. Co-expression of the E3 ubiquitin ligase HDMX with HDM2 can reduce the efficacy of HDM2 targeting agents (see, e.g., Hu et al., Cancer Res., J. Biol. Chem., 281:33030-33035 (2006); Patton et al., Cancer Res., 66:3169-3176 (2006); Wade et al., J. Biol. Chem., 281:33036-33044 (2006)).

The role of HDMX in regulating p53 dynamics has been described (see, e.g., Danovi et al., Mol. Cell. Biol., 24:5835-5843 (2004); Laurie et al., Nature, 444:61-66 (2006); Ramos et al., Cancer Res., 61:1839-1842 (2001); Wade et al., J. Biol. Chem., 281:33036-33044 (2006); Wang et al., Proc. Natl. Acad. Sci. U.S.A., 104:12365-12370 (2007)) and in vitro preliminary reports are available for several agents that target HDMX (see, e.g., Harker et al., Bioorg. Med. Chem., 17:2038-2046 (2009); Hayashi et al., Bioorg. Med. Chem., 17:7884-7893 (2009); Hu et al., Cancer Res., 67:8810-8817 (2007); Kallen et al., J. Biol. Chem., 284:8812-8821 (2009); Li et al., J. Am. Chem. Soc., 130:13546-13548 (2008); Michel et al., J. Am. Chem. Soc., 131:6356-6357 (2009); Pazgier et al., Proc. Natl. Acad. Sci. U.S.A., 106:4665-4670 (2009); Reed et al., J. Biol. Chem., 285:10786-10796 (2010)).

Cancer remains one of the leading causes of morbidity and mortality in the United States. Improved cancer therapies are required.

SUMMARY

The present disclosure provides compositions and methods for the diagnosis, prognosis, and/or treatment of cancer in a subject.

In some aspects, the disclosure provides methods for increasing p53 activity in a cell. Such methods can include, obtaining or providing a cell that encodes or expresses p53 (e.g., functional p53), determining whether HDMX is expressed in the cell, and, if HDMX is expressed, contacting the cell with a HDMX modulating agent, thereby increasing p53 activity in the cell. In some embodiments, HDMX modulating agents include peptides (e.g., non-cross-linked and cross-linked peptides) having identity to the transactivation domain of p53. In some instances, peptides can have a first level of identity to the p53 transactivation domain for amino acids that correspond to amino acids present in the interacting face of the p53 transactivation domain, and a second level of identity to the p53 transactivation domain for all other amino acids (e.g., those outside the interacting face). For example, amino acids in the peptide corresponding to those on the interacting face of the p53 transactivation domain can be conserved or can be conservative substitutions of amino acids in the interacting face of the p53 transactivation domain, and amino acids outside those in the interacting face can have at least or about 30%, at least or about 40%, at least or about 50%, at least or about 60%, at least or about 70%, at least or about 80%, at least or about 90%, at least or about 95%, at least or about 98%, at least or about 99%, or 100% identity to those amino acids outside the interacting face of the peptide. In some aspects, peptides can be crosslinked by one or more internal crosslinkers. In some embodiments, p53 is human p53. In some embodiments, the HDMX modulating agent can be a cross-linked peptide shown in FIG. 1C. In some embodiments, the HDMX modulating agent can be SAH-p53-8 shown in FIG. 1C.

The methods disclosed above can also further include contacting the cell with one or more HDM2 modulating agents. Exemplary HDM2 modulating agents can include Nutlin-3 (e.g., Nutlin-3a), including analogues, modifications, improvements, and derivatives thereof.

In some embodiments, the step of determining whether HDMX is expressed can include detecting the presence of a HDMX and/or a p53-HDMX complex. The methods can also optionally further include determining whether HDM2 is expressed in the cell, and if HDM2 is expressed, contacting the cell with a HDM2 modulating agent (e.g., Nutlin-3). In some embodiments, doses of HDMX modulating agents and HDM2 modulating agents administered to a cell or subject are synergistic or additive. In some embodiments, the cells are in vitro. Alternatively or in addition, the cells can be in a subject (e.g., a subject with cancer).

In another aspect, the present disclosure provides methods for increasing p53 activity in a cell that include obtaining or providing a cell in which p53 activity is not substantially increased upon treatment with a HDM2 modulating agent (e.g., Nutlin-3); and contacting the cell with a HDMX modulating agent, thereby increasing p53 activity in the cell. In some embodiments, HDMX modulating agents can include peptides described herein. In some embodiments, p53 is human p53. In some embodiments, the HDMX modulating agent can be a cross-linked peptide shown in FIG. 1C. In some embodiments, the HDMX modulating agent can be SAH-p53-8. The methods can also, optionally, include contacting the cell with a HDM2 modulating agent (e.g., Nutlin-3). In some embodiments, the cells or subjects can be contacted (e.g., treated) with doses of the HDMX modulating agent and the HDM2 modulating agent that are either synergistic or additive.

In a further aspect, the present disclosure provides methods for increasing p53 activity in a cell that include obtaining or providing a cell that encodes (e.g., genetically encodes) or expresses p53 (e.g., functional p53), contacting the cell with a HDMX modulating agent and an HDM2 modulating agent, wherein the HDM2 modulating agent is not a stapled peptide shown in FIG. 1C, thereby increasing p53 activity in the cell. In some embodiments, HDMX modulating agents can include peptides described herein. In some aspects, p53 is human p53. In some embodiments, the HDMX modulating agent can be a cross-linked peptide shown in FIG. 1C. In some embodiments, the HDMX modulating agent can be SAH-p53-8. In some embodiments, the HDM2 modulating agent can be Nutlin-3. In some embodiments, the dose of the HDMX modulating agent and the HDM2 modulating agent is a synergistic dose or an additive dose. In some instances, the cell is in vitro. Alternatively, in some instances, the cell is in a subject (e.g., a subject that has cancer).

In some aspects, the present disclosure includes methods for treating cancer in a subject. These methods can include detecting whether functional p53 is encoded (e.g., genetically encoded) or can be expressed in a biological sample comprising or obtained from an abnormally proliferating cell or cancer cell from a subject, if functional p53 is encoded or can be expressed, detecting the level of HDM2, or HDMX, or both, in the sample, selecting a treatment from the group consisting of:
  (i) a treatment comprising administering a therapeutically effective amount of composition comprising a HDM2 modulating agent;
  (ii) a treatment comprising administering a therapeutically effective amount of a composition comprising a HDMX modulating agent; and
  (iii) a treatment comprising administering a therapeutically effective amount of a composition comprising a HDM2 modulating agent and a HDMX modulating agent, wherein treatment (i) is selected if the level of HDM2 is substantially greater than the level of HDMX in the sample, treatment (ii) is selected if the level of HDMX is substantially greater than the level of HDM2 in the sample, and treatment (iii) is selected if the levels of HDM2 and HDMX are about equal in the sample, thereby selecting a treatment for cancer in the subject, and administering to the subject a treatment in accordance with treatment (i), (ii), or (iii), wherein the selecting of a treatment and the administering of a treatment steps are performed by independent or the same parties at the same or different times. In some instances of such methods the HDM2 modulating agent of (i) is not a stapled peptide shown in FIG. 1C. In some embodiments, treatment (i) is selected if HDM2 is expressed and HDMX is not expressed. In some embodiments, treatment (ii) is selected if HDMX is expressed and HDM2 is not expressed. In some embodiments, treatment (iii) comprises administering the HDM2 inhibitor and the HDMX inhibitor simultaneously or separately. In some instances, the step of detecting the level of HDMX comprises detecting the presence of a p53-HDMX complex. In some embodiments, HDMX modulating agents can include peptides described herein. In some embodiments, the peptides can be cross-linked by one or more internal cross-linkers. In some embodiments, p53 is human p53. In some embodiments, the HDMX modulating agent can be a cross-linked peptide shown in FIG. 1C. In some embodiments, the HDMX modulating agent can be SAH-p53-8. In some embodiments, the HDM2 modulating agent is Nutlin-3. In some embodiments, the dose of the HDMX modulating agent and the HDM2 modulating agent used or administered in treatment (iii) is a synergistic dose or an additive dose.

In other aspects, the present disclosure provides compositions comprising one or more HDMX modulating agents and one or more HDM2 modulating agents. In some embodiments, the one or more HDMX modulating agents can include peptides described herein. In some embodiments, the peptides can be cross-linked by one or more internal cross-linkers. In some embodiments, p53 is human p53. In some embodiments, the HDMX modulating agent can be a cross-linked peptide shown in FIG. 1C. In some embodiments, the HDMX modulating agent can be SAH-p53-8. In some embodiments, the one or more HDM2 modulating agent is Nutlin-3.

In alternative aspects, the present disclosure further provides an isolated protein complex consisting of p53 and HDMX and antibodies and/or antibody fragments that bind specifically to this isolated protein complex. In some embodiments, the present disclosure provides methods for using the isolated protein complex in: cancer diagnostics and/or for monitoring treatment efficacy; and/or for developing personalized therapeutic methods for treating cancer in a subject.

In some aspects, the present disclosure provides kits that include compositions for detecting p53 and one or more of HDMX, HDM2, and/or a p53-HDMX complex; and instructions for developing a personalized treatment regimen for the treatment of cancer in a subject with cancer based on the detection of one or more of p53 and one or more of HDMX, HDM2, and/or a p53-HDMX complex. In some embodiments, the present disclosure provides kits that include one or more HDMX modulating agents and/or one or more HDM2 modulating agents; one or more devices suitable for administration of the one or more HDMX modulating agents and/or one or more HDM2 modulating agents; and instructions providing how the one or more HDMX modulating agents and/or one or more HDM2 modulating agents should be administered. Kits that include compositions for detecting p53 and one or more of HDMX, HDM2, and/or a p53-HDMX complex; and instructions for developing a personalized treatment regimen for the treatment of cancer in a subject with cancer based on the detection of one or more of p53 and one or more of HDMX, HDM2, and/or a p53-HDMX complex and one or more HDMX modulating agents and/or one or more HDM2 modulating agents; one or more devices suitable for administration of the one or more HDMX modulating agents and/or one or more HDM2 modulating agents; and instructions providing how the one or more HDMX modulating agents and/or one or more HDM2 modulating agents should be administered are also provided.

In some aspects, the present disclosure provides methods of treating a subject scheduled to receive radiation therapy. Such methods can include administering to the subject one or more HDMX modulating agents and/or one or more HDM2 modulating agents prior to at least one dose of radiation therapy.

In some aspects, the present disclosure provides methods of treating subjects with cancer. These methods can include administering to the subjects one or more HDMX modulating agents and/or one or more HDM2 modulating agents prior to at least one dose of radiation therapy and exposing the subject to radiation therapy. In some embodiments, the one or more HDMX modulating agents and/or one or more HDM2 modulating agents are administered locally to the gut of the subject. In some embodiments, the one or more HDMX modulating agents and/or one or more HDM2 modulating agents are administered systemically. In some embodiments, HDMX modulating agents can include peptides having amino acid sequences with at least 60% identity to the transactivation domain of p53, peptides having amino acid sequences with at least at least 60% identity to the transactivation domain of p53, wherein the amino acids on the interacting face of the peptide are conserved, and peptides having amino acid sequences with at least at least 60% identity to the transactivation domain of p53, wherein one or more of the amino acids on the interacting face of the peptide are substituted with a conservative amino acid that does not alter the interacting face of the peptide. In some embodiments, the peptides can be crosslinked by one or more internal crosslinkers. In some embodiments, p53 is human p53. In some embodiments, the HDMX modulating agent can be a cross-linked peptide shown in FIG. 1C. In some embodiments, the HDMX modulating agent can be SAH-p53-8. In some embodiments, the HDM2 modulating agent is Nutlin-3. In some embodiments, the dose of the HDMX modulating agent and the HDM2 modulating agent is a synergistic dose or an additive dose. In some embodiments, the HDM2 modulating agent is not a cross-linked peptide shown in FIG. 1C.

In some aspects, the disclosure provides internally cross-linked polypeptides comprising at least six contiguous amino acids of the amino acid sequence $Xaa_1$-$Xaa_2$-$Xaa_3$-$Xaa_4$-$Xaa_5$-$Phe_6$-$Xaa_7$-$Xaa_8$-$Xaa_9$-$Trp_{10}$-$Xaa_{11}$-$Xaa_{12}$-$Leu_{13}$-$Xaa_{14}$-$Xaa_{15}$-$Xaa_{16}$ (SEQ ID NO: 22), wherein: $Xaa_1$ is Leu or Gln, or is missing; $Xaa_2$ is Ser or is missing; $Xaa_3$ is Gln or is missing; $Xaa_4$ is Glu or Gln or Ala; $Xaa_5$ is Thr or Ala; $Phe_6$ is Phe or a conservative substitution thereof; $Xaa_7$=Ser; $Xaa_8$=Asp or Asn or any amino acid other than Asp and Glu; $Xaa_9$ is Leu; $Trp_{10}$ is Trp or a conservative substitution thereof; $Xaa_{11}$=Lys or a positively charged amino acid; $Xaa_{12}$ is Leu or Lys, or Ala; $Leu_{13}$ is Leu or a conservative substitution thereof; $Xaa_{14}$=Pro or is missing; $Xaa_{15}$=Glu, or Gln or Ala, or any amino acid other than Asp and Glu, or is missing; $Xaa_{16}$ is Asn or is missing, wherein the side chains of at least two amino acids separated by two, three, or six amino acids are replaced by an internal cross-link. In some embodiments, the internally cross-linked peptides include wherein: $Xaa_1$ is Leu or is missing; $Xaa_2$ is Ser or is missing; $Xaa_3$ is Gln or is missing; $Xaa_4$ is Glu; $Xaa_5$ is Thr; $Phe_6$ is Phe; $Xaa_7$ is Ser; $Xaa_8$ is Asp; $Xaa_9$ is Leu; $Trp_{10}$ is Trp; $Xaa_{11}$ is Lys; $Xaa_{12}$ is Leu; $Leu_{13}$ is Leu; $Xaa_{14}$ is Pro or is missing; $Xaa_{15}$ is Glu, or is missing; $Xaa_{16}$ is Asn or is missing, wherein: one, two, and/or three of $Phe_6$, $Trp_{10}$, and/or $Leu_{13}$ are replaced by a conservative amino acid substitution that does not alter the interaction between the binding face of the peptide and HDMX; and/or amino acids outside residues corresponding to $Phe_6$, $Trp_{10}$, and/or $Leu_{13}$ are at least 30% (e.g., 30%, 40%, 50%, 60%, 70%, 80%, 90%, 95%, 98%, or 100%) identical to the sequence of SEQ ID NO:1 or SEQ ID NO:2. In some embodiments, the peptides comprise the amino acid sequence of SEQ ID NO: 10. In some embodiments, the internally cross-linked peptides include at least two amino acids with side chains replaced by an internal cross-link selected from a staple shown in Table 1. In some embodiments, the internally cross-linked peptides include at least two amino acids with side chains replaced by an internal cross-link are selected from a stitch shown in Table 1. In some embodiments, the at least two amino acids with side chains replaced by an internal cross-link comprise two or more staples selected from Table 1. In some embodiments, the at least two amino acids with side chains replaced by an internal cross-link comprises at least one staple and at least one stitch shown in Table 1. In some embodiments, the at least two amino acids with side chains replaced by an internal cross-link are positioned between $Xaa_7$ and $Xaa_{14}$. In some embodiments, the at least two amino acids with side chains replaced by an internal cross-link includes one or more staples in which the at least two amino acids are separated by 6 amino acids. In some embodiments, the internal cross-links are located at one or more positions shown in SEQ ID NOs:2-21.

In some aspects, the disclosure provides pharmaceutical composition comprising one or more cross-linked peptides disclosed herein (e.g., one or more peptides disclosed in Table 1 or FIG. 1C).

In some aspects, the disclosure provides pharmaceutical composition comprising one or more cross-linked peptides disclosed herein (e.g., one or more peptides disclosed in Table 1 or FIG. 1C) and one or more HDM2 modulating agents. In some aspects, the one or more HDM2 modulating agents include Nutlin-3.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 12 is a cartoon depicting the reactivation of p53 by SAH-p53-8 binding to HDMX.

FIG. 13 shows the amino acid sequence of human p53 (SEQ ID NO:1: Genbank Accession Number CAAA42627 (CAA42627.1); gi:50637).

Like reference symbols in the various drawings indicate like elements.

DETAILED DESCRIPTION

Figures 1A, 1B:
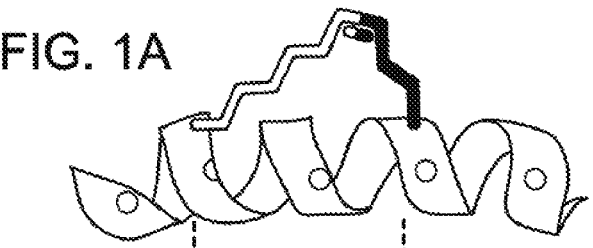
FIG. 1A is a cartoon showing the structure of an exemplary stapled p53 alpha helix.
FIG. 1B shows amino acids 14-29 of the amino acid sequence of wild type p53 (SEQ ID NO:2), SAH-p53-8 (SEQ ID NO: 10), and SAH-p53-8$_{F19A}$ (SEQ ID NO: 13). Amino acids critical to the activity of the peptide are shown in boxes. Tethered amino acids are shown as *.

The present disclosure is based, inter alia, on the surprising discovery that p53 stapled peptides, e.g., p53 stapled peptides initially developed to target HDM2, bind with high affinity to HDMX. Moreover, the p53 stapled peptides bind to HDMX with 25-fold greater affinity than they do to HDM2. Accordingly, the present disclosure provides novel methods and compositions (e.g., combinations of compositions) for treating or developing treatments for certain cancers.

Cancers suitable for treatment include those in which cancer cells express some level of functional p53, or in which functional p53 expression can be induced. For example, any cancer cell in which functional p53 is expressed but wherein the levels or activity of p53 are reduced in the cell by HDMX and/or HDMX can be beneficially treated using the compositions and methods disclosed herein.

As disclosed herein, p53 activity can be increased in cancer cells using, in some circumstances (disclosed herein), a HDMX modulating agent (e.g., a stapled peptide such as those disclosed in FIG. 1C) alone, or, in other circumstances (also disclosed herein), a combination of a HDMX modulating agent with a HDM2 modulating agent. As shown herein, such increases in p53 activity can lead to reduced viability or death of cancer cells in vitro and in vivo. Accordingly, compositions and methods disclosed herein can be used for the treatment of cancer. Agents suitable for use as HDMX and HDM2 modulating agents in the compositions and methods disclosed herein are disclosed below.

HDMX Modulating Agents

HDMX modulating agents encompassed by the present disclosure include agents that increase the expression, levels and/or activity of p53 in a cell by directly (e.g., by binding) or indirectly (e.g., via a molecule or pathway that regulates HDMX expression and/or activity (e.g., such as the ubiquitination pathway and components of this pathway such as E3 ubiquitin ligase)) inhibiting) the expression (e.g., protein or mRNA expression) and/or levels (e.g., protein levels) of HDMX in a cell.

In some embodiments, a HDMX agent can include one or more of the agents disclosed below. For example, a HDMX agent can include: (1) one or more non-cross-linked peptides that bind to HDMX; (2) one or more stapled or stitched p53 peptides that bind to HDMX; (3) one or more small molecules that bind to HDMX; (4) one or more antibodies or antibody fragments that bind (e.g., bind specifically to) HDMX; (5) one or more nucleic acid molecules (e.g., inhibitory nucleic acid molecules (e.g., RNAi or siRNA) that reduce HDMX expression; (6) one or more pharmaceuticals that that reduce the expression and/or activity of HDMX; and (7) one or more methods that that reduce the expression and/or activity of HDMX, and any combination of (1), (2), (3), (4), (5), (6) and/or (7) or any combination of (1) with (2), (3), (4), (5), (6) and/or (7).

In some embodiments, a HDMX modulating agent used in the methods and compositions disclosed herein: is not the same as a HDM2 modulating agent disclosed herein (e.g., the HDMX agent binds specifically to HDMX without binding (e.g., substantially binding) to HDM2).

In some embodiments, a HDMX modulating agent can bind to HDMX and HDM2. In such embodiments, however, the HDMX inhibitor will generally have a higher binding affinity for HDMX than for HDM2 (for example, the binding affinity of the HDMX modulating agent can be 2, 5, 10, 20, 25, 50, 75, 100, 25, 500, 1000, 2000, 5000, 10,000-fold or more for HDMX than for HDM2).

HDMX-Modulating Peptides

In some embodiments, the HDMX modulating agent is a peptide (e.g., a recombinant or synthetically produced peptide). As noted above, such peptides can be non-cross-linked, stapled, or stitched, e.g., so long as the peptides interact with HDMX as described herein.

In some embodiments, HDMX modulating peptides can include (e.g., comprise, consist, or consist essentially of) amino acid sequences related or with identity to a portion or portions of the wild type human p53 protein or amino acid sequence (e.g., SEQ ID NO:1). For example, peptides can include one or more domains of wild-type p53. Such domains can be naturally contiguous. Alternatively, non-naturally contiguous p53 domains can be combined. In some instances, peptides can include at least six (e.g., 7, 8, 9, 10, 11, 12, 13, 14, 15, 16 or more including 361, less than 361, less than 300, less than 200, less than 100, less than 50, less than 25, and less than 20, contiguous amino acids of SEQ ID NO:1).

In some instances, peptides with identity to a portion or portions of SEQ ID NO: 1 can have a first level of identity for amino acids corresponding to amino acids in the interacting face of p53 (e.g., the interacting face of the transactivation domain of p53) and a second level of identity for amino acids not corresponding to the interacting face. For example, amino acids corresponding to amino acids in the interacting face of p53 (e.g., the interacting face of the transactivation domain of p53) can be conserved or can be conservative substitutions of the amino acids present in the interacting face of p53 (e.g., the interacting face of the transactivation domain of p53). In contrast, amino acids outside the interacting face can have at least or about 30%, at least or about 40%, at least or about 50%, at least or about 60%, at least or about 70%, at least or about 80%, at least or about 90%, at least or about 95%, at least or about 98%, at least or about 99%, or 100% identity to those amino acids outside the interacting face of the peptide in SEQ ID NOs:2, or 22-23). Alternatively or in addition, amino acids outside those in the interacting face can include amino acid substitutions and/or deletions, whether conservative or not. For example, amino acids outside those in the interacting face can include 1, 2, 3, 4, 5, 6, 7, 8, less than 10, less than 5, less than 4, less than 3, or less than 2 amino acid substitutions, deletions, and/or additions, whether conservative or not. Accordingly, the amino acid sequence of any peptide disclosed herein can be varied so long as the residues of the interacting face are identical to those of SEQ ID NO:2 or are conservative substitutions thereof.

The "interacting face" of the peptides herein includes those amino acid residues of the p53 alpha helix that interact (e.g., interact specifically or bind specifically) with HDMX. Amino acid residues contained within the interacting face of p53, including amino acid residues contained within the interacting face of the p53 transactivation domain, are known in the art (see, e.g., Kussie et al., Science, 274(5289): 948-953 (1996), and Joseph et al., Cell Cycle, 9(22):4560-4568 (2010)). In some instances, amino acids of peptides disclosed herein that correspond to amino acids within the interacting face of p53 as disclosed by Kussie et al., Science, 274(5289):948-953 (1996) or Joseph et al., Cell Cycle, 9(22):4560-4568 (2010) can be the same or conservative substitutions of the amino acids disclosed by Kussie et al., Science, 274(5289):948-953 (1996), and Joseph et al., Cell Cycle, 9(22):4560-4568 (2010). For example, in some instances, amino acids in the interacting face of the peptides disclosed herein correspond to $Phe^{19}$, $Trp^{23}$, and $Leu^{26}$ of wild type p53 (SEQ ID NO:1). In some instances, these positions are underlined in the following sequence: LSQET FSDLWKLLPEN (SEQ ID NO:2). Conservative substitutions suitable for inclusion in the peptides disclosed herein are discussed below. For example, in some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In some instances, in the context of amino acids in the interacting face of the peptides disclosed herein (e.g., SEQ ID NO:1 and SEQ ID NOs:2-21), a conservative amino acid substitution is an amino acid substitution that does not change the structure of the hydrophobic interacting face of the peptide. For example, a conservative amino acid substitution is an amino acid substitution that does not reduce (e.g., substantially reduce) binding of the peptide to HDMX. Methods for detecting any reduction in binding can include comparing binding affinity following conservative amino acid substitution, wherein any amino acid substitution that reduces (e.g., substantially reduces) binding are not conservative amino acid substitutions. In some embodiments, substantially reduced binding can include binding that is 10%, 20%, 30%, 40%, 50%, 60%, 70%, 80%, 90%, 95%, 98%, 99%, or 100% less than binding of the unmodified peptide to HDMX. Methods for assessing interaction between a peptide and HDMX are disclosed herein. Methods for identifying the interactive face of a peptide are known in the art (see, e.g., Broglia et al., Protein sci., 14(10):2668-81, 2005; Hammond et al., J. Pharm. Sci., 98(1):4589-603, 2009; Ng and Yang, J. Phys. Chem. B., 111(50):13886-93, 2007; and Bird et al., PNAS USA, 197: 14093, 2010).

In some embodiments, peptides include (e.g., comprise, consist, or consist essentially of) at least six (e.g., 7, 8, 9, 10, 11, 12, 13, 14, 15, or 16) contiguous amino acids of the amino acid sequence: $Xaa_1$-$Xaa_2$-$Xaa_3$-$Xaa_4$-$Xaa_5$-$Phe_6$-$Xaa_7$-$Xaa_8$-$Xaa_9$-$Trp_{10}$-$Xaa_{11}$-$Xaa_{12}$-$Leu_{13}$-$Xaa_{14}$-$Xaa_{15}$-$Xaa_{16}$ (SEQ ID NO: 22), corresponding to the transactivation domain of p53 (e.g., SEQ ID NO:1), wherein each or any of $Xaa_1$-$Xaa_5$, $Xaa_7$-$Xaa_9$, and $Xaa_{11}$-$Xaa_{16}$ are any amino acid (e.g., any of the 20 naturally occurring amino acids) or are missing. In some embodiments:

$Xaa_1$ is Leu or Gln, or is missing;
$Xaa_2$ is Ser or is missing;
$Xaa_3$ is Gln or is missing;
$Xaa_4$ is Glu or Gln or Ala;
$Xaa_5$ is Thr or Ala;
$Phe_6$ is Phe or a conservative substitution thereof;
$Xaa_7$=Ser;
$Xaa_8$=Asp or Asn or any amino acid other than Asp and Glu (preferably Asn);
$Xaa_9$ is Leu;
$Trp_{10}$ is Trp or a conservative substitution thereof;
$Xaa_{11}$=Lys or a positively charged amino acid (preferably Arg);
$Xaa_{12}$ is Leu or Lys, or Ala;
$Leu_{13}$ is Leu or a conservative substitution thereof;
$Xaa_{14}$=Pro or is missing;
$Xaa_{15}$=Glu, or Gln or Ala, or any amino acid other than Asp and Glu (preferably Gln) or is missing;
$Xaa_{16}$ is Asn or is missing,
wherein: one or more (e.g., 1, 2, 3, 4, 5, 6, 7, 8, 9, 10, 11, 12, 13, 14, 15, or 16) amino acids of $Xaa_1$-$Xaa_2$-$Xaa_3$-$Xaa_4$-$Xaa_5$-$Phe_6$-$Xaa_7$-$Xaa_8$-$Xaa_9$-$Trp_{10}$-$Xaa_{11}$-$Xaa_{12}$-$Leu_{13}$-$Xaa_{14}$-$Xaa_{15}$-$Xaa_{16}$ are replaced by a conservative amino acid substitution that does not alter the interacting face of the peptide; and/or amino acids outside residues corresponding to $Phe_6$, $Trp_{10}$, and/or $Leu_{13}$, are at least 80% (e.g., 80%, 85%, 90%, 95%, 98%, 99%, 99.5%, or 100%) identical to the sequence of SEQ ID NO:1; and/or amino acids outside residues corresponding to $Phe_6$, $Trp_{10}$, and/or $Leu_{13}$ include one or more (e.g., 1, 2, 3, 4, 5, 6, 7, 8, less than 10, less than 5, less than 4, less than 3, or less than 2) conservative or non-conservative substitutions or deletions, wherein the peptide is optionally adapted to have stabilized alpha helical secondary structure.

In some cases the peptides can include (e.g., comprise, consist, or consist essentially of) a portion of SEQ ID NO: 22 having the sequence: $Xaa_3$-$Xaa_4$-$Xaa_5$-$Phe_6$-$Xaa_7$-$Xaa_8$-$Xaa_9$-$Trp_{10}$-$Xaa_{11}$-$Xaa_{12}$-$Leu_{13}$ (SEQ ID NO: 23).

In some embodiments, as indicated above, amino acid sequences of the peptides herein can vary outside of those amino acids corresponding to the interacting face of SEQ ID NO:2 (e.g., $Phe_6$, $Trp_{10}$, and/or $Leu_{13}$) almost without limitation. For example, amino acids outside those in the interacting face can have at least or about 30%, at least or about 40%, at least or about 50%, at least or about 60%, at least or about 70%, at least or about 80%, at least or about 90%, at least or about 95%, at least or about 98%, at least or about 99%, or 100% identity to those amino acids outside the interacting face of the peptide in SEQ ID NOs:2, or 22-23). Alternatively or in addition, amino acids outside those in the interacting face can include amino acid substitutions and/or deletions, whether conservative or not. For example, amino acids outside those in the interacting face can include 1, 2, 3, 4, 5, 6, 7, 8, less than 10, less than 5, less than 4, less than 3, or less than 2 amino acid substitutions, deletions, and/or additions, whether conservative or not. Accordingly, the amino acid sequence of any peptide disclosed herein can be varied so long as the residues of the interacting face are identical to those of SEQ ID NO:2 or are conservative substitutions thereof. In some instances, peptides can include (e.g. comprise, consist essentially of, or consist of) LSQETFSDLWKLLPEN (SEQ ID NO:2).

In some embodiments, the peptides can include (comprise, consist, or consist essentially of) one or more of the peptides disclosed in Pazgier et al., PNAS, 106; 4665-4670 (2009), which is hereby incorporated by reference in its entirety. For example, the HDMX modulating agent can include the peptide TSFAEYWNLLSP (termed PMI (SEQ ID NO:24)) and LTFEHYWAQLTS (termed pDI (SEQ ID NO:25)) disclosed in Pazgier et al., PNAS, 106; 4665-4670 (2009).

In some embodiments, the HDMX modulating peptides are cross-linked (e.g., stapled or stitched) by one or more intra-peptide cross-linkers. "Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (Blackwell et al., J. Org. Chem., 66: 5291-5302, 2001; Angew et al., Chem. Int. Ed. 37:3281, 1994). As used herein, the term "peptide stapling," includes the joining of two double bond-containing side-chains, two triple bond-containing side-chains, or one double bond-containing and one triple bond-containing side chain, which may be present in a polypeptide chain, using any number of reaction conditions and/or catalysts to facilitate such a reaction, to provide a singly "stapled" polypeptide. Additionally, the term "peptide stitching," as used herein, refers to multiple and tandem (e.g., a single amino acid is cross-linked to two amino acids) "stapling" events in a single polypeptide chain to provide a "stitched" (multiply stapled) polypeptide. Peptide stitching is described in WO 2008121767 and in WO 2010/068684, which are both hereby incorporated by reference.

Stapling of a peptide using all-hydrocarbon cross-link has been shown to help maintain its native conformation and/or secondary structure, particularly under physiologically relevant conditions (Schafmiester et al., J. Am. Chem. Soc., 122:5891-5892, 2000; Walensky et al., Science, 305:1466-1470, 2004).

Stapling the polypeptide herein by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's hydrophobicity, may allow for better penetration of the peptide into the target cell's membrane (e.g., through an energy-dependent transport mechanism such as pinocytosis), and/or may lead to an improvement in the peptide's biological activity relative to the corresponding non cross-linked (e.g., "unstitched" or "unstapled") peptide. Such constraints have been applied to the apoptosis-inducing BID-BH3 alpha-helix, resulting in a higher suppression of malignant growth of leukemia in an animal model compared to the unstitched polypeptide (Walensky et al., Science, 305:1466-1470, 2004; U.S. 2005/02506890; and U.S. 2006/0008848, each of which is incorporated herein by reference). Suitable cross-links (e.g., which are also referred to in the art as tethers) are described herein and in U.S. Patent Publication No. 2005/0250680, PCT/US2008/058575, U.S. Ser. No. 12/864,375 (WO 2009/108261), and WO 2010/148335.

Cross-linked peptides disclosed herein can include natural and non-natural amino acids and have a linkage between the alpha carbons of two amino acids (replacing the side chain of those amino acids). Methods suitable for obtaining (e.g., synthesizing), stapling, and purifying the peptides disclosed herein are known in the art (see, e.g., Bird et. al., Methods in Enzymol., 446:369-386 (2008); Walensky et al., Science, 305:1466-1470 (2004); Schafineister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety) and are described herein (see, e.g., Example 1).

In some embodiments, such cross-linked p53 peptides can exhibit a higher affinity for HDMX than a non-cross-linked or control peptide, e.g., an non-cross-linked peptide having the same amino acid sequence. In some embodiments, cross-linked p53 peptides can penetrate a cell membrane or have higher cell penetrability than a non-cross-linked or control peptide, e.g., a non-cross-linked peptide having the same amino acid sequence. In some embodiments, the HDMX modulating agent can include cross-linked versions of one or more of the peptides disclosed in Pazgier et al., PNAS, 106; 4665-4670 (2009). For example, the HDMX modulating agent can include a stapled or stitched version of TSFAEYWNLLSP (termed PMI (SEQ ID NO: 24)) or LTFEHYWAQLTS (termed pDI (SEQ ID NO: 25)) disclosed in Pazgier et al., PNAS, 106; 4665-4670 (2009). In some instances, PMI can be stapled using a crosslink (e.g., an internal crosslink) between any 2 amino acids so long as F, W, and the last L remain intact or are unmodified (e.g., so long as the amino acids in bold in TSFAEYWNLLSP (SEQ ID NO:24) remain intact or are unmodified). In some instances, pDI can be stapled using a crosslink (e.g., an internal crosslink) between any 2 amino acids so long as F, W, and the last L or T remain intact or are unmodified (e.g., so long as the amino acids in bold in LTFEHYWAQLTS (SEQ ID NO:25) or LTFEHYWAQLTS (SEQ ID NO:25) remain intact or are unmodified).

SEQ ID NO:1 is the sequence of human p53. In some instances, cross-linked peptides can include the sequence Leu Ser Gln Glu Thr Phe Ser Asp Leu Trp Lys Leu Leu Pro Glu Asn (amino acids 14 to 29 of SEQ ID NO:1 (SEQ ID NO:2)). Cross-linked peptides can also include Phe Ser Asn Leu Trp Arg Leu Leu Pro Gln Asn (SEQ ID NO:26) or the sequence Gln Ser Gln Gln Thr Phe Ser Asn Leu Trp Arg Leu Leu Pro Gln Asn (SEQ ID NO:27). In any of the sequence, the side chains of two amino acids separated by 2, 3, 4 or 6 amino acids can be replaced by the linking group $R_3$.

The stapled polypeptide can include all or part (e.g., at least 10, at least 11, at least 12, at least 13) of the following amino acid sequence: $Xaa_1Ser_2Gln_3Xaa_4Thr_5Phe_6$ $Xaa_7$ $Xaa_8Leu_9Trp_{10}Xaa_{11}Leu_{12}Leu_{13}Xaa_{14}Xaa_{15}Asn_{16}$.

(SEQ ID NO:28) wherein each of $Xaa_1$, $Xaa_4$, $Xaa_7$, $Xaa_8$, $Xaa_{11}$, $Xaa_{14}$, $Xaa_{15}$ are any amino acid (e.g., any of the 20 naturally occurring amino acids).

In some situations:

$Xaa_1$=Leu or Gln or an amino acid in which the side chain is replaced by the linking group $R_3$;

$Xaa_4$=Glu or Gln or an amino acid in which the side chain is replaced by the linking group $R_3Xaa_7$=Ser or the linking group $R_3$;

$Xaa_8$=Asp or any amino acid other than Asp and Glu (preferably Asn; e.g., $Xaa_8$ can be Asp or Asn) or an amino acid in which the side chain is replaced by the linking group $R_3$;

$Xaa_{11}$=Lys or a positively charged amino acid (preferably Arg) or an amino acid in which the side chain is replaced by the linking group $R_3$;

$Xaa_{14}$=Pro or an amino acid in which the side chain is replaced by the linking group $R_3$;

$Xaa_{15}$=Glu or any amino acid other than Asp and Glu (preferably Gln) or an amino acid in which the side chain is replaced by the linking group $R_3$.

In some situations, the peptide comprises SEQ ID NO:28 wherein $Xaa_1$=Leu or Gln or an amino acid in which the side chain is replaced by the linking group $R_3$;

$Xaa_4$=Glu or Gln or an amino acid in which the side chain is replaced by the linking group $R_3$;

$Xaa_7$=Ser or an amino acid in which the side chain is replaced by the linking group $R_3$;

$Xaa_8$=Asp, Asn or an amino acid in which the side chain is replaced by the linking group $R_3$;

$Xaa_{11}$=Lys, Arg or an amino acid in which the side chain is replaced by the linking group $R_{33}$;

$Xaa_{14}$=Pro or an amino acid in which the side chain is replaced by the linking group $R_3$;

$Xaa_{15}$=Glu, Gln or an amino acid in which the side chain is replaced by the linking group $R_3$.

In the stapled peptides, any position occupied by Gln can be Glu instead and any position occupied by Glu can be Gln instead. Similarly, any position occupied by Asn can be Asp instead and any position occupied by Aps can be Asn instead. The choice of Asn or Arg and Gln or Glu will depend on the desired charge of the stapled peptide.

In some cases the peptide comprises a portion of: $Gln_3Xaa_4Thr_5Phe_6Xaa_7Xaa_8Leu_9Trp_{10}Xaa_{11}Leu_{12}Leu_{13}$ (SEQ ID NO:29).

Within SEQ ID NO:29, the pairs of amino acid that can be cross-linked include, but are not limited to: the $5^{th}$ and $12^{th}$ amino acids; $4^{th}$ and $11^{th}$ amino acids; $7^{th}$ and $11^{th}$ amino acids; and $7^{th}$ and $14^{th}$ amino acids.

A tether or cross-link can extend across the length of one or two helical turns (i.e., about 3.4 or about 7 amino acids). Accordingly, amino acids positioned at i and i+3; i and i+4; or i and i+7 are ideal candidates for chemical modification and cross-linking Thus, for example, where a peptide has the sequence . . . $Xaa_1$, $Xaa_2$, $Xaa_3$, $Xaa_4$, $Xaa_5$, $Xaa_6$, $Xaa_7$, $Xaa_8$, $Xaa_9$ . . . (wherein, " . . . " indicates the optional presence of additional amino acids), cross-links between $Xaa_1$ and $Xaa_4$, (e.g., i+3) or between $Xaa_1$ and $Xaa_5$ (e.g., i+4), or between $Xaa_1$ and $Xaa_8$ (e.g., i+7) are useful as are cross-links between $Xaa_2$ and $Xaa_5$ (e.g., i+3), or between $Xaa_2$ and $Xaa_6$ (e.g., i+4), or between $Xaa_2$ and $Xaa_9$ (e.g., i+7), etc. The polypeptides can include more than one crosslink within the polypeptide sequence to either further stabilize the sequence or facilitate the stabilization of longer polypeptide stretches. If the polypeptides are too long to be readily synthesized in one part, independently synthesized, cross-linked peptides can be conjoined by a technique called native chemical ligation (Bang, et al., J. Am. Chem. Soc. 126:1377).

Alternatively or in addition, cross-linked peptides can include one or more (e.g., one, two, three, four, five, six, seven, eight, nine, ten, or more, less than 10, less than 9, less than 8, less than 7, less than 6, less than 5, less than 4, less than 3, or less than 2 staples and/or stitches.

Internal cross-links (e.g., staples and/or stitches) can be positioned on amino acids within a peptide to conserve the structural relationship of amino acids in the binding or interacting face of the peptide (e.g., to preserve the binding interface of a peptide). For example, one or more of 16 (see Table 1) can be stapled or stitched to at least one other amino acid to conserve the structural relationship of amino acids in the hydrophobic interaction face (see, e.g., Kussie et al., Science, 274(5289):948-953 (1996), and Joseph et al., Cell Cycle, 9(22):4560-4568 (2010)). Such internal cross-links can include: one or more staples; one or more stitches; and/or a combination of one or more staples with one or more stitches. As noted above, exemplary cross-linked peptides include SEQ ID NOs:2-21 (see FIG. 1C), and/or SEQ ID NO:10 (e.g., SAH-p53-8).

Selection of amino acids for modification (e.g., to support an internal cross-link) can also be facilitated by staple scanning. The term "staple scan" refers to the synthesis of a library of stapled peptides whereby the location of the i and i+3; i and i+4; and i and i+7 single and multiple staple, or stitches, are positioned sequentially down the length of the peptide sequence, sampling all possible positions, to identify desired or optimal properties and activities for the stapled or stitched constructs. Examples of staple scanning methods are illustrated in the figures.

In some instances, cross-linked peptides herein include at least two internally cross-linked or stapled amino acids, wherein the at least two amino acids are separated by 2 (i.e., i, i+3, shown in Table 1 as □), 3 (i.e., i, i+4, shown in Table 1 as ○), or, 6 (i.e., i, i+7, shown in Table 1 as ▲) amino acids. While at least two amino acids are required to support an internal cross-link (e.g., a staple), additional pairs of internally cross-linked amino acids can be included in a peptide, e.g., to support additional internal cross-links (e.g., staples). For example peptides can include 1, 2, 3, 4, 5, or more staples.

Alternatively or in addition, peptides can include three internally cross-linked or stitched amino acids. A peptide stitch includes at least three internally cross-linked amino acids, wherein the middle of the three amino acids (referred to here as the core or central amino acid and shown in Table 1 as "i") forms an internal cross-link (between alpha carbons) with each of the two flanking modified amino acids. The core amino acid includes two internally cross-linked side chains, which can be saturated or not saturated. Amino acids cross-linked to the core amino acid can be separated from the core amino acid in either direction by 2, 3, or 6 amino acids (e.g., i, i−3, i, i−4, i, i−7 (shown in Table 1 as ■, ●, and ▼, respectively), i, i+3, i, i+4, i, i+7 (shown in Table 1 as □, ○, and ▲, respectively), where "i" is the core amino acid). The number of amino acids on either side of the core (e.g., between the core amino acid and an amino acid cross-linked to the core) can be the same or different. In some instances, a stitch can include 3, 4, 5, or more internally cross-linked amino acids. In some instances, peptides can include 1, 2, 3, 4, 5, or more stitches.

In some embodiments, peptides herein can include a combination of at least one (e.g., 1, 2, 3, 4, or 5) staple and at least one (e.g., 1, 2, 3, 4, or 5) stitch.

In some embodiments, the tethers, e.g., hydrocarbon staples are used to stabilize structures other than helices. In such cases, the ends of the tethers can be placed at intervals other than at i, i+3, i+4, and i+7.

As disclosed above, peptides herein include at least two modified amino acids that together form an internal (intramolecular) cross-link, wherein the at least two modified amino acids are separated by 2 (i.e., i, i+3, shown in Table 1 as □), 3 (i.e., i, i+4, shown in Table 1 as ○), or, 6 (i.e., i, i+7, shown in Table 1 as ▲) amino acids. For example, peptides can include cross-linked amino acids at one or more of the positions illustrated in Table 1.

TABLE 1

Positions of Amino Acids with Internally Cross-Linkable or Cross-Linked Side Chains (within SEQ ID NO: 23)

| Xaa1 | Xaa2 | Xaa3 | Xaa4 | Xaa5 | Phe6 | Xaa7 | Xaa8 | Xaa9 | Trp10 | Xaa11 | Xaa12 | Leu13 | Xaa14 | Xaa15 | Xaa16 |
|---|---|---|---|---|---|---|---|---|---|---|---|---|---|---|---|
| i1 | | | □ | ○ | | ▲ | | | | | | | | | |
| | i2 | | | □ | ○ | | ▲ | | | | | | | | |
| | | i3 | | | □ | ○ | | ▲ | | | | | | | |
| ■ | | | i4 | | | □ | ○ | | ▲ | | | | | | |
| ● | ■ | | | i5 | | | □ | ○ | | ▲ | | | | | |
| | ● | ■ | | | i6 | | | □ | ○ | | ▲ | | | | |
| | | ● | ■ | | | i7 | | | □ | ○ | | ▲ | | | |
| ▼ | | | ● | ■ | | | i8 | | | □ | ○ | | ▲ | | |
| | ▼ | | | ● | ■ | | | i9 | | | □ | ○ | | ▲ | |
| | | ▼ | | | ● | ■ | | | i10 | | | □ | ○ | | ▲ |
| | | | ▼ | | | ● | ■ | | | i11 | | | □ | ○ | |
| | | | | ▼ | | | ● | ■ | | | i12 | | | □ | ○ |
| | | | | | ▼ | | | ● | ■ | | | i13 | | | □ |
| | | | | | | ▼ | | | ● | ■ | | | i14 | | |
| | | | | | | | ▼ | | | ● | ■ | | | i15 | |
| | | | | | | | | ▼ | | | ● | ■ | | | i16 | wherein; "i" is the anchor; □ is i + 3; ○ is i + 4; ▲ is i + 7; ■ is i − 3; ● is i − 4; and ▼ is i − 7.

In some embodiments, the invention features a modified polypeptide of Formula

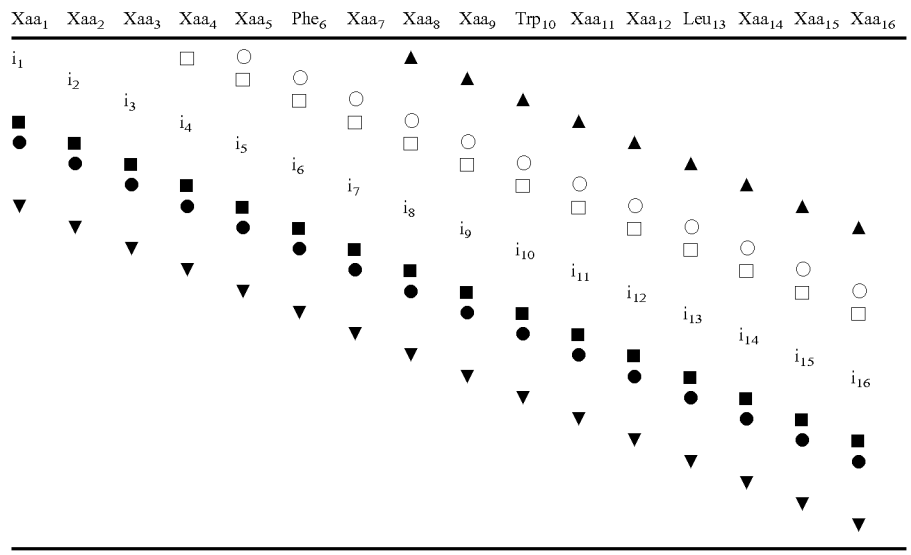

Formula (I)

or a pharmaceutically acceptable salt thereof,
wherein;
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;
$R_3$ is alkylene, alkenylene or alkynylene, or $[R_4'—K—R_4]_n$; each of which is substituted with 0-6 $R_5$;
$R_4$ and $R_4'$ are independently alkylene, alkenylene or alkynylene (e.g., each are independently a $C_1$, $C_2$, $C_3$, $C_4$, $C_5$, $C_6$, $C_7$, $C_8$, $C_9$ or $C_{10}$ alkylene, alkenylene or alkynylene);
$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;
K is O, S, SO, $SO_2$, CO, $CO_2$, $CONR_6$, or

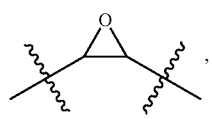 [SMILES: *C1OC1*]

aziridine, episulfide, diol, amino alcohol;
$R_6$ is H, alkyl, or a therapeutic agent;
n is 2, 3, 4 or 6;
x is an integer from 2-10;
w and y are independently an integer from 0-100;
z is an integer from 1-10 (e.g., 1, 2, 3, 4, 5, 6, 7, 8, 9, 10); and
each Xaa is independently an amino acid (e.g., one of the 20 naturally occurring amino acids or any naturally occurring non-naturally occurring amino acid);
wherein the polypeptide comprises at least 8 contiguous amino acids of SEQ ID NO:1 (human p53) or a variant thereof, SEQ ID NO:2 or a variant thereof, or another polypeptide sequence described herein except that: (a) within the 8 contiguous amino acids of SEQ ID NOs:1 or 2 the side chains of at least one pair of amino acids separated by 2, 3 or 6 amino acids is replaced by the linking group, $R_3$, which connects the alpha carbons of the pair of amino acids as depicted in Formula I; and (b) the alpha carbon of the first of the pair of amino acids is substituted with $R_1$ as depicted in formula I and the alpha carbon of the second of the pair of amino acids is substituted with $R_2$ as depicted in Formula I.

In another aspect, the invention features a modified polypeptide of Formula (II),

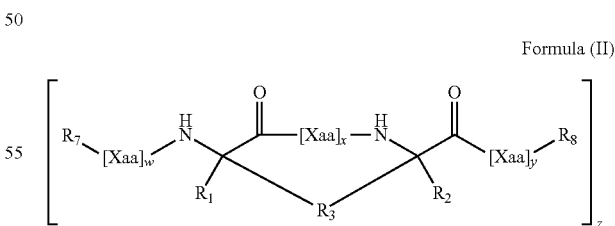

Formula (II)

or a pharmaceutically acceptable salt thereof,
wherein;
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;
$R_3$ is alkylene, alkenylene or alkynylene, or $[R_4'—K—R_4]_n$; each of which is substituted with 0-6 $R_5$;

$R_4$ and $R_4'$ are independently alkylene, alkenylene or alkynylene (e.g., each are independently a $C_1$, $C_2$, $C_3$, $C_4$, $C_5$, $C_6$, $C_7$, $C_8$, $C_9$ or $C_{10}$ alkylene, alkenylene or alkynylene);

$R_5$ is halo, alkyl, $OR_6$, $NHR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

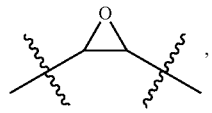

aziridine, episulfide, diol, amino alcohol, diamine;

$R_6$ is H, alkyl, or a therapeutic agent;

n is 2, 3, 4, 5, or 6;

x is an integer from 2-10;

w and y are independently an integer from 0-100;

z is an integer from 1-10 (e.g., 1, 2, 3, 4, 5, 6, 7, 8, 9, 10); and each Xaa is independently an amino acid (e.g., one of the 20 naturally occurring amino acids or any naturally occurring non-naturally occurring amino acid);

$R_7$ is PEG, a tat protein, an affinity label, a targeting moiety, a fatty acid-derived acyl group, a biotin moiety, a fluorescent probe (e.g. fluorescein or rhodamine) linked via, e.g., a thiocarbamate or carbamate linkage;

$R_8$ is H, OH, $NH_2$, $NHR_{8a}$, $NR_{8a}R_{8b}$;

wherein the polypeptide comprises at least 8 contiguous amino acids of SEQ ID NO:1 (human p53) or a variant thereof, SEQ ID NO: 2 or a variant thereof, or another polypeptide sequence described herein except that: (a) within the 8 contiguous amino acids of SEQ ID NOs:1 or 2 the side chains of at least one pair of amino acids separated by 2, 3 or 6 amino acids is replaced by the linking group, $R_3$, which connects the alpha carbons of the pair of amino acids as depicted in formula I; and (b) the alpha carbon of the first of the pair of amino acids is substituted with $R_1$ as depicted in Formula II and the alpha carbon of the second of the pair of amino acids is substituted with $R_2$ as depicted in Formula II.

In the case of Formula I or Formula II, the following embodiments are among those disclosed.

In cases where x=2 (i.e., i+3 linkage), R3 can be a C7 alkylene, alkenylene. Where it is an alkenylene there can one or more double bonds. In cases where x=6 (i.e., i+4 linkage), $R_3$ can be a C1, C12 or C13 alkylene or alkenylene. Where it is an alkenylene there can one or more double bonds. In cases where x=3 (i.e., i+4 linkage), $R_3$ can be a C8 alkylene, alkenylene. Where it is an alkenylene there can one or more double bonds.

In certain instances, the two alpha, alpha disubstituted stereocenters (alpha carbons) are both in the R configuration or S configuration (e.g., i, i+4 cross-link), or one stereocenter is R and the other is S (e.g., i, i+7 cross-link). Thus, where Formula I is depicted as

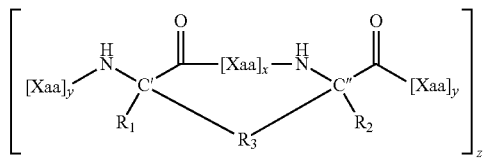

the C' and C" disubstituted stereocenters can both be in the R configuration or they can both be in the S configuration, for example when x is 3. When x is 6, the C' disubstituted stereocenter is in the R configuration and the C" disubstituted stereocenter is in the S configuration or the C' disubstituted stereocenter is in the S configuration and the C" disubstituted stereocenter is in the R configuration. The $R_3$ double bond may be in the E or Z stereochemical configuration. Similar configurations are possible for the carbons in Formula II corresponding to C' and C" in the formula depicted immediately above.

In some instances $R_3$ is $[R_4—K—R_4']_n$; and $R_4$ and $R_4'$ are independently alkylene, alkenylene or alkynylene (e.g., each are independently a C1, C2, C3, C4, C5, C6, C7, C8, C9 or $C_{10}$ alkylene, alkenylene or alkynylene In some instances, the polypeptide includes an amino acid sequence which, in addition to the amino acids side chains that are replaced by a cross-link, have 1, 2, 3, 4 or 5 amino acid changes in any of SEQ ID NOs:1 or 2.

The tether can include an alkyl, alkenyl, or alkynyl moiety (e.g., $C_5$, $C_8$ or $C_{11}$ alkyl or a $C_5$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl). $[Xaa]_y$ and $[Xaa]_w$ are peptides that can independently comprise at least 1, 2, 3, 4, 5, 6, 7, 8, 9, 10, 11, 12, 13, 14, 15, 16, 17, 18, 19, 20, 25 or more contiguous amino acids (preferably 2 or 5 contiguous amino acids) of a p53 polypeptide (e.g., any of SEQ ID NOs: 1 or 2) and $[Xaa]_x$ is a peptide that can comprise 3 or 6 contiguous amino acids of acids of a p53 peptide.

The peptide can comprise 8, 9, 10, 11, 12, 13, 14, 15, 16, 17, 18, 19, 20, 25, 30, 35, 40, 45, 50 amino acids, or any number between 20-50 amino acids, or any range between any 2 of the recited number of amino acids, of a p53 polypeptide. The amino acids are contiguous except that one or more pairs of amino acids separated by 3 or 6 amino acids are replaced by amino acid substitutes that form a cross-link, e.g., via $R_3$. Thus, at least two amino acids can be replaced by tethered amino acids or tethered amino acid substitutes. Thus, where formula I is depicted as

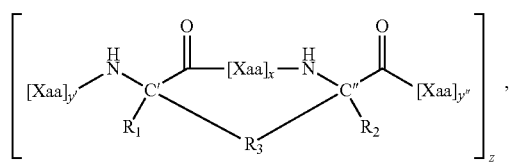

$[Xaa]_{y'}$, $[Xaa]_x$ and $[Xaa]_{y''}$ can each comprise contiguous polypeptide sequences from the same or different p53 peptides. The same is true for Formula II.

The peptides can include 10 (11, 12, 13, 14, 15, 16, 17, 18, 19, 20, 21, 22, 23, 24, 25, 30, 35, 40, 45, 50 or more) contiguous amino acids of a p53 polypeptide (e.g., SEQ ID NOs: 1 or 2) wherein the alpha carbons of two amino acids that are separated by three amino acids (or six amino acids) are linked via $R_3$, one of the two alpha carbons is substituted by $R_1$ and the other is substituted by $R_2$ and each is linked via peptide bonds to additional amino acids.

In some instances the polypeptide acts as dominant negative inhibitor p53 degradation. In some instances, the polypeptide also includes a fluorescent moiety or radioisotope or a moiety that can chelate a radioisotope (e.g., mercaptoacetyltriglycine or 1, 4, 7, 10-tetraazacyclododecane-N,N',N",N'"-tetraacetic acid (DOTA)) chelated to a radioactive isotope of Re, In or Y). In some instances, $R_1$ and $R_2$ are methyl; $R_3$ is $C_8$ alkyl, $C_{11}$ alkyl, $C_8$ alkenyl, $C_{11}$ alkenyl, $C_8$ alkynyl, or $C_{11}$ alkynyl; and x is 2, 3, or 6. In some instances, the polypeptide includes a PEG linker, a tat protein, an affinity label, a targeting moiety, a fatty acid-derived acyl group, a biotin moiety, a fluorescent probe (e.g. fluorescein or rhodamine), or a metal chelating group.

The peptides may contain one or more asymmetric centers and thus occur as racemates and racemic mixtures, single enantiomers, individual diastereomers and diastereomeric mixtures and geometric isomers (e.g. Z or cis and E or trans) of any olefins present. All such isomeric forms of these compounds are expressly included in the present invention. The compounds may also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the compounds disclosed herein (the invention expressly includes all such reaction products). All such isomeric forms of such compounds are included as are all crystal forms.

The peptides can also include amino acids containing both an amino group and a carboxyl group bonded to a carbon referred to as the alpha carbon. Also bonded to the alpha carbon is a hydrogen and a side-chain. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and unnaturally occurring amino acids prepared by organic synthesis or other metabolic routes. Table 2 below provides the structures of the side chains for each of the 20 common naturally-occurring amino acids. In this table the "—" at right side of each structure is the bond to the alpha carbon.

TABLE 2

| Amino acid | Single Letter | Three Letter | Structure of side chain |
| --- | --- | --- | --- |
| Alanine | A | Ala | $CH_3-$ |
| Arginine | R | Arg | $HN=C(NH_2)-NH-(CH_2)_3-$ |
| Asparagine | N | Asn | $H_2N-C(O)-CH_2-$ |
| Aspartic acid | D | Asp | $HO(O)C-CH_2-$ |
| Cysteine | C | Cys | $HS-CH_2-$ |
| Glutamine | Q | Gln | $H_2N-C(O)-(CH_2)_2-$ |
| Glutamic acid | E | Glu | $HO(O)C-(CH_2)_2-$ |
| Glycine | G | Gly | $H-$ |
| Histidine | H | His | $N=CH-NH-CH=C-CH_2-$ |
| Isoleucine | I | Ile | $CH_3-CH_2-CH(CH_3)-$ |
| Leucine | L | Leu | $(CH_3)_2-CH-CH_2-$ |
| Lysine | K | Lys | $H_2N-(CH_2)_4-$ |
| Methionine | M | Met | $CH_3-S-(CH_2)_2-$ |
| Phenylalanine | F | Phe | Phenyl-$CH_2-$ |
| Proline | P | Pro | $-N-(CH_2)_3-CH-$ |
| Serine | S | Ser | $HO-CH_2-$ |
| Threonine | T | Thr | $CH_3-CH(OH)-$ |

TABLE 2-continued

| Amino acid | Single Letter | Three Letter | Structure of side chain |
| --- | --- | --- | --- |
| Tryptophan | W | Trp | Phenyl-$NH-CH=C-CH_2-$ |
| Tyrosine | Y | Tyr | 4-OH-Phenyl-$CH_2-$ |
| Valine | V | Val | $CH_3-CH(CH_2)-$ |

A "non-essential" amino acid residue is a residue that can be altered from the wild-type sequence of a polypeptide (without abolishing or substantially altering its activity. An "essential" amino acid residue is a residue that, when altered from the wild-type sequence of the polypeptide, results in abolishing or substantially abolishing the polypeptide activity.

In some embodiments, the term "essential" amino acid residue as used herein, includes conservative substitutions of the essential amino acid. Generally, the "essential" amino acid residues are found at the interacting face of the alpha helix.

The symbol " ⟋ " when used as part of a molecular structure refers to a single bond or a trans or cis double bond.

The term "amino acid side chain" refers to a moiety attached to the α-carbon in an amino acids. For example, the amino acid side chain for alanine is methyl, the amino acid side chain for phenylalanine is phenylmethyl, the amino acid side chain for cysteine is methylthiol, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an alpha di-substituted amino acid).

The term polypeptide encompasses two or more naturally occurring or synthetic amino acids linked by a covalent bond (e.g., an amide bond). Polypeptides as described herein include full length proteins (e.g., fully processed proteins) as well as shorter amino acids sequences (e.g., fragments of naturally occurring proteins or synthetic polypeptide fragments).

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10

(inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctynyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridazyl, pyrimidyl, thiophenyl, quinolinyl, indolyl, thiazolyl, oxazolyl, isoxazolyl and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation or dihydroxylation) to provide one of compounds below.

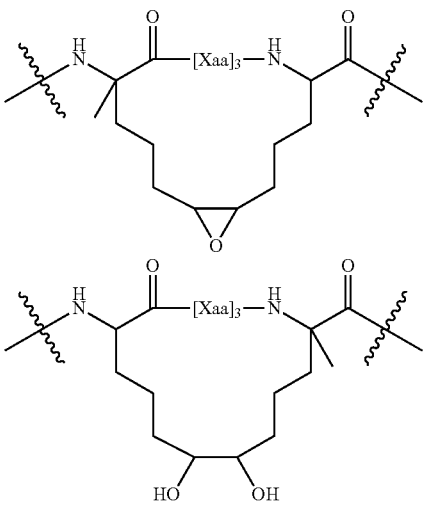

Either the epoxide moiety or one of the free hydroxyl moieties can be further functionalized. For example, the epoxide can be treated with a nucleophile, which provides additional functionality that can be used, for example, to attach a tag (e.g., a radioisotope or fluorescent tag). The tag can be used to help direct the compound to a desired location in the body or track the location of the compound in the body. Alternatively, an additional therapeutic agent can be chemically attached to the functionalized tether (e.g., an anti-cancer agent such as rapamycin, vinblastine, taxol, etc.). Such derivitization can alternatively be achieved by synthetic manipulation of the amino or carboxy terminus of the polypeptide or via the amino acid side chain. Other agents can be attached to the functionalized tether, e.g., an agent that facilitates entry of the polypeptide into cells.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

It is further envisioned that the staple itself may contribute to binding interactions at the surface of the target protein binding site, and thus, may be used to increase affinity while retaining target affinity, as has been reported (Stewart et al, Nature Chem. Biol., 2010; Joseph et al, Cell Cycle, 2010 (supra)).

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

In some instances it can be useful to create an inactive stapled peptide by replacing one or more (e.g., all three) of $Phe_6$, $Trp_{10}$, $Leu_{13}$ of the interacting face of p53 (e.g., of SEQ ID NO:1) with another amino acid, e.g., Ala. Such inactive stapled peptides can be useful, for example, as negative controls.

The stapled polypeptides can include a drug, a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethelene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

$XO-(CH_2CH_2O)_n-CH_2CH_2-Y$ where n is 2 to 10,000 and X is H or a terminal modification, e.g., a $C_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine Non-peptide linkers are also possible. For example, alkyl linkers such as $-NH(CH_2)_nC(O)-$, wherein n=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

The stapled peptides can also be modified, e.g., to facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration.

In some embodiments, the stapled peptides disclosed herein have an enhanced ability to penetrate cell membranes (e.g., relative to non-stapled peptides). These same peptides can also possess, or can be modified to possess, an apparent affinity to human serum proteins of 1 micromolar or weaker. In another embodiment, the improved cross-linked polypeptide possesses an apparent affinity to human serum proteins of 3 micromolar or weaker. In another embodiment, the improved cross-linked polypeptide possesses an apparent affinity to human serum proteins of 10 micromolar or weaker. In another embodiment, the improved cross-linked polypeptide possesses an apparent affinity to human serum proteins of 70 micromolar or weaker. In another embodiment, the improved cross-linked polypeptide possesses an apparent affinity to human serum proteins of between 1-70 micromolar. In another embodiment, the improved cross-linked polypeptide possesses an apparent affinity to human serum proteins of between 1-700 micromolar. In some embodiments, the improved cross-linked polypeptide possesses an estimated free fraction in whole blood of between 0.1-50%. In another embodiment, the improved cross-linked polypeptide possesses an estimated free fraction in whole blood of between 0.5-10%. For example, a polypeptide can be selected such that the apparent serum binding affinity (Kd*) of the crosslinked polypeptide is 1, 3, 10, 70 micromolar or greater. In other embodiments, the Kd* of the crosslinked polypeptide is 1 to 10, 70, or 700 micromolar. In other embodiments, the crosslinked polypeptides are selected such that it possesses an estimated free fraction in human blood of between 0.1 and 50%, or between 0.15 and 10%. Methods for quantifying the propensity for any particular peptide to bind to serum proteins are known in the art (see, e.g., U.S. Patent Application Publication No. 2010/0216688, published Aug. 26, 2010).

In some embodiments, the improved cross-linked polypeptide possesses an estimated free fraction in whole blood of between 0.1-50%. In another embodiment, the improved cross-linked polypeptide possesses an estimated free fraction in whole blood of between 0.5-10%.

In some embodiments, the HDMX modulating agent can be a stapled peptide, or can include a modification to a stapled peptide, disclosed in any one or more of: U.S. Patent Publication No. 2010/0168388, published Jul. 1, 2010; U.S. Patent Publication No. 2010/0216688, published Aug. 26, 2010; U.S. Patent Publication No. 2010/0184628, published Jul. 22, 2010; U.S. Patent Publication No. 2009/0047711, published Feb. 19, 2009; U.S. Patent Publication No. 2009/0088533, published Apr. 2, 2009; U.S. Patent Publication No. 2009/0326192, published Dec. 31, 2009; U.S. Patent Publication No. 2009/0275519, published Nov. 5, 2009; U.S. Patent Publication No. 2008/0262200, published Oct. 23, 2008; U.S. Patent Publication No. 2010/022549, published Jan. 28, 2010; U.S. Patent Publication No. 2010/0113466, published May 6, 2010; U.S. Patent Publication No. 2009/0069334, published Mar. 12, 2009, each of which are hereby incorporated by reference in their entirety.

In some embodiments, the HDMX modulating agent can be a stapled peptide, or can include a modification to a stapled peptide, e.g., at the amino and/or carboxyl terminus. In some embodiments, the amino and/or carboxyl terminal modification can include amino and/or carboxyl terminal derivatizations including, but not limited to, for example, N-terminal biotin, N-terminal Ac, N-terminal Ac-bala, N-terminal PEG, C-terminal amide, and/or C-terminal COOH.

In some embodiments, as noted above, the HDMX modulating agent may also bind to HDM2 (e.g., GenBank® Accession No.: 228952; GI:228952) and/or HDM4 (also referred to as HDMX; GenBank® Accession No.: 88702791; GI:88702791). In such instances, the affinity of the HDMX modulating agent for HDMX will be higher (e.g., substantially higher, e.g., 2, 3, 4, 5, 6, 7, 8, 9, 10, 11, 12, 13, 14, 15, 16, 17, 18, 19, 20, 30, 40, 50, 75, 100, 250, 500, 1000, or 2000 fold higher, or more than 2000 fold higher) than the affinity of the HDMX modulating agent for HDM2 or HDM4.

In some embodiments, the HDMX modulating agent can bind to both HDM2 and HDMX, but only inhibit (e.g., substantially inhibit) the activity of HDMX.

As noted above, methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-$NH_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

In the modified polypeptides, one or more conventional peptide bonds replaced by a different bond that may increase the stability of the polypeptide in the body. Peptide bonds can be replaced by: a retro-inverso bonds (C(O)—NH); a reduced amide bond (NH—$CH_2$); a thiomethylene bond (S—$CH_2$ or $CH_2$—S); an oxomethylene bond (O—$CH_2$ or $CH_2$—O); an ethylene bond ($CH_2$—$CH_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or $CH_3$; and a fluoro-ketomethylene bond (C(O)—CFR or CFR—C(O) wherein R is H or F or $CH_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. The polypeptides of the invention may also be conjugated to, for example, polyethylene glycol (PEG); alkyl groups (e.g., C1-C20 straight or branched alkyl groups); fatty acid radicals; and combinations thereof.

α,α-Disubstituted non-natural amino acids containing olefinic side chains of varying length can be synthesized by known methods (Williams et al. J. Am. Chem. Soc., 113: 9276, 1991; Schafineister et al., J. Am. Chem. Soc., 122: 5891, 2000; and Bird et al., Methods Enzymol., 446:369, 2008). For peptides where an i linked to i+7 staple is used (two turns of the helix stabilized) either one S5 amino acid and one R8 is used or one S8 amino acid and one R5 amino acid is used. R8 is synthesized using the same route, except that the starting chiral auxillary confers the R-alkyl-stereoisomer. Also, 8-iodooctene is used in place of 5-iodopentene Inhibitors are synthesized on a solid support using solid-phase peptide synthesis (SPPS) on MBHA resin.

Fmoc-protected α-amino acids (other than the olefinic amino acids Fmoc-$S_5$—OH, Fmoc-$R_8$—OH, Fmoc-$R_8$—OH, Fmoc-$S_8$—OH and Fmoc-$R_5$—OH), 2-(6-chloro-1-H-benzotriazole-1-yl)-1,1,3,3-tetramethylaminium hexafluorophosphate (HCTU), and Rink Amide MBHA resin are commercially available from, e.g., Novabiochem (San Diego, Calif.). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., Org. Synth., 80:31, 2003).

In some embodiments, stapled peptides can be generated using the following method. Peptides can be synthesized manually using Fmoc solid phase peptide chemistry on Rink amide MBHA resin with loading levels of 0.4-0.6 mmol/g resin. The following protocol was used:

1. The Fmoc protective group was removed with 20% piperidine in NMP for 30 min.
2. The resin was washed with NMP five times.
3. The subsequent Fmoc-protected amino acid was coupled for 30 min (60 min for a cross-linker) using Fmoc-AA (10 equiv., 4 equiv. for a cross-linker), HCTU (9.9 equiv., 3.9 equiv. for a cross-linker), and DIEA (20 equiv., 7.8 equiv. for a cross-linker).
4. The resin was washed with NMP five times.
5. Repeat from step 1.

All peptides were capped with a β-alanine residue at the N-terminus. CD experiments make use of peptides that have been acetylated at the N-terminus. The acetylation reaction consisted of deprotection of the Fmoc group as outlined above, followed by reaction with acetic anhydride and DIEA. All other experiments shown make use of fluoresceinated peptides at the N-terminus. To this end, the peptides with the deprotected N-terminus were exposed to fluorescein isothiocyanate in DMF overnight in the presence of DIEA.

Ring-closing metathesis reaction can be performed on the N-terminal capped peptides while still on the solid support in a disposable fritted reaction vessel. The resin was exposed to a 10 mM solution of bis(tricyclohexylphosphine)benzylidine ruthenium (IV) dichloride (Grubbs First Generation Catalyst) in 1,2-dichloroethane or dichloromethane for 2 hours. The catalyst addition and 2 hour metathesis reaction was repeated once. The resin-bound peptide was washed with $CH_2Cl_2$ three times and dried under a stream of nitrogen.

Peptides can be cleaved from the resin and deprotected by exposure to Reagent K (82.5% TFA, 5% thioanisole, 5% phenol, 5% water, 2.5% 1,2-ethanedithiol) or 95% TFA, 2.5% water, 2.5% triisopropylsilane and precipitated with methyl-tert-butyl ether at 4° C. and lyophilized. Peptides can be purified, e.g., using HPLC and optionally lyophilized.

In some embodiments, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Properties of the cross-linked polypeptides of the invention can be assayed, for example, using the methods described below.

Assays to Determine α-Helicity:

Compounds are dissolved in an aqueous solution (e.g. 50 mM potassium phosphate solution at pH 7, or distilled $H_2O$, to concentrations of 25-50 μM). Circular dichroism (CD) spectra are obtained on a spectropolarimeter (e.g., Jasco J-710) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity by the reported value for a model helical decapeptide (Yang et al., Methods Enzymol. 130:208 (1986)).

Assays to Determine Melting Temperature (Tm):

Peptidomimetic macrocycles or unmodified peptides are dissolved in distilled $H_2O$ (e.g. at a final concentration of 50 μM) and Tm is determined by measuring the change in ellipticity over a temperature range (e.g. 4 to 95° C.) on a spectropolarimeter (e.g., Jasco J-710) using standard parameters (e.g. wavelength 222 nm; step resolution, 0.5 nm; speed, 20 nm/sec; accumulations, 10; response, 1 sec; bandwidth, 1 nm; temperature increase rate: 1.degree. C./min; path length, 0.1 cm).

Protease Resistance Assays:

The amide bond of the peptide backbone is susceptible to hydrolysis by proteases, thereby rendering peptidic compounds vulnerable to rapid degradation in vivo. Peptide helix formation, however, typically buries the amide backbone and therefore may shield it from proteolytic cleavage. The peptidomimetic macrocycles of the present invention may be subjected to in vitro trypsin proteolysis to assess for any change in degradation rate compared to a corresponding uncrosslinked polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E.about.125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln [S] versus time.

Ex Vivo Stability Assays:

Peptidomimetic macrocycles and/or a corresponding uncrosslinked polypeptide can be each incubated with fresh mouse, rat and/or human serum (e.g. 1-2 mL) at 37° C. for, e.g., 0, 1, 2, 4, 8, and 24 hours. Samples of differing macrocycle concentration may be prepared by serial dilution with serum. To determine the level of intact compound, the following procedure may be used: The samples are extracted by transferring 100 μl of sera to 2 ml centrifuge tubes followed by the addition of 10 μL of 50% formic acid and 500 μL acetonitrile and centrifugation at 14,000 RPM for 10 min at 4.+−0.2° C. The supernatants are then transferred to fresh 2 ml tubes and evaporated on Turbovap under $N_2$<10 psi, 37° C. The samples are reconstituted in 100 μL of 50:50 acetonitrile:water and submitted to LC-MS/MS analysis. Equivalent or similar procedures for testing ex vivo stability are known and may be used to determine stability of macrocycles in serum.

In Vitro Binding Assays:

To assess the binding and affinity of peptidomimetic macrocycles and peptidomimetic precursors to acceptor proteins, a fluorescence polarization assay (FPA) can be used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

In Vitro Displacement Assays to Characterize Antagonists of Peptide-Protein Interactions:

To assess the binding and affinity of compounds that antagonize the interaction between a peptide and an acceptor protein, a fluorescence polarization assay (FPA) utilizing a fluoresceinated peptidomimetic macrocycle derived from a peptidomimetic precursor sequence is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). A compound that antagonizes the interaction between the fluoresceinated peptidomimetic macrocycle and an acceptor protein will be detected in a competitive binding FPA experiment.

Binding Assays in Intact Cells:

It is possible to measure binding of peptides or crosslinked polypeptides to their natural acceptors in intact cells by immunoprecipitation experiments, e.g., as described herein.

P-LISA and Immunofluorescence.

To assess the capacity of SAH-p53-8 to disrupt intracellular complexes of p53/HDMX in intact cells, a P-LISA assay was applied. U2OS cells expressing a doxycycline-inducible HA-HDMX construct (Wang et al., 2007) were seeded onto coverslips and treated with doxycyline for 24 h. SAH-p53-8 (10 µM), enantiomeric Nutlin-3 (10 µM) (Roche), or both compounds were added for the final 8 h of treatment. The cells were fixed in 3.7% paraformaldehyde, washed in PBS, and permeabilized in 0.2% Triton X-100 for 5 min. Coverslips were then blocked in 10% normal goat serum in PBS (NGS) for 2 h. For P-LISA, primary antibodies HA.11 (BabCo, 1:500) and FL393 (Santa Cruz, 1:1000) were diluted in PBS/EDTA/0.2% Triton X-100/2% NGS and incubated at 4° C. overnight. Following washes with TBS/ 0.05% Tween-20, a proximity ligation in situ assay (P-LISA) was performed according to the manufacturer's protocol (Detection Kit 613, OLink Bioscience) with the following exception: goat anti-rabbit (minus) and anti-mouse (plus) P-LISA probes were diluted in NGS at 1:10 instead of 1:5. Coverslips were mounted on microscope slides and images acquired using OpenLab software (Improvision) and a Zeiss Axioplan 2 microscope. Nuclear foci (at least 100 cells per treatment) were quantified using Blobfinder software (Centre for Image Analysis, Uppsala University, Sweden). All exposure times and intensity thresholds were set based on doxycycline/Nutlin-3 co-treatment and kept constant for each treatment. The statistical significance of the observed differences in foci number among the treatment conditions was determined using the unpaired t-test with Welch's correction. For standard immunofluorescence imaging of p53 and HDMX, the antibodies indicated above were again employed but following the PBS washes, the slides were incubated (1 h, room temperature) with goat anti-rabbit AF568 (1:1000) and goat anti-mouse AF488 (1:500) (Invitrogen/Molecular Probes) containing 1 µg/mL Hoechst. Density slices from each Hoechst image were generated in OpenLab, and used as masks to quantify the nuclear intensity of both p53 and HDMX. Total intensity was defined as average pixel intensity x nuclear area, and was corrected for nuclear size differences. Graphical representation and statistical analyses were performed using Microsoft Excel and Prism software (GraphPad). Cellular Penetrability Assays: To measure the cell penetrability of peptides or crosslinked polypeptides, intact cells are incubated with fluoresceinated crosslinked polypeptides (10 µM) for 4 hrs in serum-free media or in media supplemented with human serum at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KineticScan® HCS Reader.

Cellular Efficacy Assays:

The efficacy of certain crosslinked polypeptides is determined, for example, in cell-based killing assays using a variety of tumorigenic and non-tumorigenic cell lines and primary cells derived from human or mouse cell populations. Cell viability is monitored, for example, over 24-96 hrs of incubation with crosslinked polypeptides (0.5 to 50 µM) to identify those that kill at EC50<10 µM. Several standard assays that measure cell viability are commercially available and are optionally used to assess the efficacy of the crosslinked polypeptides. In addition, assays that measure Annexin V and caspase activation are optionally used to assess whether the crosslinked polypeptides kill cells by activating the apoptotic machinery. For example, the Cell Titer-Glo™ assay is used which determines cell viability as a function of intracellular ATP concentration.

In Vivo Stability Assays:

To investigate the in vivo stability of crosslinked polypeptides, the compounds are, for example, administered to mice and/or rats by IV, IP, PO or inhalation routes at concentrations ranging from 0.1 to 50 mg/kg and blood specimens withdrawn at 0', 5', 15', 30', 1 hr, 4 hrs, 8 hrs and 24 hours post-injection. Levels of intact compound in 25 µL of fresh serum are then measured by LC-MS/MS as above.

In Vivo Efficacy in Animal Models:

To determine the anti-oncogenic activity of crosslinked polypeptides of the invention in vivo, the compounds are, for example, given alone (IP, IV, PO, by inhalation or nasal routes) or in combination with sub-optimal doses of relevant chemotherapy (e.g., cyclophosphamide, doxorubicin, etoposide). Leukemia can be monitored, for example, by injecting mice with D-luciferin (60 mg/kg) and imaging the anesthetized animals (e.g., Xenogen In Vivo Imaging System, Caliper Life Sciences, Hopkinton, Mass.). Total body bioluminescence is quantified by integration of photonic flux (photons/sec) by Living Image Software (Caliper Life Sciences, Hopkinton, Mass.). Peptidomimetic macrocycles alone or in combination with sub-optimal doses of relevant chemotherapeutics agents are, for example, administered to leukemic mice (10 days after injection/day 1 of experiment, in bioluminescence range of 14-16) by tail vein or IP routes at doses ranging from 0.1 mg/kg to 50 mg/kg for 7 to 21 days. Optionally, the mice are imaged throughout the experiment every other day and survival monitored daily for the duration of the experiment. Expired mice are optionally subjected to necropsy at the end of the experiment. Another animal model is implantation into NOD-SCID mice of DoHH2, a cell line derived from human follicular lymphoma, that stably expresses luciferase. Another animal model is implantation into NOD-SCID-IL2Rγnull (NSG) mice of Luc-JEG-3, a cell line derived from human choriocarcinoma that stably expresses luciferase These in vivo tests optionally generate preliminary pharmacokinetic, pharmacodynamic and toxicology data.

Clinical Trials:

To determine the suitability of the crosslinked polypeptides of the invention for treatment of humans, clinical trials can be performed. For example, patients diagnosed with cancer and in need of treatment are selected and separated in treatment and one or more control groups, wherein the treatment group is administered a crosslinked polypeptide of the invention, while the control groups receive a placebo or a known anti-cancer drug. The treatment safety and efficacy of the crosslinked polypeptides of the invention can thus be evaluated by performing comparisons of the patient groups with respect to factors such as survival and quality-of-life. In this example, the patient group treated with a crosslinked polypeptide show improved long-term survival compared to a patient control group treated with a placebo.

In some embodiments, the HDMX modulating agent can include one or more of the small molecules disclosed by Reed et al., J. Biol. Chem., 285:10786-10796 (2010), which is hereby incorporated by reference in its entirety. For example, a HDMX modulating agent can include the small molecule SJ-172550 disclosed by Reed et al., J. Biol. Chem., 285:10786-10796 (2010).

In some embodiments, the HDMX modulating agent can include one or more of the $3_{14}$-helical β-peptides disclosed by Harker et al., Bioorg. Med. Chem., 17:2038-2046 (2009), which reference is hereby incorporated in its entirety. For example, an HDMX modulating agent can include the $β^3$-peptide β53-12 disclosed by Harker et al., Bioorg. Med. Chem., 17:2038-2046 (2009).

In some embodiments, the HDMX modulating agent can include one or more of the N-acylpolyamines (NAPAs) disclosed by Hayashi et al., Bioorg. Med. Chem., 17:7884-7893 (2009), which reference is hereby incorporated in its entirety. For example, a HDMX modulating agent can include NAPA25 disclosed by Hayashi et al., Bioorg. Med. Chem., 17:7884-7893 (2009).

In some embodiments, the HDMX modulating agent can include one or more of the modified scorpion toxin miniature protein disclosed Li et al., J. Am. Chem. Soc., 130: 13546-13548 (2008), which reference is hereby incorporated in its entirety. For example, a HDMX modulating agent can include stoppin-1 disclosed by Li et al., J. Am. Chem. Soc., 130:13546-13548 (2008).

In some embodiments, the HDMX modulating agent can include one or more of thioredoxin-conjugated peptides disclosed by Hu et al., Cancer Res., 67:8810-8817 (2007); Kallen et al., J. Biol. Chem., 284:8812-8821 (2009), which references are hereby incorporated in their entireties. For example, a HDMX modulating agent can include the pDI peptide disclosed by Phan et al., J. Biol. Chem., 285:2174-2183 (2010).

In some embodiments, the HDMX modulating agent can include one or more microRNAs (miRNAs) disclosed by Markey, et al Oncogene, 1-10 (2008), which reference is hereby incorporated in its entirety. For example, a HDMX modulating agent can include the miRNA miR-34a disclosed by Markey, et al Oncogene, 1-10 (2008).

HDM2 Modulating Agents

HDM2 modulating agents encompassed by the present disclosure include any agents that increase the expression, levels and/or activity of p53 in a cell by directly (e.g., by binding HDM2) or indirectly (e.g., by acting on a molecule or pathway that regulates HDM2 expression and/or activity) modulating (e.g., inhibit) the activity (e.g., the E3 ubiquitin ligase activity), expression (e.g., protein or mRNA expression) and/or levels (e.g., protein levels) of HDM2 in a cell.

In some embodiments, a HDM2 agent can include one or more of the agents disclosed below. For example, a HDM2 agent can include: (1) one or more non-stapled peptides that bind to HDM2; (2) one or more stapled p53 peptides that bind to HDM2; (3) one or more small molecules that that bind to HDM2; (4) one or more antibodies or antibody fragments that bind (e.g., bind specifically to) HDM2; (5) one or more nucleic acid molecules (e.g., inhibitory nucleic acid molecules (e.g., RNAi or siRNA) that reduce HDM2 expression; (6) one or more pharmaceuticals that that reduce the expression and/or activity of HDM2; and (7) one or more methods that that reduce the expression and/or activity of HDM2, and any combination of (1), (2), (3), (4), (5), (6) and/or (7).

In some embodiments, a HDM2 modulating agent used in the methods and compositions disclosed herein: is not the same as a HDMX modulating agent disclosed herein (e.g., the HDM2 agent binds specifically to HDM2 without binding (e.g., substantially binding) to HDMX).

In some embodiments, a HDM2 modulating agent can bind to HDM2 and HDMX. In such embodiments, however, the HDMX inhibitor will generally have a higher binding affinity for HDM2 than for HDMX (for example, the binding affinity of the HDM2 modulating agent can be 2, 5, 10, 20, 25, 50, 75, 100-fold or more for HDM2 than for HDMX).

In some embodiments, the HDM2 modulating agent can bind to both HDM2 and HDMX, but only inhibit (e.g., substantially inhibit) the activity of HDM2.

In some embodiments, a HDM2 agent can include one or more of the peptides or stapled peptides disclosed herein so long as the peptide or stapled peptide binds to and/or modulates HDM2 (methods for assessing whether an agent modulates HDM2 expression or activity are known in the art (see, e.g., U.S. patent application Ser. No. 12/525,123, which is hereby incorporated by reference).

In some embodiments, a HDM2 modulating agent used in the methods and compositions disclosed herein: is not the same as a HDMX modulating agent used in the methods and compositions disclosed herein (e.g., the HDM2 agent binds specifically to HDM2 without binding (e.g., substantially binding) to HDMX), or is the same as a HDMX modulating agent used in the methods and compositions disclosed herein, but has a higher binding affinity for HDM2 than for HDMX (for example, the binding affinity of the HDMX modulating agent can be 1, 2, 5, 10, 20, 25, 50, 75, 100-fold or more for HDM2 than for HDMX).

In some embodiments, the HDM2 modulating agent is not a cross-linked peptide. In some embodiments, the HDM2 modulating agent is not a cross-linked peptide shown in FIG. 1C. In some embodiments, the HDM2 modulating agent is not SAH-p53-8

In some embodiments, the HDM2 modulating agent can include Nutlin-3a (e.g., $C_{30}H_{30}C_1N_4O_4$; molecular weight: 581.4896 [g/mol] (two and three-dimensional structures are shown at world wide web address pubchem.ncbi.nlm.nih-.gov/summary/summary.cgi?cid=216345 for) (F. Hoffmann-La Roche Ltd) (see Arya et al., British J. Cancer, 103:186-195 (2010); Laurie et al. Nature, 444:61-66 (2006): reports that Nutlin-3 binds to HDM2 and HDMX, but binds to HDM2 with higher affinity than HDMX;), e.g., commercially available Nutlin-3 or Nutlin-3a.

In some embodiments, the HDM2 modulating agent can include one or more spiro-oxindoles disclosed by Shangary et al. (Proc. Nat. Acad. Sci. 105:3933-3938 (2008), which is hereby incorporated by reference in its entirety). In some embodiments, the HDM2 modulating agent can include the spiro-oxindoles disclosed by Ding et al. (J. Am. Chem. Soc. 127:10130-10131 (2005)), which is hereby incorporated by reference in its entirety).

In some embodiments, the HDM2 modulating agent can include one or more benzodiazepinediones disclosed by Grasberger et al. (J. Med. Chem. 48:909-912 (2005)), which is hereby incorporated by reference in its entirety).

In some embodiments, the HDM2 modulating agent can include one or more terphenyl-based helical mimetics disclosed by Yin et al. (Angew. Chem. Int. Ed. 44:2704-2707 (2005)), which is hereby incorporated by reference in its entirety.

In some embodiments, the HDM2 modulating agent can include antibodies that bind to (e.g., bind specifically to) HDM2 (e.g., monoclonal or polyclonal antibodies or antigen binding fragments of a monoclonal or polyclonal antibody that binds to (e.g., binds specifically to) HDM2. In some embodiments, the HDM2 modulating agent can include the monoclonal antibody MDM2-F4-14 disclosed by Anderson et al. (International J. Oncology, 31:545-555 (2007), which is hereby incorporated by reference in its entirety).

In some embodiments, the HDM2 modulating agent includes one or more 'miniature proteins' disclosed by Kritzer et al. (ChemBioChem, 7:29-31 (2006), which is hereby incorporated by reference in its entirety). In some embodiments, the HDM2 modulating agent can include the miniature peptide p53AD$_{15-31}$ disclosed by Kritzer et al. (ChemBioChem, 7:29-31 (2006)).

In some embodiments, the HDM2 modulating agent includes one or more microRNAs (miRNAs) disclosed by Pichiorri, et al Cancer Cell, 18:367-381 (2010), which is hereby incorporated by reference in its entirety. For example, a HDM2 modulating agent can include the miRNA miR-192 disclosed by Pichiorri, et al Cancer Cell, 18:367-381 (2010).

Compositions and/or Methods for Inducing p53 Expression and/or Activity

As noted above, any combination of a HDMX modulating agent or a HDMX modulating agent in combination with a HDM2 modulating agent can be used in combination with a composition and/or method for inducing p53 expression and/or activity. Exemplary compositions and/or methods for inducing p53 expression and/or activity can include, but are not limited to, ionizing radiation, ultraviolet light, DNA damaging agents such as etoposide, actinomycin D, doxorubicin, paclitaxel, and other chemotherapeutic agents.

In some embodiments, p53 activity in a cell can be increased by introducing active p53 into a cell (e.g., using viruses (e.g., retroviruses) and/or DNA transduction). In some embodiments, the active p53 can be expressed from a nucleic acid sequence obtained from the subject and/or the active p53 can be an isolated protein obtained from the subject and optionally coupled to a moiety that increases cell penetrability of the p53. In some embodiments, p53 activity can be increased by retroviral reconstruction of p53 in a targeted fashion in cancer cells (e.g., cancer cells with diminished p53 activity).

In some embodiments, a composition and/or method for inducing p53 expression and/or activity can include one or more HDM2 inhibitors disclosed herein.

As used herein, the term "expression" includes protein and/or nucleic acid expression and/or protein activity.

Pharmaceutical Compositions

In some embodiments, compositions including pharmaceutical compositions, disclosed herein can include: (1) one or more HDMX modulating agents; and/or (2) one or more HDM2 modulating agents; and/or (3) one or more compositions and/or methods for inducing p53 expression and/or activity, including any combination of (1)-(3), e.g., any combination of (1) with (2) and/or (3) (e.g., (1) and (2), (1) and (3), and (1), and (2), and (3)).

Furthermore, the methods disclosed herein include the use of any of these compositions, e.g., as compositions or pharmaceutical compositions.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound or agent disclosed herein which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include alkali metal (e.g., sodium), alkaline earth metal (e.g., magnesium), ammonium and N-(alkyl)4+ salts. This invention also envisions the quaternization of any basic nitrogen-containing groups of the compounds disclosed herein. Water or oil-soluble or dispersible products may be obtained by such quaternization.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.001 to about 100 mg/kg of body weight, or according to the requirements of the particular drug. Alternatively or in addition, the present invention may be administered according to any of the Food and Drug Administration approved methods, for example, as described in CDER Data Standards Manual, version number 004 (which is available at fda.give/cder/dsm/DRG/drg00301.htm).

The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

In some embodiments, an effective dose of a HDMX modulating agent (e.g., a p53 stapled peptide) can include, but is not limited to, for example, about, 0.00001, 0.0001, 0.001, 0.01, 0.1, 1 or 10-10000; 0.00001, 0.0001, 0.001, 0.01, 0.1, 1 or 10-5000; 0.00001, 0.0001, 0.001, 0.01, 0.1, 1 or 10-2500; 0.00001, 0.0001, 0.001, 0.01, 0.1, 1 or 10-1000; 0.00001, 0.0001, 0.001, 0.01, 0.1, 1 or 10-900; 0.00001, 0.0001, 0.001, 0.01, 0.1, 1 or 10-800; 0.00001, 0.0001, 0.001, 0.01, 0.1, 1 or 10-700; 0.00001, 0.0001, 0.001, 0.01, 0.1, 1 or 10-600; 0.00001, 0.0001, 0.001, 0.01, 0.1, 1 or 10-500; 0.00001, 0.0001, 0.001, 0.01, 0.1, 1 or 10-400; 0.00001, 0.0001, 0.001, 0.01, 0.1, 1 or 10-300; 0.00001, 0.0001, 0.001, 0.01, 0.1, 1 or 10-200; 0.00001, 0.0001, 0.001, 0.01, 0.1, 1 or 10-100; 0.00001, 0.0001, 0.001, 0.01, 0.1, 1 or 10-90; 0.00001, 0.0001, 0.001, 0.01, 0.1, 1 or 10-80; 0.00001, 0.0001, 0.001, 0.01, 0.1, 1 or 10-70; 0.00001, 0.0001, 0.001, 0.01, 0.1, 1 or 10-60; 0.00001, 0.0001, 0.001, 0.01, 0.1, 1 or 10-50; 0.00001, 0.0001, 0.001, 0.01, 0.1, 1 or 10-40; 0.00001, 0.0001, 0.001, 0.01, 0.1, 1 or 10-30; 0.00001, 0.0001, 0.001, 0.01, 0.1, 1 or 10-20; 0.00001, 0.0001, 0.001, 0.01, 0.1, 1 or 10-30; 0.00001, 0.0001, 0.001, 0.01, 0.1, 1-15, 0.00001, 0.0001, 0.001, 0.01, 0.1, 1 or 10-30; 0.00001, 0.0001, 0.001, 0.01, 0.1, 1-10, 0.00001, 0.0001, 0.001, 0.01, 0.1, 1 or 10-30; or 0.00001, 0.0001, 0.001, 0.01, 0.1, 1-5 mg/kg/day, e.g., administered intravenously.

In some embodiments, an effective dose of SAH-p53-8 can include, but is not limited to, for example, about, 0.00001, 0.0001, 0.001, 0.01, 0.1, 1 or 10-10000; 0.00001, 0.0001, 0.001, 0.01, 0.1, 1 or 10-5000; 0.00001, 0.0001, 0.001, 0.01, 0.1, 1 or 10-2500; 0.00001, 0.0001, 0.001, 0.01, 0.1, 1 or 10-1000; 0.00001, 0.0001, 0.001, 0.01, 0.1, 1 or 10-900; 0.00001, 0.0001, 0.001, 0.01, 0.1, 1 or 10-800; 0.00001, 0.0001, 0.001, 0.01, 0.1, 1 or 10-700; 0.00001, 0.0001, 0.001, 0.01, 0.1, 1 or 10-600; 0.00001, 0.0001, 0.001, 0.01, 0.1, 1 or 10-500; 0.00001, 0.0001, 0.001, 0.01, 0.1, 1 or 10-400; 0.00001, 0.0001, 0.001, 0.01, 0.1, 1 or 10-300; 0.00001, 0.0001, 0.001, 0.01, 0.1, 1 or 10-200; 0.00001, 0.0001, 0.001, 0.01, 0.1, 1 or 10-100; 0.00001, 0.0001, 0.001, 0.01, 0.1, 1 or 10-90; 0.00001, 0.0001, 0.001, 0.01, 0.1, 1 or 10-80; 0.00001, 0.0001, 0.001, 0.01, 0.1, 1 or 10-70; 0.00001, 0.0001, 0.001, 0.01, 0.1, 1 or 10-60; 0.00001, 0.0001, 0.001, 0.01, 0.1, 1 or 10-50; 0.00001, 0.0001, 0.001, 0.01, 0.1, 1 or 10-40; 0.00001, 0.0001, 0.001, 0.01, 0.1, 1 or 10-30; 0.00001, 0.0001, 0.001, 0.01, 0.1, 1 or 10-20; 0.00001, 0.0001, 0.001, 0.01, 0.1, 1 or 10-30; 0.00001, 0.0001, 0.001, 0.01, 0.1, 1-15, 0.00001, 0.0001, 0.001, 0.01, 0.1, 1 or 10-30; 0.00001, 0.0001, 0.001, 0.01, 0.1, 1-10, 0.00001, 0.0001, 0.001, 0.01, 0.1, 1 or 10-30; or 0.00001, 0.0001, 0.001, 0.01, 0.1, 1-5 mg/kg/day, e.g., administered intravenously.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the formulae described herein or a pharmaceutically acceptable salt thereof; an additional agent including for example, morphine or codeine; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. The compositions delineated herein include the compounds of the formulae delineated herein, as well as additional therapeutic agents if present, in amounts effective for achieving a modulation of disease or disease symptoms.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra¬articular, intraarterial, intrasynovial, intrasternal, intrathecal, intralesional and intracranial injection or infusion techniques. Alternatively or in addition, the present invention may be administered according to any of the Food and Drug Administration approved methods, for example, as described in CDER Data Standards Manual, version number 004 (which is available at fda.give/cder/dsm/DRG/drg00301.htm).

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome.

Effective amounts of one or more compounds or a pharmaceutical composition for use in the present invention include amounts that promote increased p53 levels (e.g., protein levels) and/or p53 activity (e.g., biological activity) in a cell. A therapeutically effective amount of a compound is not required to cure a disease but will provide a treatment for a disease.

In some embodiments, the present disclosure provides methods for using any one or more of the compositions (indicated below as 'X') disclosed herein in the following methods:

Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

Methods of Treatment/Personalized Medicine

The present disclosure includes treatment methods for cancer, e.g., methods for treating cancer in a subject (e.g., a human subject). As used herein, "treatment" means any manner in which one or more of the symptoms of a disease or disorder (e.g., cancer) are ameliorated or otherwise beneficially altered. As used herein, amelioration of the symptoms of a particular disorder (e.g., cancer) refers to any lessening, whether permanent or temporary, lasting or transient that can be attributed to or associated with treatment by the compositions and methods of the present invention. In some embodiments, treatment can promote or result in, for example, a decrease in the number of cancer cells (e.g., in a subject) relative to the number of cancer cells (e.g., in the subject) prior to treatment; a decrease in the viability (e.g., the average/mean viability) of cancer cell(s) (e.g., in a subject) relative to the viability (e.g., the average/mean viability) of cancer cell(s) (e.g., in the subject) prior to treatment; a reduction in tumor size relative to tumor size prior to treatment; and/or reductions in one or more symptoms associated with one or more cancers in a subject relative to the subject's symptoms prior to treatment.

In some embodiments, the methods can include selecting a subject in need of treatment (e.g., a subject at risk for, that has, or that is suffering from, one or more cancers) and administering to the subject an effective dose of one or more of: (1) one or more HDMX modulating agents; (2) one or more HDM2 modulating agents; and (3) one or more compositions and/or methods for inducing p53 expression and/or activity, including any combination of (1) with (2) and (3) (e.g., (1) and (2); (1) and (3); and (1), and (2), and (3)) under conditions and for a period of time sufficient to treat the subject. Such methods can also include monitoring or evaluating the subject during and after administration of the composition to determine the efficacy of the treatment, and, if necessary, adjusting treatment (e.g., by altering the composition, by increasing the dose of a single administration of the composition, by increasing the number of doses of the composition administered per day, and/or by increasing the number of days the composition is administered) to improve efficacy.

In some embodiments, the methods can include developing a personalized treatment regimen for a subject with cancer. Such methods can include, for example, identifying a subject with cancer cells that are sensitive to HDM2 modulating agents and treating the subject with one or more HDM2 modulating agents; identifying a subject with cancer cells that are sensitive to HDMX modulating agents and treating the subject with one or more HDMX modulating agents; and identifying a subject with cancer cells that are resistant to HDM2 modulating agents and/or HDMX modulating agents and treating the subject with a synergistic combination of one or more HDMX modulating agents and one or more HDM2 modulating agents (see FIGS. 11 and 12). In some embodiments, the methods can include determining the most appropriate treatment for a subject confirmed to have cancer (e.g., by determining the susceptibility of one or more of the subject's cancer cells to treatment using the compositions disclosed herein (e.g., in vitro)), developing a treatment regimen for the subject, and optionally administering to the subject a composition in accordance with the treatment regimen. These methods can include, for example:

(i) selecting a subject having cancer; evaluating (e.g., detecting) the expression and/or activity of p53 in the subject's cancer (e.g., in a cancer cell obtained from the subject (e.g., obtained by biopsy); and, if p53 expression and/or activity is detected, providing the subject with a personalized treatment regimen that includes administering an effective amount of one or more HDMX modulating agents to the subject. In some embodiments, the method includes administering the one or more HDMX modulating agents to the subject under conditions and for a period of time sufficient to treat the subject;

(ii) selecting a subject having cancer; detecting the presence and/or level of a p53-HDMX complex in a sample (e.g., a cancer cell) obtained from the subject (e.g., a cancer cell obtained by biopsy); and, if the p53-HDMX complex is detected, providing the subject with a personalized treatment regimen that includes administering an effective amount of one or more HDMX modulating agents to the subject. In some embodiments, the method includes administering the one or more HDMX modulating agents to the subject under conditions and for a period of time sufficient to treat the subject;

(iii) selecting a subject having cancer; detecting the presence and/or level of a p53-HDMX complex in a sample (e.g., a cancer cell) obtained from the subject (e.g., a cancer cell obtained by biopsy); and, if the p53-HDMX complex is detected administering the one or more HDMX modulating agents to the subject under conditions and for a period of time sufficient to treat the subject; monitoring or evaluating the subject during and after administration of the composition to determine the efficacy of the treatment: and, if the efficacy of the treatment is low, administering to the subject one or more modulators of HDM2;

(iv) selecting a subject having cancer; detecting the presence and/or level of a p53-HDMX complex in a sample (e.g., a cancer cell) obtained from the subject (e.g., a cancer cell obtained by biopsy) and assessing the level of p53 in the sample to determine if the level or activity of p53 is low (e.g., relative to the level or activity of p53 in a cancer cell that exhibits reduced viability when contacted with one or more HDMX modulating agents. In some embodiments the level of p53 is compared to the level of p53 in a JEG-3 and/or MCF-7 cell or cells. In some embodiments, activity can be assessed by titrating dissociation of HDMX-p53 complexes, as described herein); and, if the p53-HDMX complex is detected and the level of p53 is low, providing the subject with a personalized treatment regimen that includes administering an effective amount of one or more HDMX modulating agents and one or more HDM2 modulating agents to the subject. In some embodiments, the methods can also include providing the subject with a personalized treatment regimen that further includes administering an effective amount of a composition and/or method for inducing p53 expression and/or activity. In some embodiments, the method includes administering the one or more HDMX modulating agents and the one or more HDM2 modulating agents and, optionally, the composition and/or method for inducing p53 expression and/or activity to the subject under conditions and for a period of time sufficient to treat the subject;

(v) selecting a subject with cancer that has previously received one or more HDM2 modulating agents (e.g., Nutlin-3), but whose cancer cells were resistant (e.g., partially resistant) to the HDM2 modulating agents (e.g., Nutli-3); and providing the subject with a personalized treatment regimen that includes administering an effective amount of one or more HDMX modulating agents and one or more HDM2 modulating agents and, optionally, a composition and/or method for inducing p53 expression and/or activity. In some embodiments, the method includes administering the one or more HDMX modulating agents and the one or more HDM2 modulating agents and, optionally, the composition for inducing p53 expression and/or activity to the subject under conditions and for a period of time sufficient to treat the subject; and/or (vi) selecting a subject with cancer that has previously received one or more HDMX modulating agents (e.g., SAH-p53-8), but whose cancer cells were resistant (e.g., partially resistant) to the HDMX modulating agents; and providing the subject with a personalized treatment regimen that includes administering an effective amount of one or more HDMX modulating agents and one or more HDM2 modulating agents and, optionally, a composition for inducing p53 expression and/or activity. In some embodiments, the method includes administering the one or more HDMX modulating agents and the one or more HDM2 modulating agents and, optionally, the composition for inducing p53 expression and/or activity to the subject under conditions and for a period of time sufficient to treat the subject.

It should be noted that methods (i)-(vi) can be performed independently or together and in any order. Any of methods (i)-(vi) can also include monitoring or evaluating the subject during and after administration of the composition to determine the efficacy of the treatment, and, if necessary, adjusting treatment (e.g., by altering the composition, by increasing the dose of a single administration of the composition, by increasing the number of doses of the composition administered per day, and/or by increasing the number of days the composition is administered) to improve efficacy.

In some embodiments, HDMX modulating compositions and methods herein can be used in the treatment of a subject in combination with other anti-cancer therapies or therapeutic methods. For example, HDMX modulating compositions and methods herein can be used in combination with chemotherapy, radiotherapy, and antibody therapy.

In some embodiments, the present disclosure includes compositions and methods for treating a subject at risk for developing radiation-induced gastrointestinal syndrome (see, e.g., Kirsch et al., Science, 327:593-596 (2010) for a review). Acute exposure to ionizing radiation can cause lethal damage to the gastrointestinal (GI) tract leading to a condition known as GI syndrome. Overexpression of p53, e.g., in epithelial cells of the GI tract protects the GI against damage caused by acute ionizing radiation (Kirsch et al. (2010).

Accordingly, in some embodiments, the present disclosure includes selecting a subject scheduled to receive radiation therapy (e.g., ionizing radiation therapy) and developing a treatment regimen for the subject. The treatment regimen can include treating (e.g., administering) the subject with an effective dose of one or more HDMX modulating agents (e.g., SAH-p53-8) and/or an effective dose of one or more HDM2 modulating agents (e.g., Nutlin-3) prior to (e.g., immediately prior to, one day before, more than one day before, one week before, more than one week before) being exposed to radiation (e.g., ionizing radiation). In some embodiments, the subject can be treated with a single dose or multiple doses of one or more HDMX modulating agents (e.g., SAH-p53-8) and/or one or more HDM2 modulating agents (e.g., Nutlin-3) prior to (e.g., immediately prior to, one day before, more than one day before, one week before, more than one week before) being exposed to radiation (e.g., ionizing radiation). In some embodiments, the dose/doses is/are administered systemically. Alternatively or in addition, the dose/doses is/are administered locally (e.g., locally to the GI or to the GI epithelial cells in the GI). In some embodiments, the treatment includes an effective dose of one or more HDMX modulating agents (e.g., SAH-p53-8). In some embodiments, the treatment includes an effective dose of one or more HDM2 modulating agents (e.g., Nutlin-3). In some embodiments, the treatment includes an synergistic dose of one or more HDMX modulating agents (e.g., SAH-p53-8) and one or more HDM2 modulating agents (e.g., Nutlin-3). The methods can also include monitoring or evaluating the subject during and after treatment to determine the efficacy of the treatment, and, if necessary, adjusting treatment, e.g., prior to further radiation therapy (e.g., by altering the composition, by increasing the dose of a single administration of the composition, by increasing the number of doses of the composition administered per day, and/or by increasing the number of days the composition is administered) to improve efficacy of the treatment. These methods can also include administering one or more HDMX modulating agents and/or one or more HDM2 modulating agents to a subject in combination with radiation therapy.

Subject Selection

The term "subject" is used throughout the specification to describe an animal, human or non-human, to whom treatment according to the methods of the present invention is provided.

As used herein, the terms "cancer", "hyperproliferative" and "neoplastic" refer to cells having the capacity for autonomous growth, i.e., an abnormal state or condition characterized by rapidly proliferating cell growth. As described herein, the present methods can be used to treat any cancer cell capable of expressing functional p53. For example, any cancer cell in which functional p53 is expressed but wherein the levels or activity of p53 are reduced in the cell by HDMX and/or HDMX can be beneficially treated using the compositions and methods disclosed herein. Wild type p53 activity is not required. For example, cells which express mutant p53 that retains some function can be beneficially treated.

Accordingly, the present disclosure can include: (1) identifying a subject with cancer; and (2) determining if the subject's cancer cells encode or express functional p53; and (3) treating the subject or developing a treatment for the subject if the subject's cancer cells express functional p53 using the compositions and methods disclosed herein. For example, p53 function can be assessed in any of the cancers below.

In some instances, a subject or a cell from a subject should be capable of expressing functional p53. Such functional p53 should have some p53 function but does not have to have the same level of function as wild type p53. Accordingly, functional p53 can include mutated p53 that retains some level of function. In some instances, functional p53 can have 1%, 2%, 5%, 10%, 20%, 30%, 40%, 50%, 60%, 70%, 80%, 90%, 95%, or more of the functional activity of wild type p53 (e.g., wild type p53 in a non-cancer cell from the same subject). In some embodiments, a cell may be capable of expressing functional p53 but functional p53 is not detectable (for example, functional p53 is expressed but rapidly degraded in the cell). Such cells can be identified by detecting that the cell encodes functional p53. Such methods can be performed, for example, using e.g., DNA probes and/or by detecting p53 mRNA in the cell or a sample therefrom.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991), Crit. Rev. Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

Methods for identifying a subject at risk for developing and/or with cancer are known in the art. For example, methods for identifying a subject at risk for developing cancer (e.g., a subject with an increased likelihood for developing cancer) are known in the art (see, e.g., U.S. Pat. No. 7,611,870 and Jie Li et al., Nature, Identification of high-quality cancer prognostic markers and metastasis network modules (2010)). Exemplary methods for identifying a subject with cancer are also known in the art and include self-evaluation, clinical evaluation (including physical examination and biopsy), laboratory analysis (e.g., biomarker analysis), the Papanicolaou test (Pap smear), and imaging methods (e.g., mammography, MRI, PET and/or CT scan and angiogram). In some embodiments, the p53-HDMX biomarker disclosed herein is used to identify a subject with cancer (e.g., cancer that is susceptible to treatment with a HDMX modulating agent).

As used herein, p53 activity can include, but is not limited, for example, p53 transcriptional activity (which can be assessed, e.g., by monitoring the transcription, mRNA levels, or protein levels of a target of p53, e.g., a p53 transcriptional target. Suitable p53 transcriptional targets are known in the art and include, but are not limited to, e.g., SFN, GADD45A, CRYZ, S100A2, BTG2, ODC1, TP5313, TGFA, PCBP4, PLK2, CDC25C, CCNG1, IER3, TAP1, CDKN1A, EEF1A1, THBS2, ANLN, IGFBP3, EGFR, HGF, SERPINE1, MET, NOS3, TNFRSF10B, SCARA3, RRM2B, GML, DKK1, FAS, SCD, LRDD, CTSD, CD82, HSPA8, P53AIP1, SLC38A2, MDM2, HDM2, RB1, BDKRB2, MMP2, CX3CL1, SERPINB4, GDF15, BBC3, BAX, PCNA, TRPM2, and P2RXL1) and/or p53 functional activity (e.g., p53 protein-interaction based function, e.g., cell death (e.g., necrosis and apoptosis), and cell cycle arrest). p53 activity can also be assessed by determining p53 transcription, mRNA, or protein levels. Methods for carrying out each of these exemplary methods are well known in the art.

Kits

The compounds and pharmaceutical compositions described herein can be provided in a kit. For example, the kit can include compositions and methods for developing a personalized treatment method for a subject with cancer. In some embodiments, these kits can include compositions for detecting a biomarker of p53 in complex with HDMX (e.g., an antibody that binds specifically to the complex and/or components required to immunoprecipitate p53 or HDMX and to detect p53 or HDMX by immunoblotting (e.g., a kit can provide a first antibody (e.g., an anti-p53 antibody) to immunoprecipitate p53 and a second antibody (e.g., an anti-HDMX antibody) to detect HDMX by immunoblotting; or a kit can provide a first antibody (e.g., an anti-HDMX antibody) to immunoprecipitate HDMX and a second antibody (e.g., an anti-p53 antibody) to detect by immunoblotting). In some embodiments, the kit can further include compositions, including pharmaceutical compositions, that include: (1) one or more HDMX modulating agents (e.g., SAH-p53-8); and/or (2) one or more HDM2 modulating agents (e.g., Nutliln-3); and/or (3) one or more compositions and/or methods for inducing p53 expression and/or activity, including any combination of (1)-(3), e.g., any combination of (1) with (2) and/or (3) (e.g., (1) and (2), (1) and (3), and (1), and (2), and (3) for administering to the subject. In such instances, the compositions for administering to the subject can be personalized to the subject. Alternatively, the compositions for administering to the subject are not personalized. In some embodiments, the compositions and methods for developing a personalized treatment method and the compositions for administering to the subject are provided in separate and independent kits.

The kits can also include informational material relevant to the compositions and methods of using the compositions. The informational material can be descriptive, instructional, marketing or other material that relates to the methods described herein and/or to the use of the agent for the methods described herein. For example, the informational material relates to the use of the compound to treat a subject who has, or who is at risk for developing cancer. The kits can also include paraphernalia for administering one or more compounds to a cell (in culture or in vivo) and/or for administering a cell to a patient, and any combination of the methods described herein.

In one embodiment, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In another embodiment, the informational material can include instructions to administer the pharmaceutical composition to a suitable subject, e.g., a human, e.g., a human having, or at risk for developing cancer.

The informational material of the kits is not limited in its form. In many cases, the informational material (e.g., instructions) is provided in printed matter, such as in a printed text, drawing, and/or photograph, such as a label or printed sheet. However, the informational material can also be provided in other formats, such as Braille, computer readable material, video recording, or audio recording. Of course, the informational material can also be provided in any combination of formats.

In addition to the compound, the composition of the kit can include other ingredients, such as a solvent or buffer, a stabilizer, a preservative, and/or a second agent for treating a condition or disorder described herein. Alternatively, the other ingredients can be included in the kit, but in different compositions or containers than the compound. In such embodiments, the kit can include instructions for admixing the agent and the other ingredients, or for using one or more compounds together with the other ingredients.

The kit can include one or more containers for the pharmaceutical composition. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the pharmaceutical composition. For example, the kit can include a plurality of syringes, ampoules, foil packets, or blister packs, each containing a single unit dose of the pharmaceutical composition. The containers of the kits can be air tight and/or waterproof, and the containers can be labeled for a particular use. For example, a container can be labeled for use to treat a hearing disorder.

As noted above, the kits optionally include a device suitable for administration of the composition (e.g., a syringe, pipette, forceps, dropper, swab, or any such delivery device).

EXAMPLES

The invention is further described in the following examples, which do not limit the scope of the invention described in the claims.

Example 1

Design, Synthesis, and Characterization of p53 Stapled Peptides

To design SAH-p53 compounds, synthetic olefinic derivatives were placed at positions that avoid critical HDM2-binding residues. Hydrocarbon staples spanning the i, i+7 positions were generated by olefin metathesis, as shown in FIG. 1A.

Peptide synthesis, olefin metathesis, FITC derivatization, reverse phase HPLC purification, and amino acid analysis were performed as previously reported.

More specifically, the sequence of SAH-53-8, shown in FIG. 1B as SAH-p53-8, resulted from modification of the wild-type p53 transactivation domain amino acid sequence (amino acids 14-29 of SEQ ID NO:1), also shown in FIG. 1B as WT-p53$_{14-29}$. Briefly, amino acids at positions S20 and P27 were replaced with synthetic olefinic residues. The structurally reinforcing "hydrocarbon staple" was then generated by olefin metathesis according to the method described in Bird et al., (Methods Enzymol., 446:369-386 (2008)), which methods are hereby incorporated by reference, and illustrated in FIG. 1D. Additional residues not required for HDM2 interaction were also modified to improve peptide solubility and uptake as described by Bernal et al. (J. Am. Chem. Soc., 129:2456-2457 (2007)). SAH-p53-8 and the methods employed in the design and synthesis of SAH-p53-8 are described in Bernal et al. (J. Am. Chem. Soc., 129:2456-2457 (2007)), which disclosure is hereby incorporated by reference.

SAH-p53-8$_{F19}$ a control peptide, was generated by substituting amino acid F19 of SAH-p53-8 (an essential amino acid for HDM2 interaction (Bottger et al., J. Mol. Biol., 269:744-756 (1997)) with alanine SAH-p53-8$_{F19}$ serves as a negative control for the biological experiments described herein.

Figures 1C, 1D:
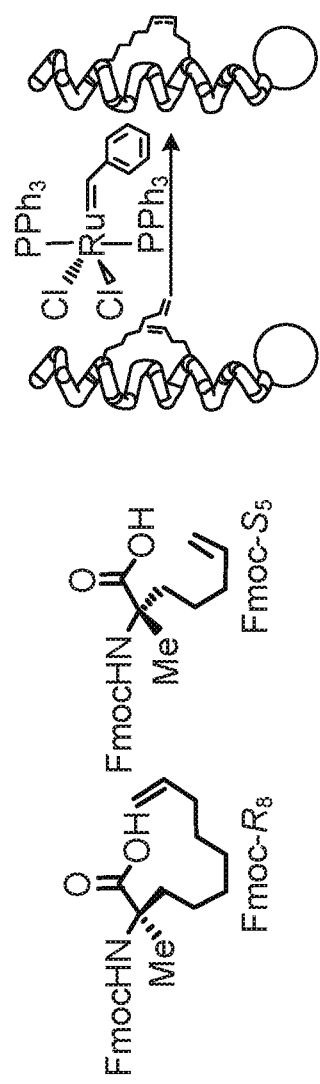
FIG. 1C is a table showing the sequence and other physical characteristics of SAH-p53-8 and other exemplary stapled p53 peptides (SEQ ID NOs:2-21).
FIG. 1D is a cartoon showing an exemplary method for stapling peptides.
Figure 1E:
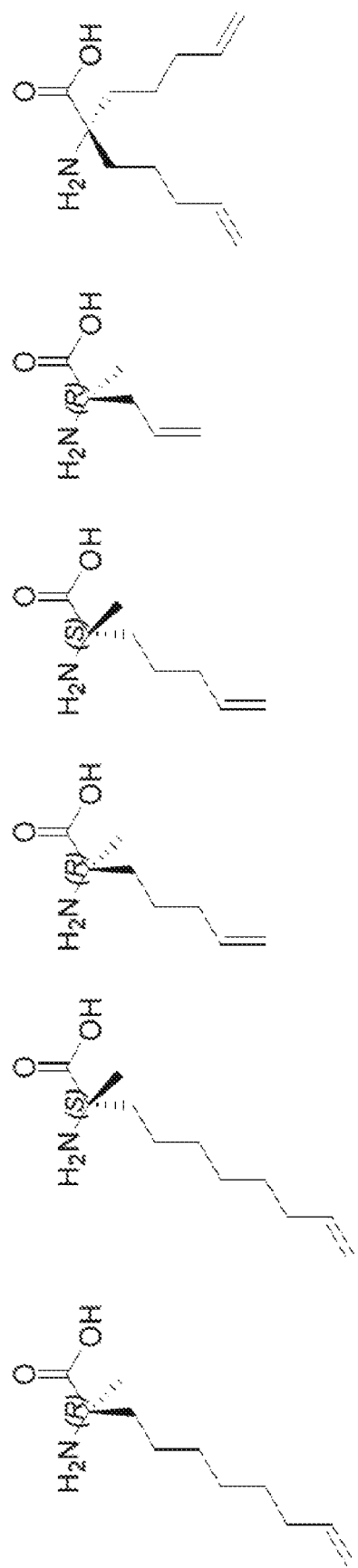
FIG. 1E shows a variety of non-natural amino acids containing olefinic tethers that can be used to generated hydrocarbon stapled p53 peptides.
Figure 1:
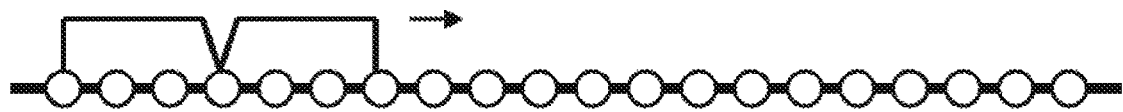
FIGS. 1Fa-1fd show a variety of single staple compositions spanning i, i+3; i, i+4, and i, i+7 positions and single staple scanning to generated a library of singly stapled p53 peptides.
FIGS. 1Ga-1Gh show a variety of staple compositions in multiply stapled peptides and staple scanning to generated a library of multiply stapled p53 peptides.
FIGS. 1HA-1HI shows a variety of staple compositions in tandem stapled peptides and staple scanning to generated a library of tandemly stapled p53 peptides.
Figure 1:
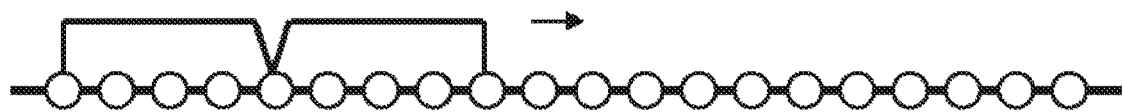
Figure 1:
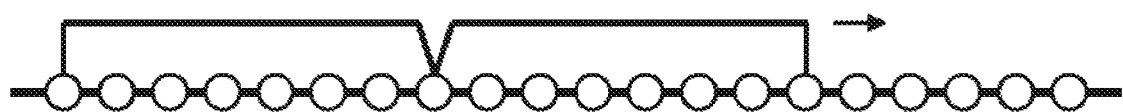
Figure 1:
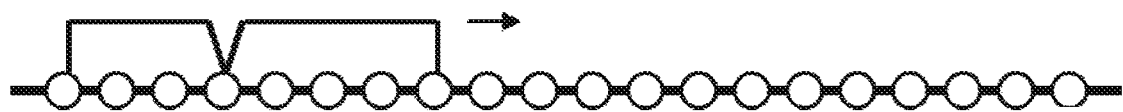
Figure 1:
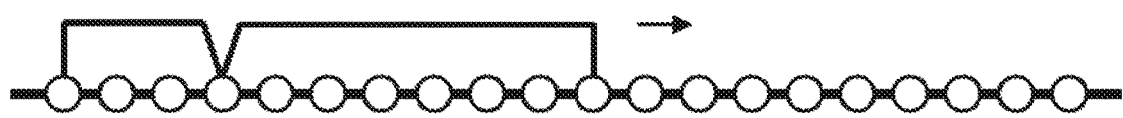
Figure 1:
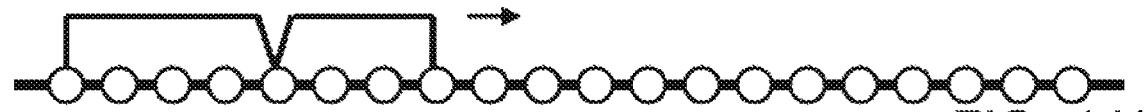
Figure 1:
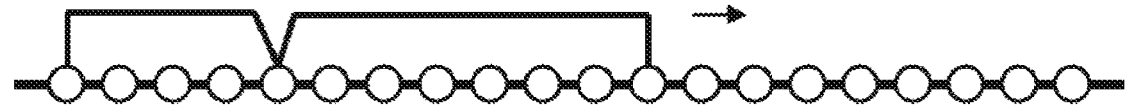
Figure 1:
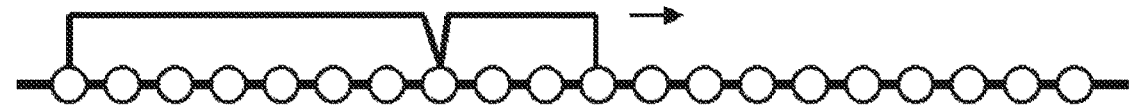
Figure 1:
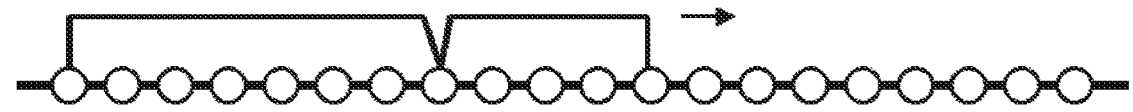

The sequence and other properties of these and other stapled p53 peptides are shown in FIG. 1C. The characteristics of these peptides were assessed. More specifically, to evaluate the structural impact of installing an all-hydrocarbon i, i+7 staple, circular dichroism (CD) experiments were performed to determine α-helicity.

As shown in FIG. 1C, while the wild type p53 peptide displayed 11% α-helical content in water at pH 7.0, SAH-p53s 1-4 demonstrated 10-59% α-helicity. SAH-p53-4 also demonstrated improved proteolytic stability. Also as shown in FIG. 1C, while generally negatively charged SAH-p53 compounds were incapable of penetrating intact Jurkat T-cells, SAH-p53-8 was cell permeable and was positively charged at physiological pH. Thus positive charge may be a characteristic feature or requirement for cell penetrating peptides.

SAH-p53-8 was generated by replacing aspartic and glutamic acids with asparagines and glutamines to adjust peptide charge and mutate select amino acids previously reported to participate in p53 nuclear export (L14Q) and potential ubiquitylation (K24R). These modifications resulted in stapled peptides that exhibited a 2-8.5 fold enhancement in α-helical content, retained high binding affinity for HDM2, and demonstrated time- and temperature-dependent cellular uptake by FACS and confocal microscopy. Cell viability assays using RKO or SJSA-1 cancer cells exposed to SAH-p53 peptides indicated that SAH-p53-8, which contained point mutations in both nuclear export and ubiquitylation sites, was structurally-stabilized, cell-permeable, and promoted cell death.

Example 2

SAH-p53-8 Binds to HDMX and HDM2

Interaction of SAH-p53-8 with HDMX was assessed using fluorescence polarization (FP) using full length HDMX and FITC-labeled stapled peptides, WT-p53$_{14-29}$, SAH-p53-8, and SAH-p53-8$_{F19A}$.

Recombinant HDM2 was generated as previously reported (Bernal et al., J. Am. Chem. Soc., 129:2456-2457 (2007)).

To generate recombinant HDMX, *Escherichia coli* BL21 (DE3) pLysS containing the plasmid encoding full-length HDMX with N-terminal thioredoxin, S, and hexahistidine tags, and an engineered TEV protease cleavage site (pET32-LIC vector, Novagen) were cultured in ampicillin- and chloramphenicol-containing Luria-Bertani broth and induced with 0.1 mM isopropyl β-D-thiogalactoside. Cells were harvested after 6 h by centrifugation for 20 min at 3200 rpm, resuspended in buffer A (20 mM Tris pH 8.0, 0.5 M NaCl) and lysed by sonication. Cellular debris was pelleted by centrifugation for 30 min at 15,000 rpm, and the supernatant was incubated with Ni-NTA agarose (Qiagen) for 2 hours. Resin was washed with buffer A and eluted with a gradient of imidazole ranging from 5 mM to 500 mM. The fractions containing the eluted protein were concentrated and treated overnight with recombinant TEV S219V protease (Kapust et al., Protein Eng., 14:993-1000 (2001)) at 4° C. The reaction was concentrated to 2 mL and purified by size exclusion chromatography using a G200 column. Purity of the protein was assessed by SDS-PAGE and its identity confirmed by MALDI-TOF mass spectrometry.

FP assays were performed as previously described (Bernal et al., J. Am. Chem. Soc., 129:2456-2457 (2007); Pitter et al., Methods Enzymol., 446:387-408 (2008)). Briefly, dissociation constants for peptide-protein interactions were determined by incubating fluoresceinated peptides (25 nM) with full-length HDMX or $HDM_{17-125}$ (25 pM-100 nM). Fluorescence polarization was then measured at equilibrium on a SpectraMax M5 microplate reader (Molecular Devices).

Figure 2A:
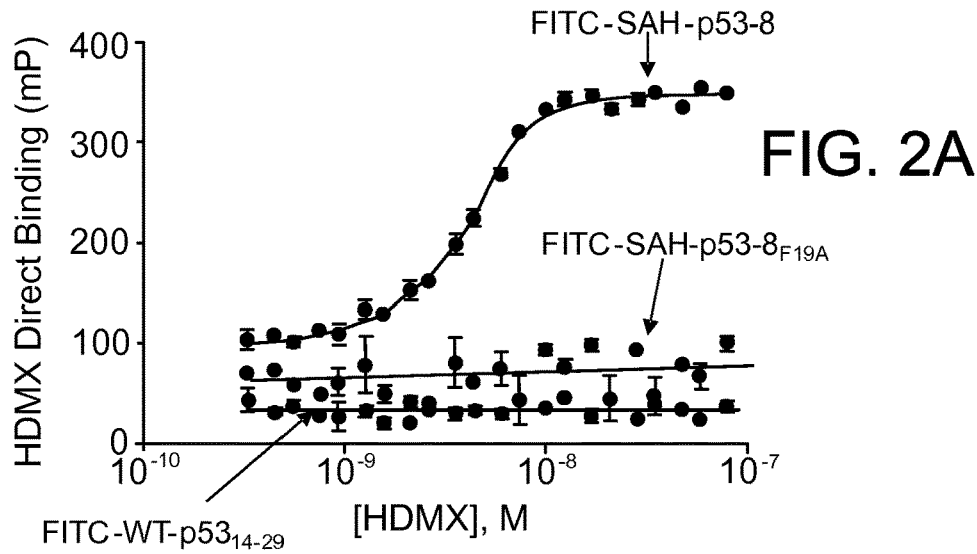
FIGS. 2A-2C are line graphs showing direct binding between recombinant HDMX and FITC-labeled p53 peptides as assessed by fluorescence polarization (A); and competition binding assays using SAH-p53-8 or Nutlin-3 to disrupt binding between FITC-SAH-p53-8 and HDM2 (B) or HDMX (C). mP: units of mill-polarization. Data show mean results of at least three independent experiments plus standard deviation.

As shown in FIG. 2A, FITC-SAH-p53-8 displayed strong affinity for HDMX (KD=2.3±0.2 nM). The affinity for SAH-p53-8 surpassed the affinity of SAH-p53-8 for HDM2 (KD=55±11 nM previously reported by Bernal et al., (J. Am. Chem. Soc., 129:2456-2457 (2007)). In contrast, as shown in FIG. 2A, $WT-p53_{14-29}$ and $SAH-p53-8_{F19A}$ showed no interaction with HDMX in the same dose ranges.

Competition binding assays were also performed to test the capacity of acetyl-capped SAH-p53-8 to disrupt the high affinity complexes of FITC-SAH-p53-8 with HDM2 and HDMX.

FP assays were conducted essentially as described above except FITC-peptide (25 nM) was combined with a serial dilution of Nutlin-3 (EMD Chemicals) or unlabeled SAH-p53-8 followed by addition of HDM2 or HDMX protein (100 nM). IC50 values for FITC-peptide displacement were calculated by nonlinear regression analysis using Prism software (GraphPad).

Figure 2B:
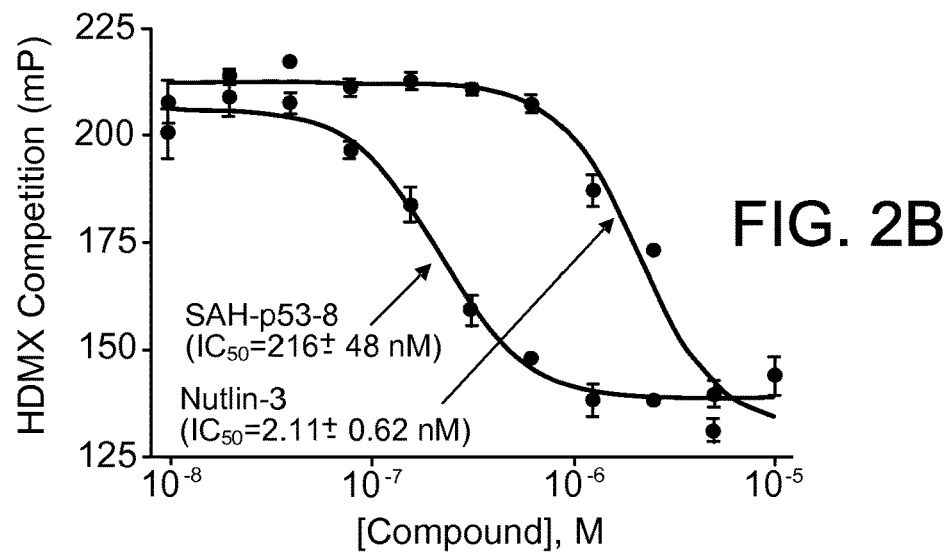
Figure 2C:
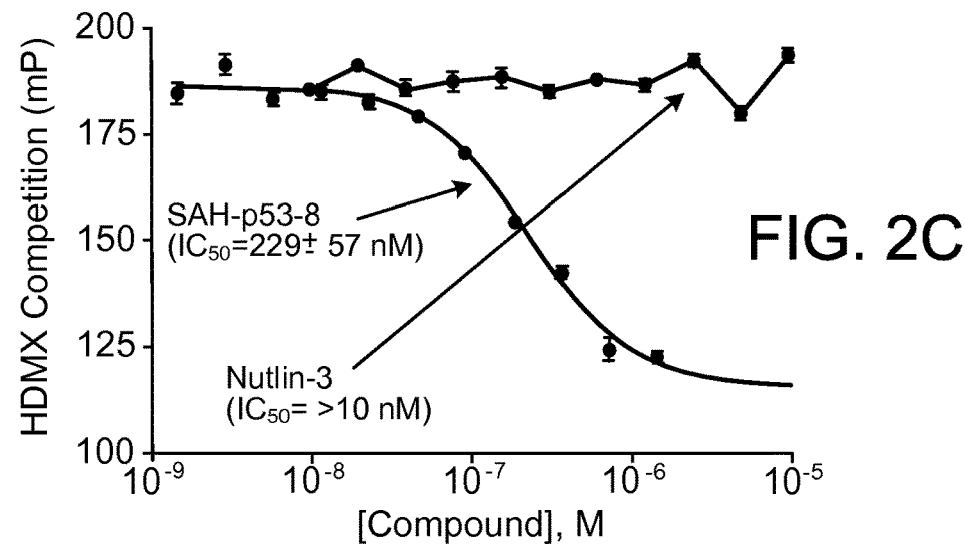

As shown in FIG. 2B, both SAH-p53-8 and the selective HDM2-inhibitor Nutlin-3 effectively competed with FITC-SAH-p53-8 for HDM2 binding (the relatively larger interaction surface of a stapled peptide compared to a small molecule may explain in part why SAH-p53-8 is more effective than Nutlin-3 in this assay). In contrast, as shown in FIG. 2C, only SAH-p53-8 was capable of dissociating the FITC-SAH-p53-8/HDMX interaction.

These data demonstrate that SAH-p53-8 targets both HDM2 and HDMX in vitro, and exhibits a greater than 25-fold binding preference for HDMX over HDM2.

Example 3

SAH-p53-8 Binds to Intracellular HDMX and HDM2

The capacity of SAH-p53-8 to target intracellular HDM2 and HDMX was assessed by conducting immunoprecipitation experiments in SJSA-X cells, an HDM2-overexpressing osteosarcoma cell line engineered to also overexpress HDMX (Wade et al., Cell Cycle, 7:1973-1982 (2008)).

Briefly, anti-FITC pull down experiments were performed as previously described (Pitter et al., Methods Enzymol., 446:387-408 (2008); Walensky et al., Mol. Cell., 24:199-210 (2006)), as follows. Cells ($1.5 \times 10^6$) were treated with FITC-SAH-p53 peptides (15 µM) and lysed in buffer B (0.1% Triton X-100, 50 mM Tris pH 7.4, 150 mM NaCl, 1 mM PMSF, EDTA-free protease inhibitor tablet (Roche), and 20 units/mL benzonase nuclease (EMD Chemicals). Proteins were co-immunoprecipitated with goat-anti-FITC antibody (AbCam) and western analysis of electrophoresed proteins performed using mouse anti-HDM2 (IF2; EMD Chemicals), rabbit anti-HDMX (BL1258; Bethyl Laboratories), and β-actin (Sigma) antibodies. Fluorescence imaging of the blot was performed using a Typhoon 8600 Imaging System (Molecular Dynamics).

Figure 3:
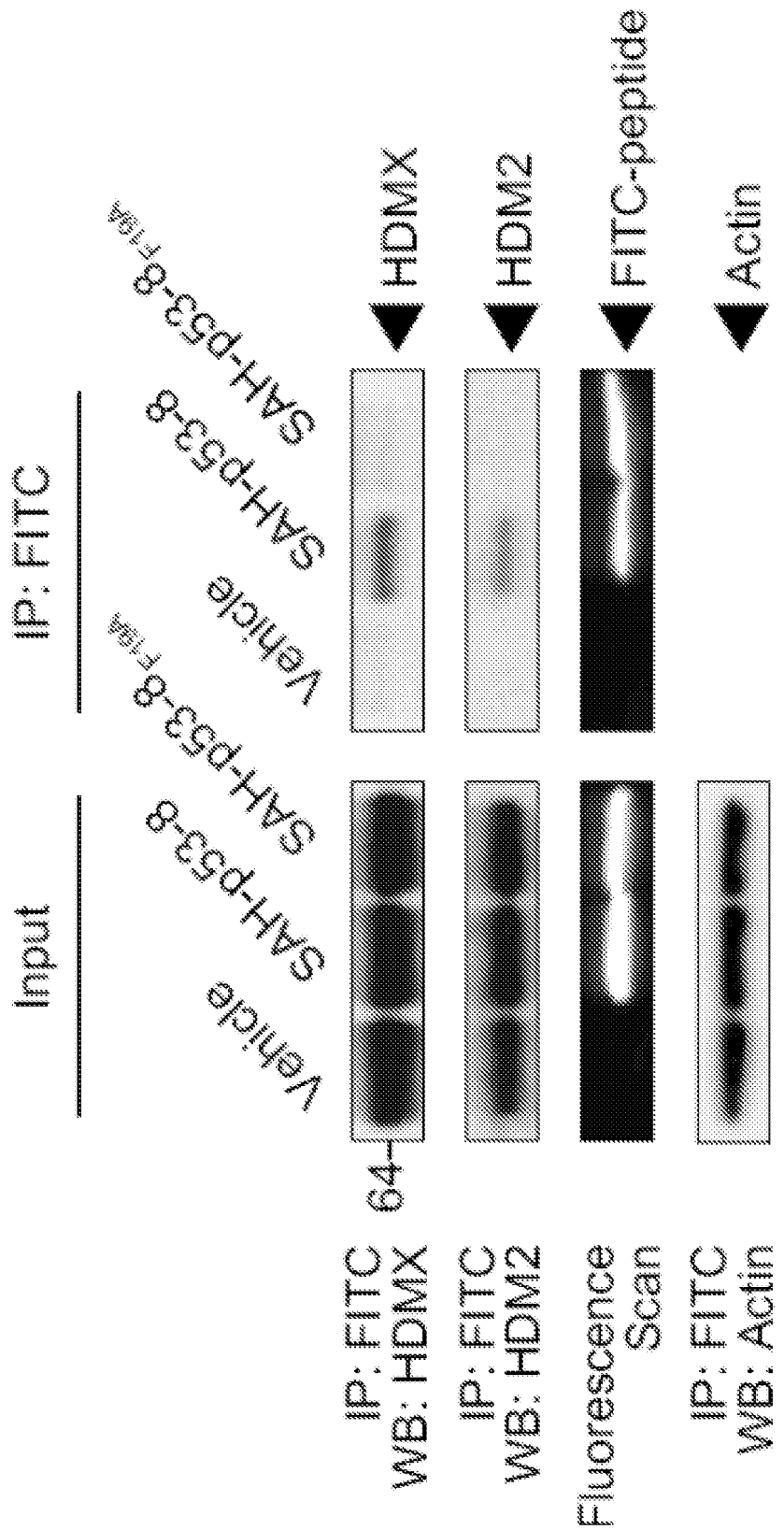
FIG. 3 is an image showing levels of HDMX, HDM2, FITC-peptide, or Actin as detected by Western blotting. Left side images show total protein detected by Western blot. Right side images show protein detected following immunoprecipitation (IP). β-actin was included as a loading control. FITC labeled peptides were detected by a fluorescence scan of the Western blot.

Cells were treated with vehicle, FITC-SAH-p53-8, or FITC-SAH-p53-$8_{F19A}$ for 12 hours. Western blot was used to confirm the presence of FITC-SAH-p53-8 and FITC-SAH-p53-$8_{F19A}$ in the cellular lysates, confirming that both SAH-p53 peptides efficiently penetrated intact SJSA-X cells. Cells were then lysed and anti-FITC pull down was performed, followed by HDM2 and HDMX western analyses. As shown in FIG. 3, native HDM2 and HDMX specifically co-immunoprecipitated with FITC-SAH-p53-8, but not with FITC-SAH-p53-$8_{F19A}$.

These data extend the in vitro findings by demonstrating that SAH-p53-8 can access both HDM2 and HDMX targets within cells.

Example 4

SAH-p53-8 is Cytotoxic to Cancer Cells that Overexpress HDMX, HDM2, or Both HDMX and HDM2

The impact of SAH-p53-8 treatment on cell viability was evaluated by treating a panel of solid tumor cells that express different levels of HDM2 and/or HDMX. Cell lines selected for use represent several types of cancer in which the levels of HDM2 and/or HDMX are altered to a degree that results in decreased p53 function. For example, cell lines used represent human cancers in which: functional HDM2 is overexpressed but HDMX is absent (see SJSA-1); HDM2 is absent but functional HDMX is overexpressed (see JEG-3); functional HDM2 and function HDMX are both overexpressed (see SJSA-X); and HDM2 and HDMX are expressed (see MCF-7). Cell lines were also included that expressed wild type p53. Cell lines used included:

SJSA-1, a HDM2-overexpressing osteosarcoma that does not express HDMX (i.e., a HDM2++/HDMX− cell line);

an engineered SJSA-X derivative that overexpresses both HDM2 and HDMX (i.e., a HDM2++/HDMX++ cell line);

the HDMX-overexpressing choriocarcinoma cell line JEG-3 that does not express HDM2 (i.e., a HDM2−/HDMX++ cell line); and the HDM2 expressing and HDMX expressing breast and colon cancer cell lines MCF-7 and HCT116 (i.e., a HDM2+/HDMX+ cell line) (see Bunz et al., 1999; Chen et al., 2007; Drukteinis et al., 2005; Kwok et al., 1994; Wade et al., 2008; Xia et al., 2008) (i.e., HDM2/HDMX− cell lines). SJSA-DD cells that express the dominant negative p53-DD protein (Shaulian et al., Mol. Cell. Biol., 12:5581-5592 (1992) and Wade et al., Cell Cycle, 7:1973-1982 (2008)), HCT116 cells deficient in p53 (Bunz et al., J. Clin. Invest., 104:263-269 (1999)), and A431 melanoma cells bearing the R273H p53 mutation (Kwok et al., Cancer Res., 54:2834-2836 (1994)) to assess the importance of p53 activity in the therapeutic strategies disclosed herein. Finally, WS1 normal human fibroblasts were tested to evaluate relative toxicity in tumor versus non-transformed cells. Use of these cell lines allows analysis of the effectiveness or efficacy of therapeutic strategies that target HDM2 or HDMX or both in cancer cells.

Cultured cells were maintained in the appropriate media (SJSA-1, SJSA-X, SJSA-DD, A431 (DMEM); JEG-3, MCF-7, WS1 (EMEM); HCT116 (McCoy's 5A)) supplemented with fetal calf serum and penicillin/streptomycin. For viability analysis, $1 \times 10^4$ cells were seeded in 96-well plates overnight, washed in PBS, and then incubated with p53 stapled peptides, Nutlin-3 (EMD Chemicals), or both in OPTI-MEM™ at the indicated doses for 24 h. Viability was assayed by addition of CellTiter-Glo™ chemiluminescence reagent according to the manufacturer's protocol (Promega). Luminescence was measured using a Spectramax M5 microplate reader (Molecular Devices). Data were normalized to vehicle-treated controls and, where appropriate synergy between SAH-p53-8 and Nutlin-3 was calculated using the Calcusyn software package (Chou, 2006) (Biosoft; Cambridge, UK). All viability assays were performed in at least triplicate.

Figure 4A:
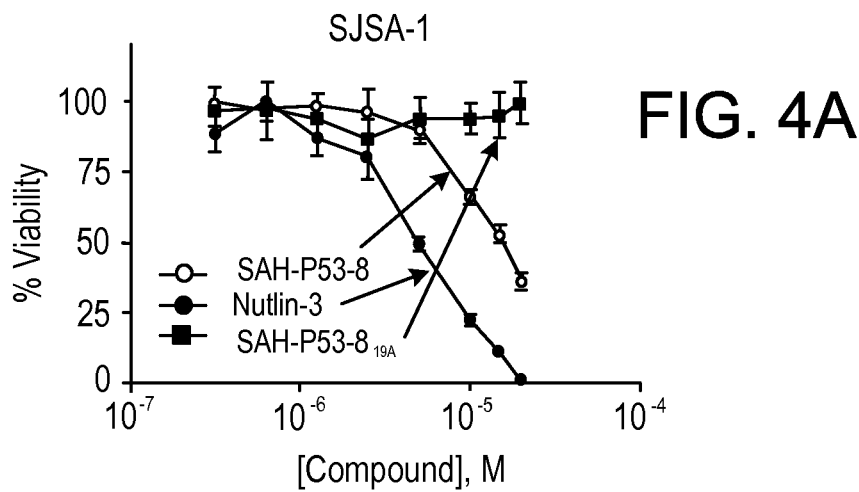
FIGS. 4A-4I are line graphs showing cell viability in various cell lines exposed to SAH-p53-8, Nutlin-3 or SAH-p53-8$_{F19A}$. Cells lines used included cancer cell lines (e.g., osteosarcoma, choriocarcinoma, colon cancer, epithelial carcinoma, breast cancer) with differential expression levels of HDM2 or HDMX/MDM2 or MDMX (FIGS. 4A-4E), deficient or dysfunctional p53 (FIGS. 4F-4H), and a non-tumor control (FIG. 4I). Cells were exposed to CellTiter-Glo™ reagent (Promega) and viability was assessed by ATP-induced chemiluminescence. Data are mean plus standard deviation for experiments performed at least in triplicate.
Figure 4B:
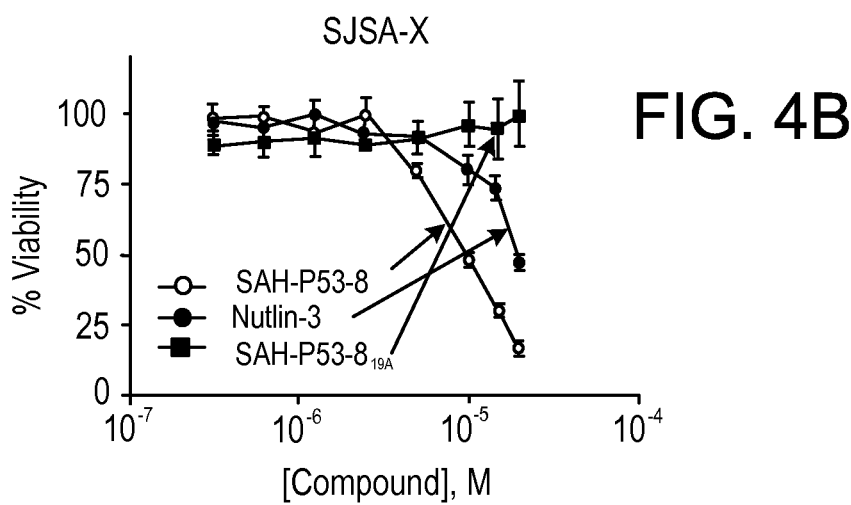
Figure 4C:
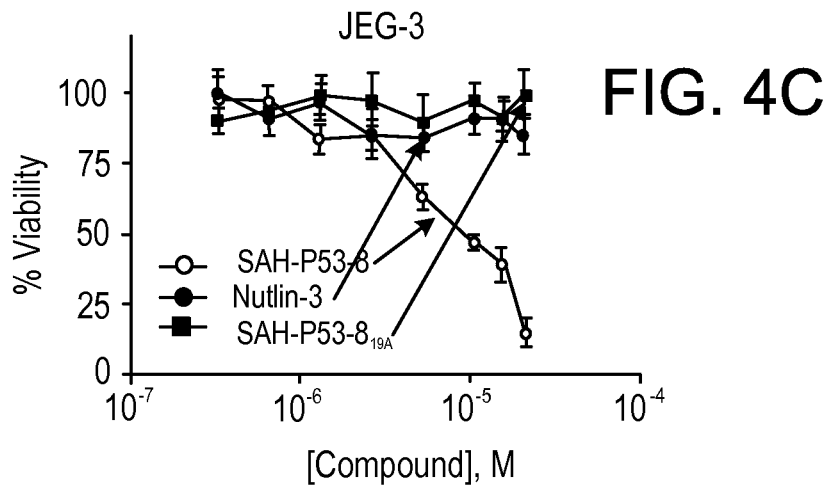

As noted above, cultured cells were treated with serial dilutions of Nutlin-3, SAH-p53-8, or the SAH-p53-$8_{F19A}$ point mutant control. As shown in FIG. 4A, whereas SJSA-1 cells were very sensitive to treatment with Nutlin-3, SJSA-X and JEG-3 cells showed little to no response to Nutlin-3 (see FIGS. 4B and 4C, respectively). In other words, Nutlin-3 reduces cell viability in cells that express functional HDM2, but not HDMX (i.e., SJSA-1); however, Nutlin-3 is not effective in cells that do not express HDM2, but that do express HDMX (i.e., JEG-3), and the efficacy of Nutlin-3 is reduced in cells that express both HDM2 and HDMX (i.e., SJSA-X). These observations are consistent with the ability of Nutlin-3 to target HDM2 but not HDMX.

Figure 4D:
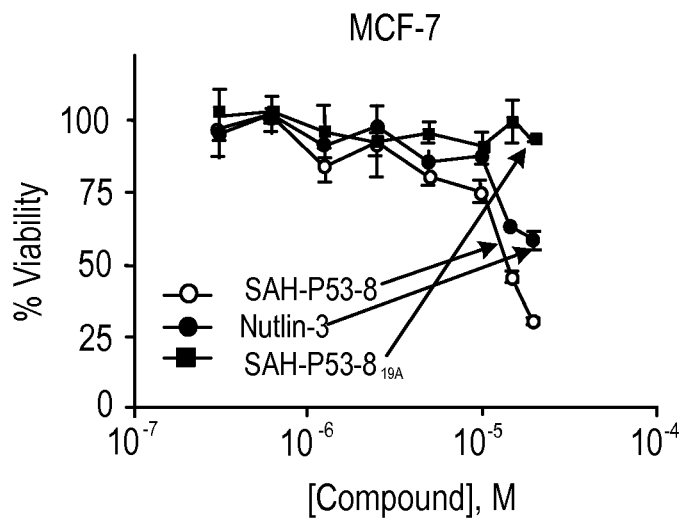
Figure 4E:
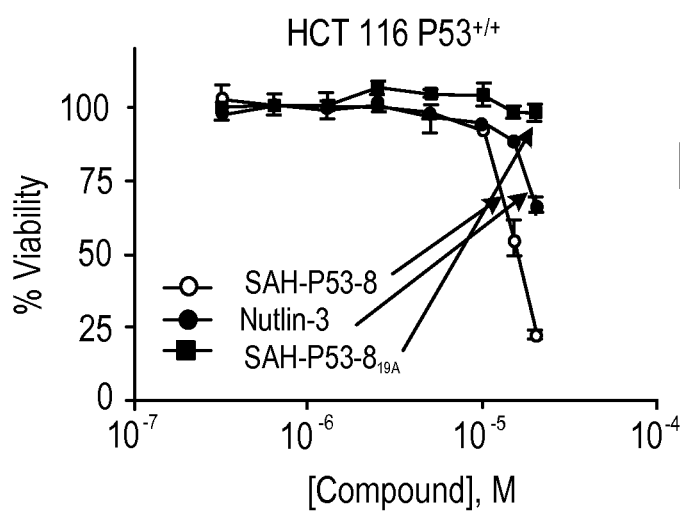

As shown in FIGS. 4D and 4E, MCF-7 and HCT116 cells, which express HDM2 and HDMX, but do not overexpress either protein, were also modestly sensitive to Nutlin-3 treatment, consistent with the co-expression of HDM2 and HDMX in these cells. Thus, these data demonstrate that Nutlin-3 reduces cell viability when HDM2 is overexpressed or expressed, but that the efficacy of Nutlin-3 when used alone is decreased in cells that also overexpress HDMX.

In contrast, as shown in FIG. 4A-4E, SAH-p53-8 caused dose-dependent inhibition of cell viability in all five cell lines. This observation supports that SAH-p53-8 is capable of reactivating the p53 pathway when cells express elevated or normal levels of HDM2, HDMX, or both proteins.

Of note, despite the relatively enhanced capacity of SAH-p53-8 to displace the p53 transactivation helix from HDM2 compared to Nutlin-3 in vitro shown in FIG. 2B, Nutlin-3 was more cytotoxic than SAH-p53-8 in SJSA-1 cells (see FIG. 4A. This apparent discrepancy likely derives from (1) the preferential HDMX-binding activity of SAH-p53-8 compared to HDM2, thus lowering the effective concentration of SAH-p53-8 available for HDM2-targeting, and (2) the potential differential efficiencies of cellular import mechanisms for stapled peptides (i.e. pinocytosis (Bernal et al., J. Am. Chem. Soc., 129:2456-2457 (2007); Walensky et al., Science, 305:1466-1470 (2004)) and small molecules (i.e. diffusion). Consistent with the in vitro binding data shown herein, which revealed a binding preference of SAH-p53-8 for HDMX over HDM2 (see FIG. 2A), SJSA-X cells were more susceptible to SAH-p53-8 than SJSA-1 cells (see FIGS. 4A and 4B). Moreover, the HDMX-overexpressing JEG-3 cells were most sensitive to SAH-p53-8 but most resistant to Nutlin-3 (see FIG. 4C). This finding is considered in the following mechanistic analysis.

Figure 4F:
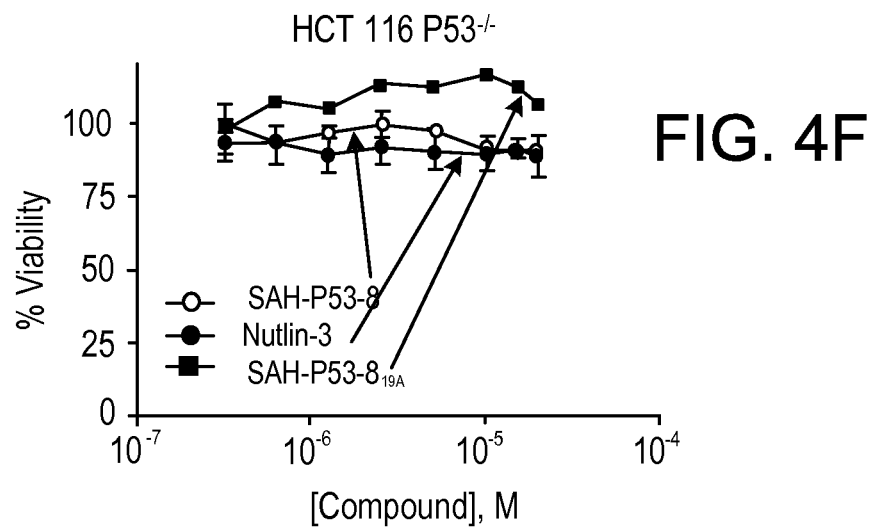
Figure 4G:
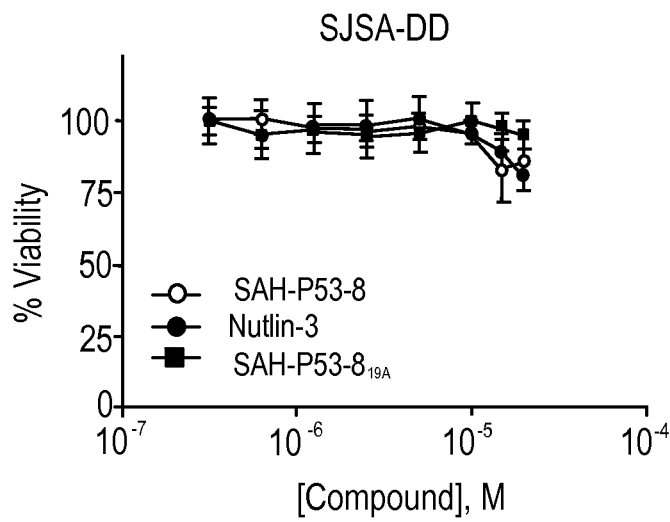
Figure 4H:
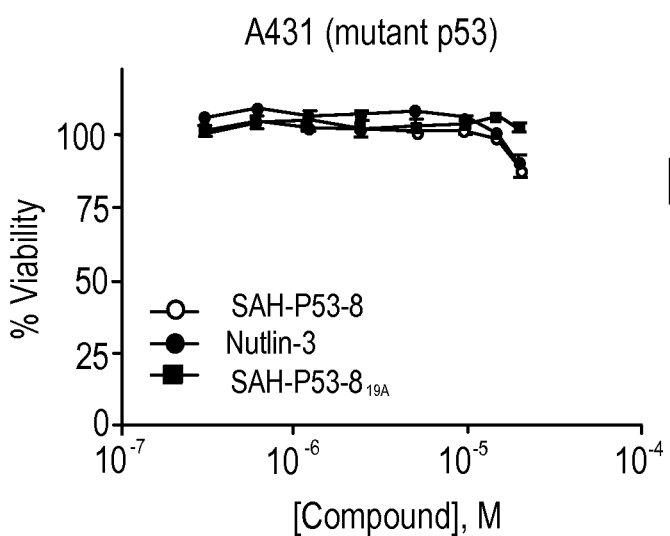
Figure 4I:
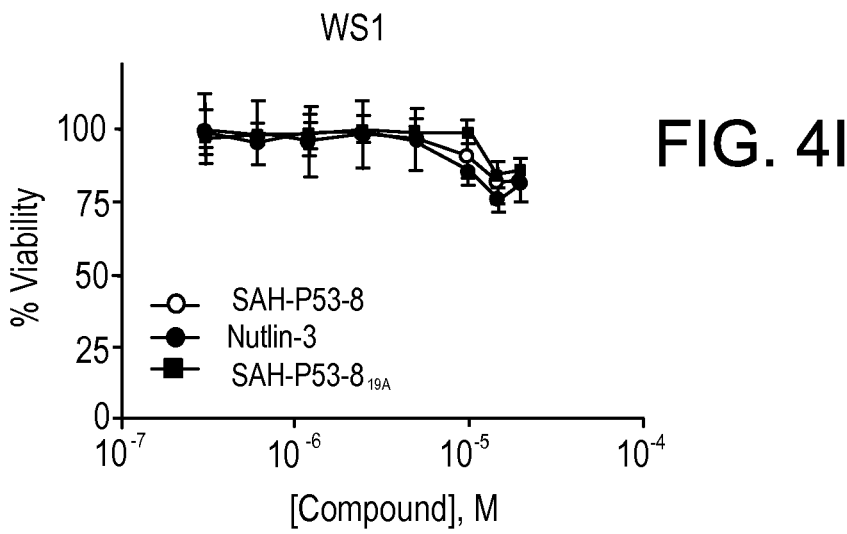

SAH-p53-8 cytotoxicity was confirmed to be specifically dependent on wild-type p53 protein activity and does not significantly affect the viability of normal fibroblasts (see FIG. 4I). Genetic deletion of p53 from HCT116 cells or overexpression of a dominant negative form of p53 in SJSA-1 cells rendered both cell types completely insensitive to Nutlin-3 and SAH-p53-8 (see FIGS. 4F and 4G). As shown in FIG. 4H, the A431 melanoma cell line, which bears an inactivating p53 point mutation, was similarly unaffected by the treatments. As noted above, SAH-p53-8, like Nutlin-3, was found to have no impact on the viability of normal human fibroblasts (see FIG. 4I).

As a further measure of specificity, the mutant peptide SAH-p53-$8_{F19A}$ was observed to be inactive in all cell lines tested (see FIG. 4A-4I). These data further indicate that the anti-tumor cell activity of SAH-p53-8 is peptide-sequence dependent and derives from its intracellular targeting of HDM2 and HDMX.

Example 5

SAH-p53-8 Blocks HDMX-Mediated Sequestration of p53 and Reactivates the p53 Tumor Suppressor Pathway Immunoprecipitation Studies Immunoprecipitation studies were performed in the JEG-3 cell line a HDM2−/HDMX++ cell line) to determine whether the pharmacologic advantage of SAH-p53-8 in Nutlin-3-resistant cells derives from HDMX targeting.

Cell culture and immunoprecipitations were performed as described in Example 3 except, for HDMX immunoprecipitation experiments, cells ($1.5 \times 10^6$) were treated with either SAH-p53-8 alone or Nutlin-3 (EMD Chemicals) alone at the indicated doses in 0.5 mL OPTI-MEM™ (Invitrogen) with or without 10 μMG-132 for 6 h. After washing with PBS (2×1 mL), the cells were lysed in buffer B. HDMX was immunoprecipitated with anti-HDMX antibody (BL1258; Bethyl Laboratories) and western analysis of electrophoresed protein was conducted using p53 (DO-1; EMD Chemicals or FL-393; Santa Cruz Biotechnology), HDMX (MDMX-82; Abcam), and HAUSP (anti-USP7, Bethyl Labs) antibodies, and Western Lightning chemiluminescence reagent (PerkinElmer). After 6 hour treatment with vehicle, SAH-p53-8, or Nutlin-3, cellular extracts were prepared and subjected to anti-HDMX pull down, followed by p53 western analysis.

Figure 5A:
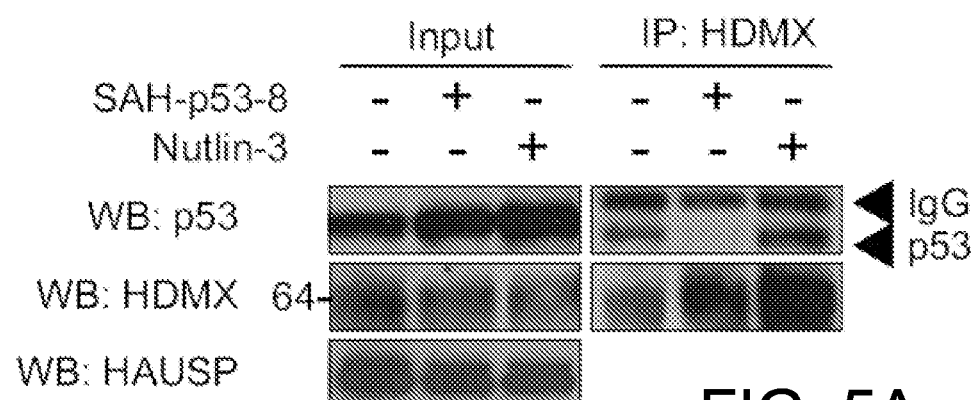
FIGS. 5A and 5B are images showing that SAH-p53-8 blocks the formation of p53-HDMX complexes. (A) JEG-3 cells were exposed to vehicle, 20 μM SAH-p53-8, or 20 μM Nutlin-3 for 6 hours. Cellular extracts (input) and anti-HDMX immunoprecipitates (IP:HDMX) were subjected to SDS-PAGE and Western blotting. Images show levels of p53, HDMX, and HAUSP detected by Western blotting. (B) JEG-3 cells were treated with increasing concentrations of SAH-p53-8 (i.e., 0-20 μM SAH-p53-8) in the presence of 10 μM MG132 for 6 hours. Cellular extract (input) and anti-HDMX immunoprecipitates (IP:HDMX) were analyzed by SDS-PAGE and Western blotting for p53, HDMX, and HAUSP. Input levels represent total protein and IP represent protein levels detected following immunoprecipitation.

As shown in FIG. 5, JEG-3 were found to have robust levels of p53 protein, which co-immunoprecipitated with HDMX (see FIG. 5A). Whereas an increase in p53 levels was observed upon treatment with either SAH-p53-8 or Nutlin-3 (see FIG. 4A 'input'), only SAH-p53-8 treatment impacted JEG-3 cell viability.

Figure 5B:
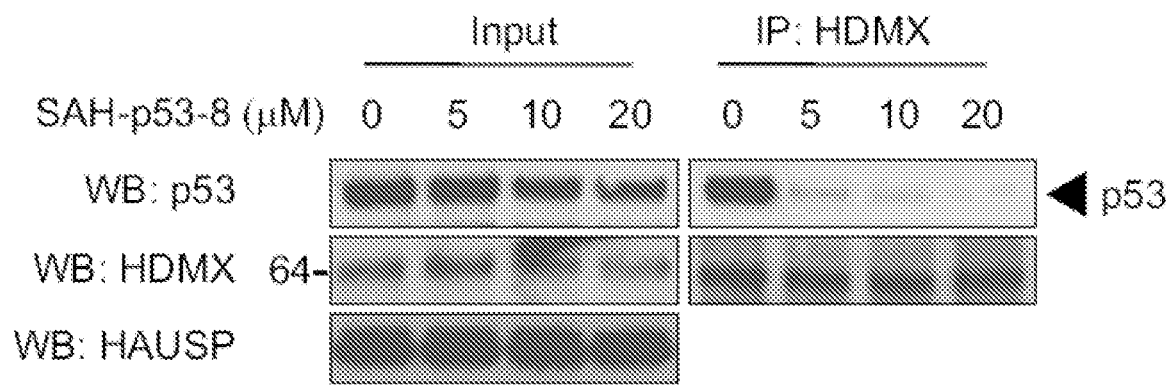

HMDX IP was used to examine whether SAH-p53-8 treatment prevents HDMX-mediated sequestration of p53, especially when p53 levels are further boosted by HDM2 blockade. As shown in FIG. 5A 'IP: HDMX', SAH-p53-8 effectively blocked the formation of p53-HDMX complexes, resulting in a lower amount of p53 being immunoprecipitated by HDMX. In contrast, p53-HDMX complexes were preserved, if not increased, in Nutlin-3 treated cells (see FIG. 5A 'IP: HDMX'). As shown in FIG. 5B, p53 levels were further stabilized by treating cells with the proteasome inhibitor MG-132. Furthermore, this increased stability noted by an increase in precipitated HDMX-p53 complex was decreased in a dose-dependent manner upon treatment with SAH-p53-8 (see FIG. 5B).

Figure 5C:
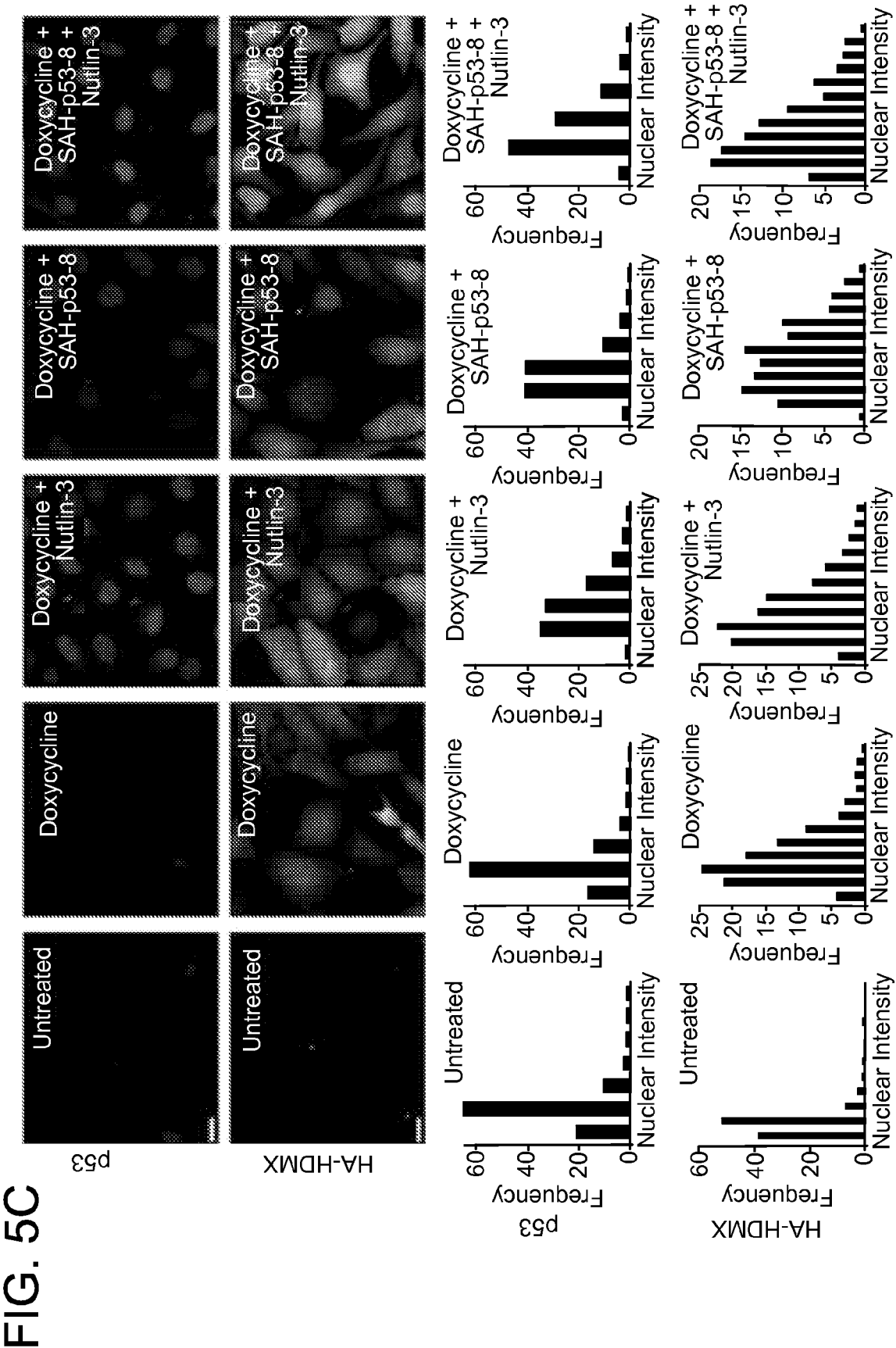
FIGS. 5C-5E are images and derived bar graphs showing that SAH-p53-8, but not Nutlin-3 blocks the formation of p53-HDMX complexes in intact cells. (C) Doxycycline-inducible U2OS cells were treated with or without doxycycline in the presence of Nutlin-3 (10 μM), SAH-p53-8 (10 μM), or both, and induction of HA-HDMX and p53 was detected and quantitated by immunofluorescence. Scale bar, 10 microns (D) Cultured U2OS cells were treated with or without doxycycline in the presence of Nutlin-3, SAH-p53-8, or both and then processed for P-LISA. Scale bar, 10 microns (E) Quantitation of p53-HDMX complexes as detected by P-LISA. Data are mean+/−s.d. *p=0.0003, **p=0.0001, unpaired t-test with Welch's correction.
Figure 5D:
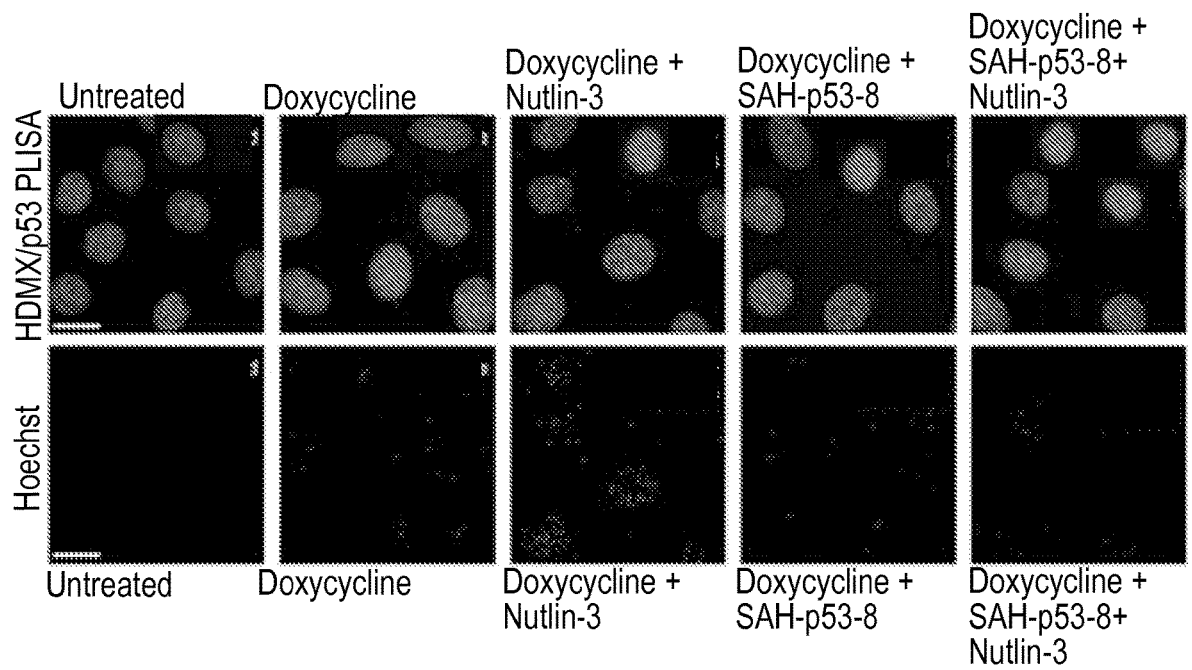
Figure 5E:
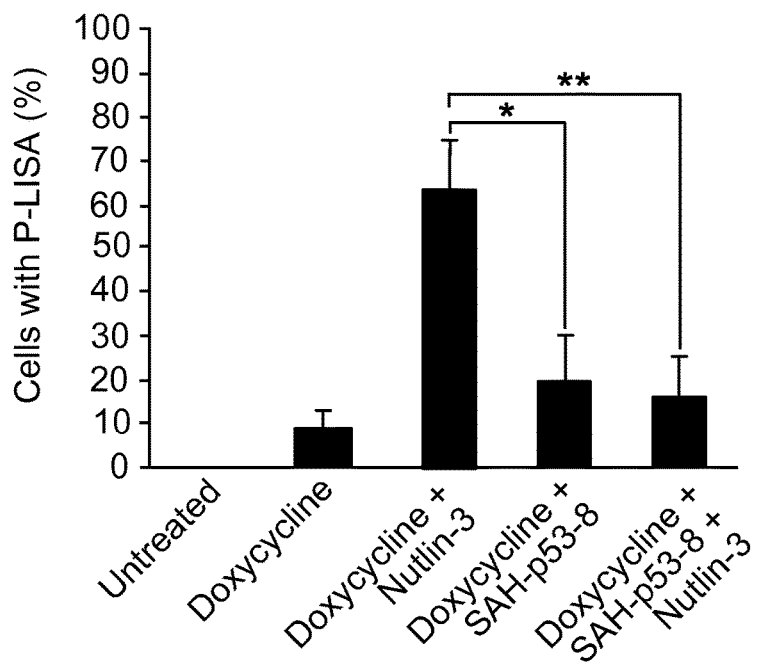

To document that SAH-p53-8 could disrupt the p53/HDMX interaction in a cellular context, we employed a proximity ligation in situ assay, or P-LISA, and directly monitored p53-HDMX complex formation and pharmacologic dissociation in cells (Söderberg et al., 2006) (FIG. 5C-E). U2OS osteosarcoma cells containing a doxycycline-inducible HA-HDMX construct (Wang et al., 2007) were treated with doxycycline in the presence or absence of SAH-p53-8, Nutlin-3, or both. In the presence of doxycycline alone, the HA-HDMX produced binds to endogenous p53, leading to the formation of detectable but low intensity P-LISA foci (FIG. 5D, 5E). The combination of doxycycline and Nutlin-3 treatment generated a robust P-LISA signal, which represents abundant formation of p53/HA-HDMX complexes (FIG. 5D, 5E). Despite similar levels of p53 induction in response to single agent SAH-p53-8 or Nutlin-3 treatment (FIG. 5C), the P-LISA signal generated by treatment with doxycycline was blocked upon co-treatment with SAH-p53-8 (FIG. 5D, 5E). Furthermore, combining SAH-p53-8 with doxycycline/Nutlin-3 significantly reduced the P-LISA signal generated by the doxycycline/Nutlin-3 combination alone (FIG. 5D, 5E).

Taken together, these data support that SAH-p53-8, but not Nutlin-3, inhibits the formation of p53-HDMX complexes due to its capacity to target intracellular HDMX.

Quantitative PCR and Apoptosis Studies

To link the pharmacologic disruption of the p53-HDMX protein complex by SAH-p53-8 with reactivation of the p53 tumor suppressor pathway, p53 transcriptional activity was indirectly analyzed by assessing transcriptional activity of p53 targets using qPCR analysis. P53 activity was also indirectly assessed using apoptosis assays, or more specifically by measuring apoptosis using a caspase-3/7 activation assay.

qPCR studies were performed as follows. JEG-3 cells ($7.5 \times 10^6$) were seeded in 6-well plates and treated with vehicle or 20 μM SAH-p53-8 or Nutlin-3 (EMD Chemicals), and incubated for 6 h at 37° C. RNA samples were prepared using the RNEasy Mini kit (Qiagen). Total RNA was reverse transcribed to cDNA using Superscript III reverse transcriptase (Invitrogen). The derived cDNA was employed as the substrate to measure relative transcript levels by qRT-PCR on a PRISM 7700 system using SYBR Green PCR Master Mix (Applied Biosystems). Primers specific for HDM2, p21, MIC-1, and the UBB control were employed. Triplicate reactions were prepared in 96-well optical PCR plates. Threshold-cycle (Ct) values were automatically calculated for each replicate and used to determine the relative expression of the gene of interest relative to UBB for both treated and untreated samples by the $2^{-\Delta\Delta C_t}$ method (Livak and Schmittgen, Methods, 25:402-408 (2001)).

Figure 6A:
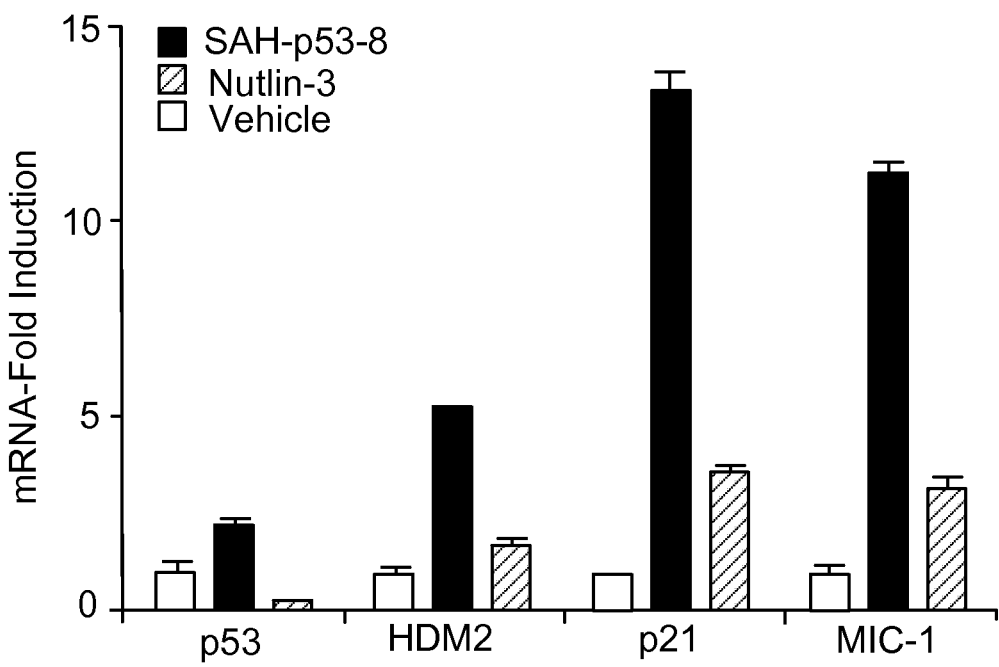
FIG. 6A is a bar graph showing that p53-transcriptional activity is reactivated by SAH-p53-8. JEG-3 cells were treated with vehicle, SAH-p53-8 (20 or Nutlin-3 (20 μM). Transcriptional upregulation was assessed by quantitative PCR. mRNA levels of HDM2, p21, and MIC-1 in the presence of SAH-p53-8 (left column), Nutlin-3 (middle column), and vehicle control (right column) are shown.

JEG-3 cells were treated with vehicle, Nutlin-3 (20 μM), or SAH-p53-8 (20 μM) for 6 h at 37° C., followed by RNA isolation, reverse transcription, and qPCR analysis of the derived cDNA substrate using HDM2, p21, and MIC-1 primers. As shown in FIG. 6A, whereas Nutlin-3 induced a modest 1.5-4 fold upregulation of p53 transcriptional targets compared to vehicle, SAH-p53-8 triggered significantly higher (5-14 fold) mRNA levels for the same target genes.

Apoptosis studies were performed as follows. JEG-3 cells (1×104) were seeded in 96-well plates overnight, washed in PBS, and then incubated with the indicated doses of SAH-p53-8 or Nutlin-3 (EMD Chemicals) in OPTI-MEM™ for 12 h. Caspase-3/7 activity was assayed by addition of Caspase-3/7-Glo™ chemiluminescence reagent according to the manufacturer's protocol (Promega) and luminescence measured using a Spectramax M5 microplate reader (Molecular Devices).

Figure 6B:
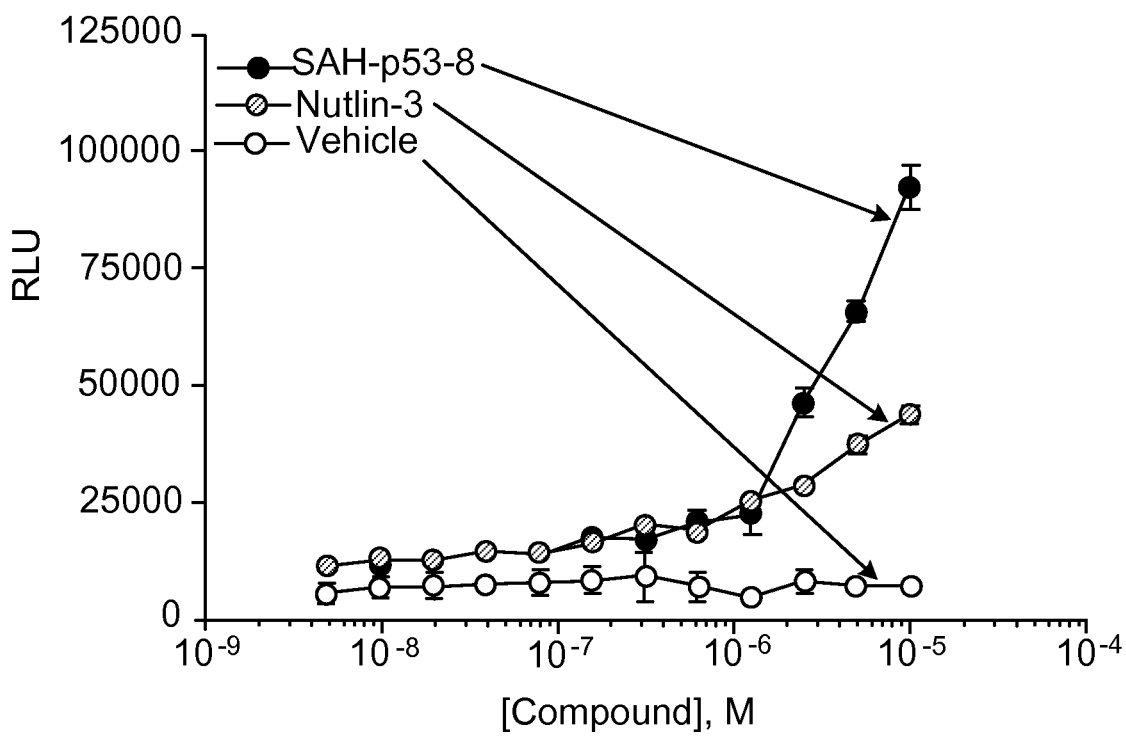
FIG. 6B is a line graph showing that p53-dependent apoptosis is reactivated by SAH-p53-8. JEG-3 cells were treated with vehicle, or increasing concentrations (i.e., 0.3-10 μM SAH-p53-8), or Nutlin-3 for 12 hours. The level of apoptosis was then assessed by exposing cells to Caspase-3/7-Glo™ reagent and detecting the cleavage of proluminescent caspase3/7 substrate.

As shown in FIG. 6B, SAH-p53-8 treatment caused dose-responsive activation of caspase-3/7, whereas Nutlin-3 had little effect.

Thus, targeted disruption of the p53-HDMX complex by SAH-p53-8 in Nutlin-3-resistant JEG-3 cells coincides with upregulation of p53 transcriptional targets, caspase-3/7 activation, and reduced tumor cell viability.

Example 6

Suppression of JEG-3 Tumor Growth by Reactivation of the p53 Pathway In Vivo

To determine if SAH-p53-8 could modulate the p53 pathway in vivo and thereby inhibit tumor growth, the activity of vehicle, Nutlin-3, and SAH-p53-8 were compared in a JEG-3 murine xenograft model.

Briefly, JEG-3 xenografts were established by injecting $10^7$ cells subcutaneously into the flanks of NOD-SCID-IL2Rγnull (NSG) mice (Jackson Labs). When tumors reached an average volume of 100 $mm^3$, cohorts (n=7) were treated with vehicle (5% DMSO in D5W), SAH-p53-8 (10 mg/kg), or Nutlin-3 (10 mg/kg) (EMD Chemicals) once daily for 4 days by intravenous injection. Tumor size was measured with calipers on days 1, 3, 4 and 5. On day 5, the mice were euthanized, tumors excised, and a portion of each tumor flash frozen and subjected to RNA isolation for qRT-PCR analysis, as described above. The remainder of each animal was fixed in Bouin's fixative and submitted to the Dana-Farber/Harvard Cancer Center (DF/HCC) Rodent Histopathology Core for complete necropsy. Animal experiments were approved by and performed in accordance with the guidelines and regulations set forth by the Institutional Animal Care and Use Committee of the Dana-Farber Cancer Institute.

Figure 7A:
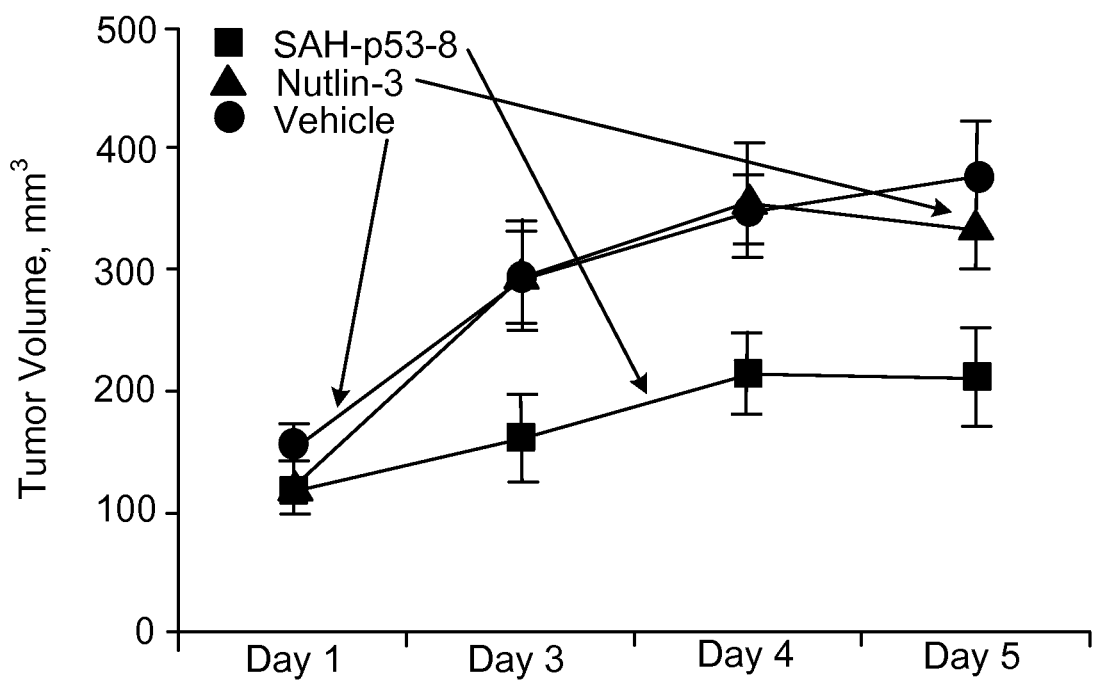
FIGS. 7A and 7B show a line graph and a bar graph, respectively, showing that SAH-p53-8 overcomes HDMX-mediated p53 suppression and blocks tumor growth in vivo. (A) Cohorts (n=7) of JEG-3 xenograft mice were treated with either vehicle (5% DMSO in D5W), or 10 mg/kg of SAH-p53-8 introduced by daily intravenous injection for 4 days, or Nutlin-3 introduced by daily intravenous injection for 4 days. Tumor volume was monitored by caliper measurement on days 1, 3, 4, and 5 (statistical significance of data are: day 3; SAH-p53-8 versus vehicle=p=0.032, SAH-p53-8 versus Nutlin-3=p=0.032, Nutlin-3 versus vehicle p=0.94; Day 4; SAH-p53-8 versus vehicle p=0.008, SAH-p53-8 versus Nutlin-3 p=0.026, Nutlin-3 versus vehicle p=0.88; Day 5; SAH-p53-8 versus vehicle p=0.017, SAH-p53-8 versus Nutlin-3 p=0.037, Nutlin-3 versus vehicle p=0.46). (B) Tumors were excised and RNA was isolated and levels of p53 transcription targets HDM2, p21, and MIC-1 were analyzed by qPCR.

As shown in FIG. 7A, whereas tumor growth rate was not affected by Nutlin-3 treatment, SAH-p53-8 significantly suppressed tumor growth, achieving and maintaining a 37-46% reduction in tumor burden compared to vehicle and Nutlin-3 throughout the 5-day evaluation period.

Figure 7B:
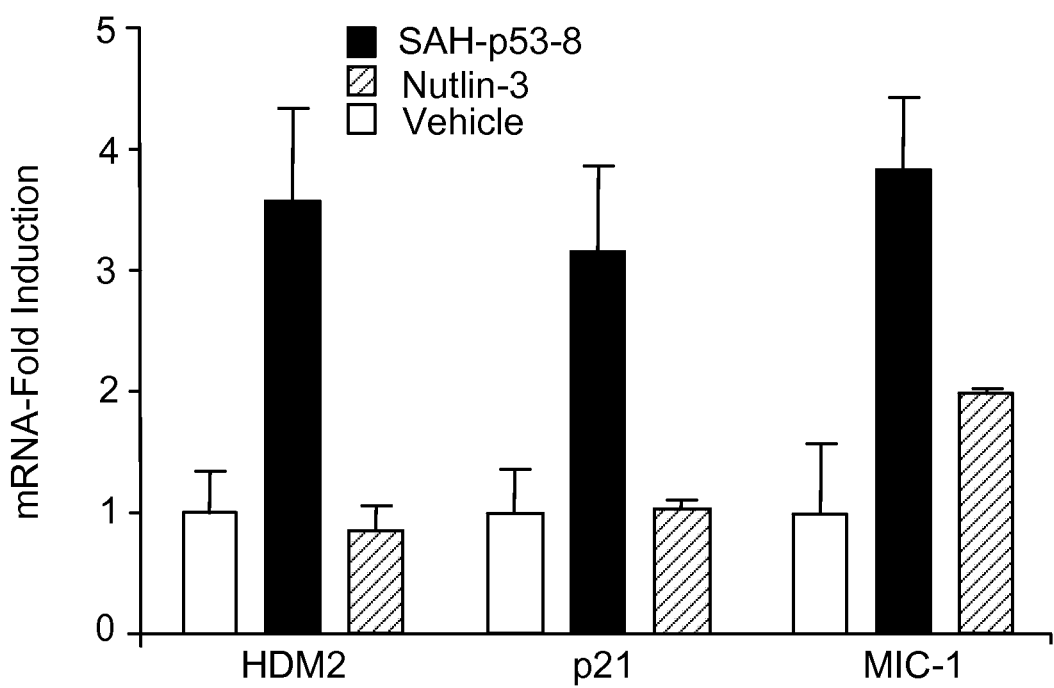

On day 5, the tumors were excised, flash frozen, and RNA extracted for qPCR analysis using the HDM2, p21, and MIC-1 primer sets. Like the corresponding in vitro study performed with cultured JEG-3 cells, SAH-p53-8 induced statistically significant transcriptional activation of HDM2, p21, and MIC-1 in the tumors of treated mice (see FIG. 7B). Histologic examination of SAH-p53-8-treated mice showed no obvious toxicity of the compound to normal tissues, consistent with the inactivity of SAH-p53-8 in cell viability assays using cultured WS1 fibroblasts (see FIG. 4I).

These in vivo data underscore the pharmacologic potential of HDMX targeting to functionally suppress tumor growth by reactivating the p53 pathway in the context of HDMX-mediated p53 suppression and Nutlin-3 resistance.

Example 7

Blueprint for Matching HDM2, HDMX, or Dual Inhibitors to Susceptible Cancer Cells Because HDMX targeting by SAH-p53-8 was most effective in reducing tumor cell viability when basal p53 levels were naturally elevated, synergy studies were performed in Nutlin-3-resistant cells to test whether SAH-p53-8-mediated HDMX inhibition could re-sensitize cells to Nutlin-3-mediated p53 upregulation.

In cells with high HDMX, the pool of p53 induced by Nutlin-3 treatment can be sequestered in p53-HDMX complexes, subverting Nutlin-3 activity. Accordingly, it was hypothesized that HDMX blockade by SAH-p53-8 in such cells could restore Nutlin-3 activity by preventing HDMX-mediated p53 sequestration. The breast adenocarcinoma cell line MCF-7 overexpresses HDMX (Danovi et al., Mol. Cell. Biol., 24:5835-5843 (2004)) and is only modestly sensitive to Nutlin-3 treatment (Wade et al., Cell Cycle, 7:1973-1982

Figure 8:
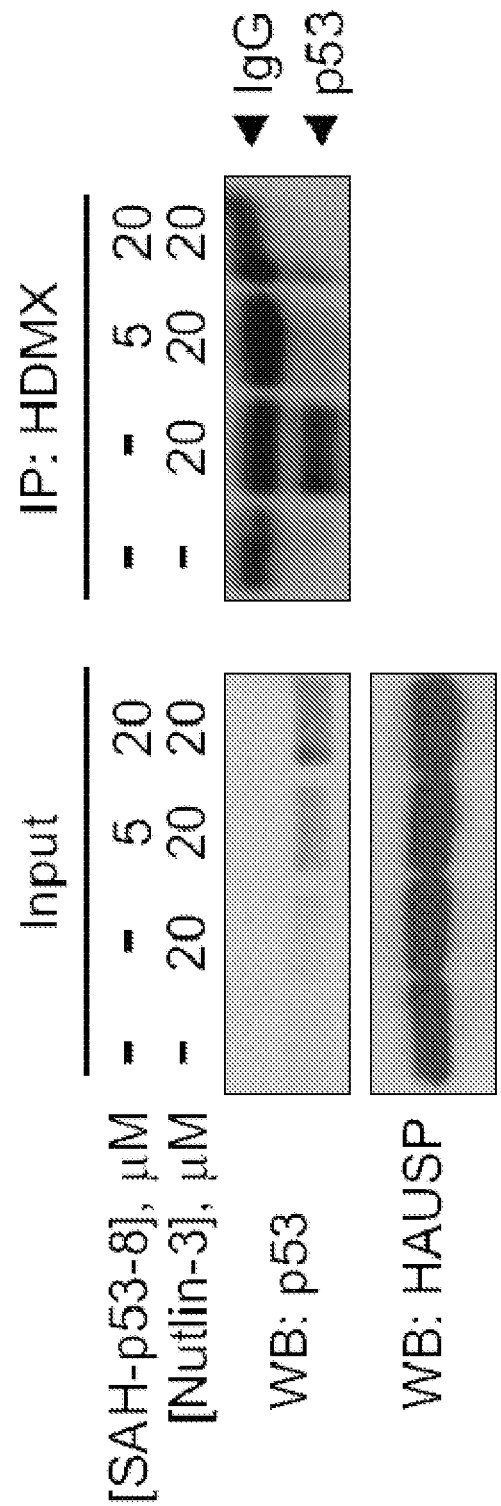
FIG. 8 is an image of an immunoblot showing that pharmacologic induction of p53-HDMX complexes sensitizes Nutlin-3-resistant cancer cells to HDMX inhibition. MCF-7 breast adenocarcinoma cells were exposed to vehicle, Nutlin-3 (20 μM), or Nutlin-3 (20 μM) in combination with 5 or 20 μM SAH-p53-8. Cells were exposed to MG-132 at 10 μM for 6 hours to induce HDMX-p53 complex formation. Cellular extracts (input-left side immunoblot) and anti-HDMX immunoprecipitates (IP:HDMX-right side immunoblot) were analyzed by SDS-PAGE and Western blotting. Levels of p53 and HAUSP are shown.
Figure 9A:
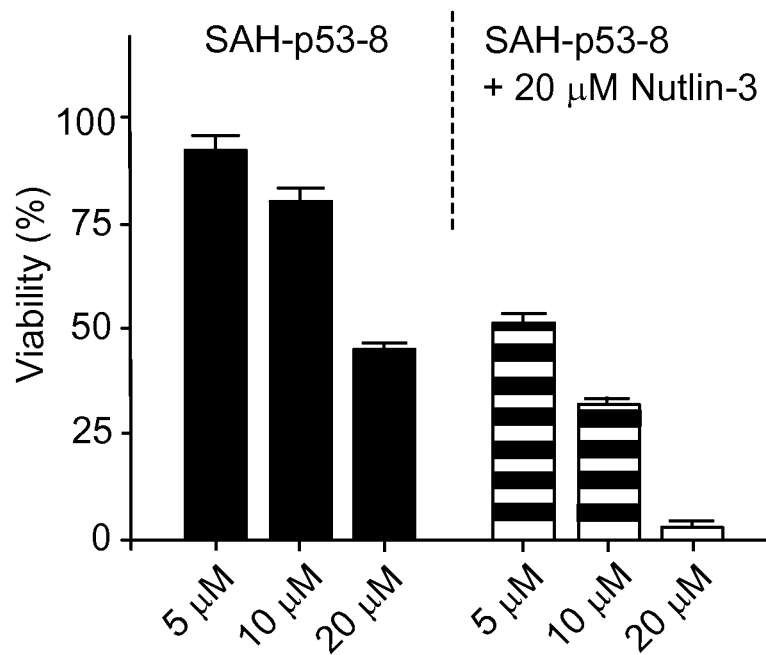
FIGS. 9A-9B are bar graphs showing that SAH-p53-8 and Nutlin-3 act synergistically in reducing tumor cell viability. (A) MCF-7 cells were exposed to increasing concentrations (i.e., 5-20 μM) of SAH-p53-8 in the presence or absence of 20 μM Nutlin-3. Cell viability was assessed at 24 hours by Cell Titer-Glo™ assay. (B) MCF-7 cells were exposed to increasing concentrations (i.e., 5-20 μM) of Nutlin-3 in the presence or absence of 20 μM SAH-p53-8 and cell viability was assessed as in '(A).'
Figure 9B:
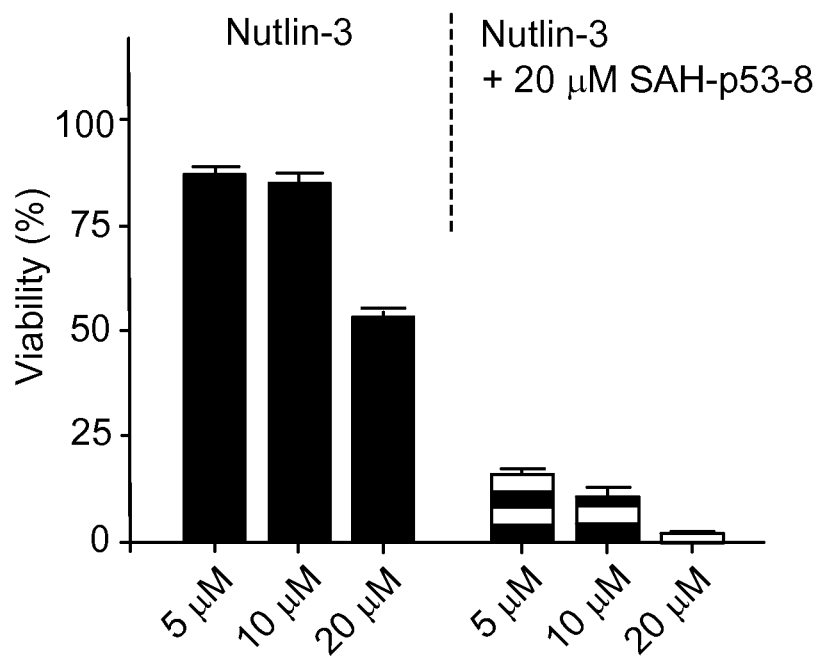
Figure 10A:
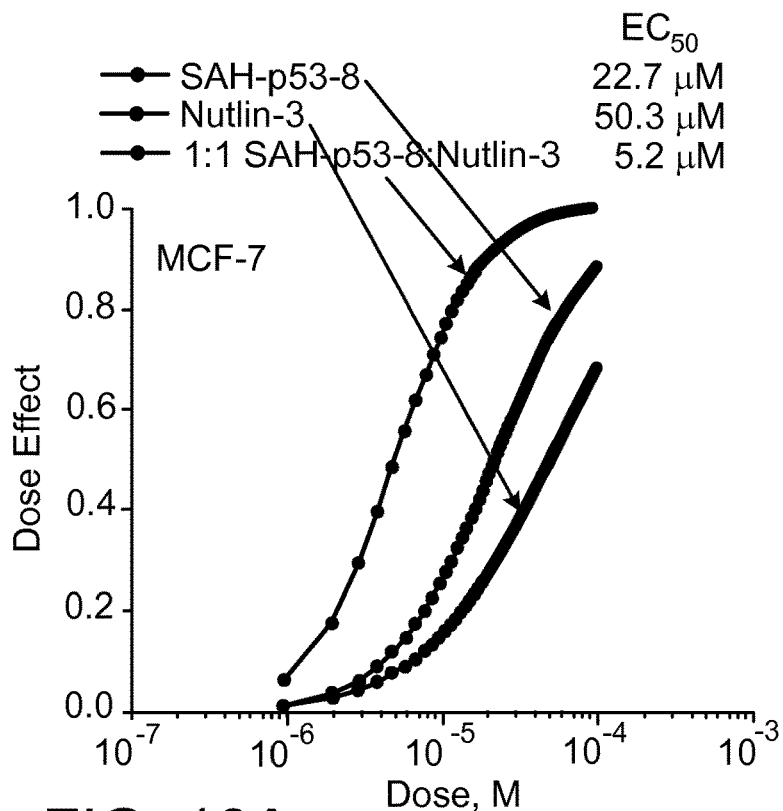
FIGS. 10A-10D are synergy graphs showing SAH-p53-8 and Nutlin-3 synergize. MCF-7 (A), JEG-3 (B), SJSA-1 (C), and SJSA-X (D) cells were treated with 0.5-20 µM SAH-p53-8, Nutlin-3, or an equimolar combination. Dose-effect synergy analyses were then performed and are shown.
Figure 10B:
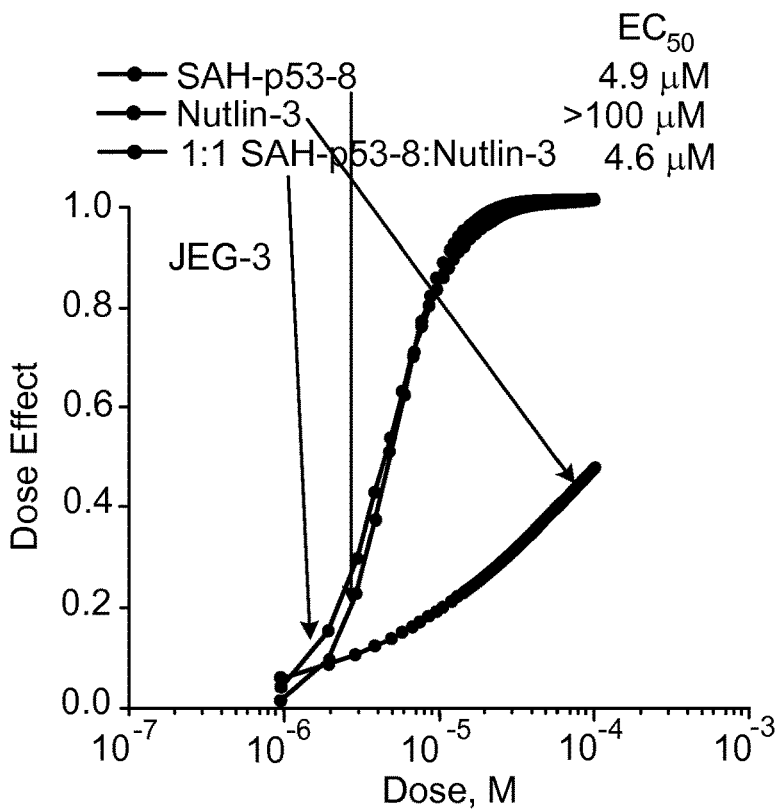
Figure 10C:
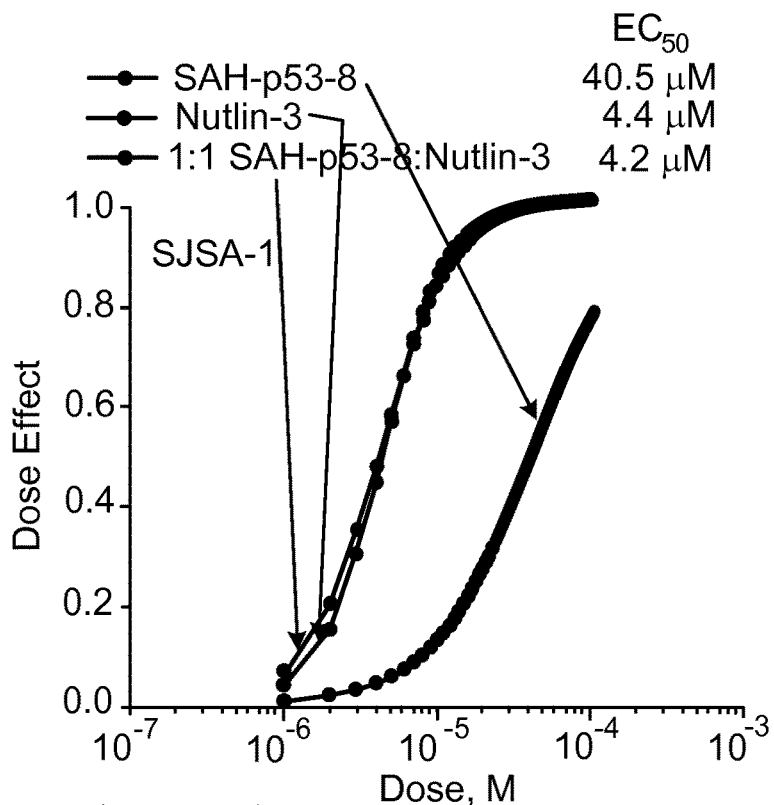
Figure 10D:
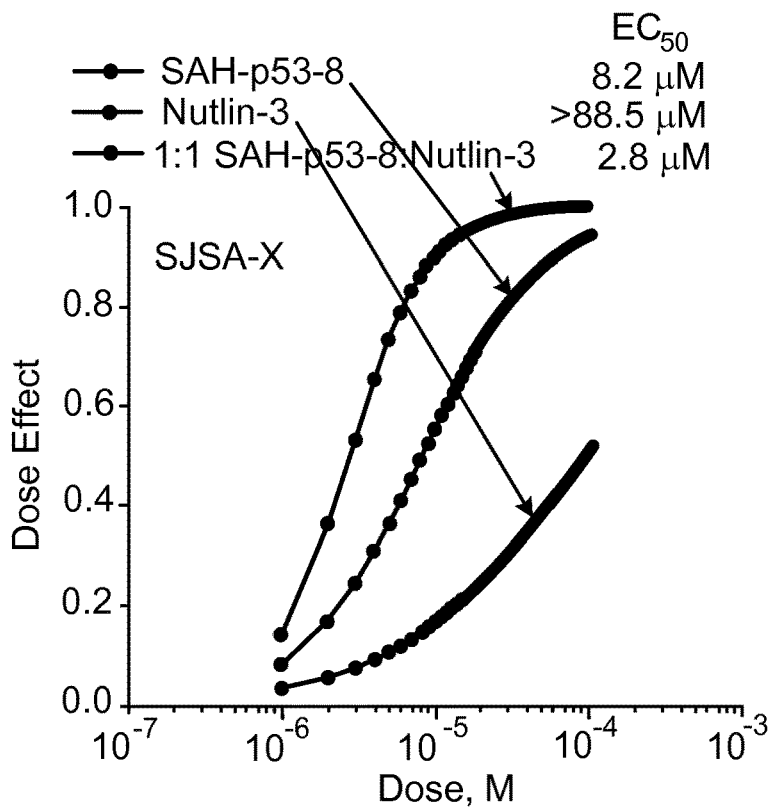
Figure 10E:
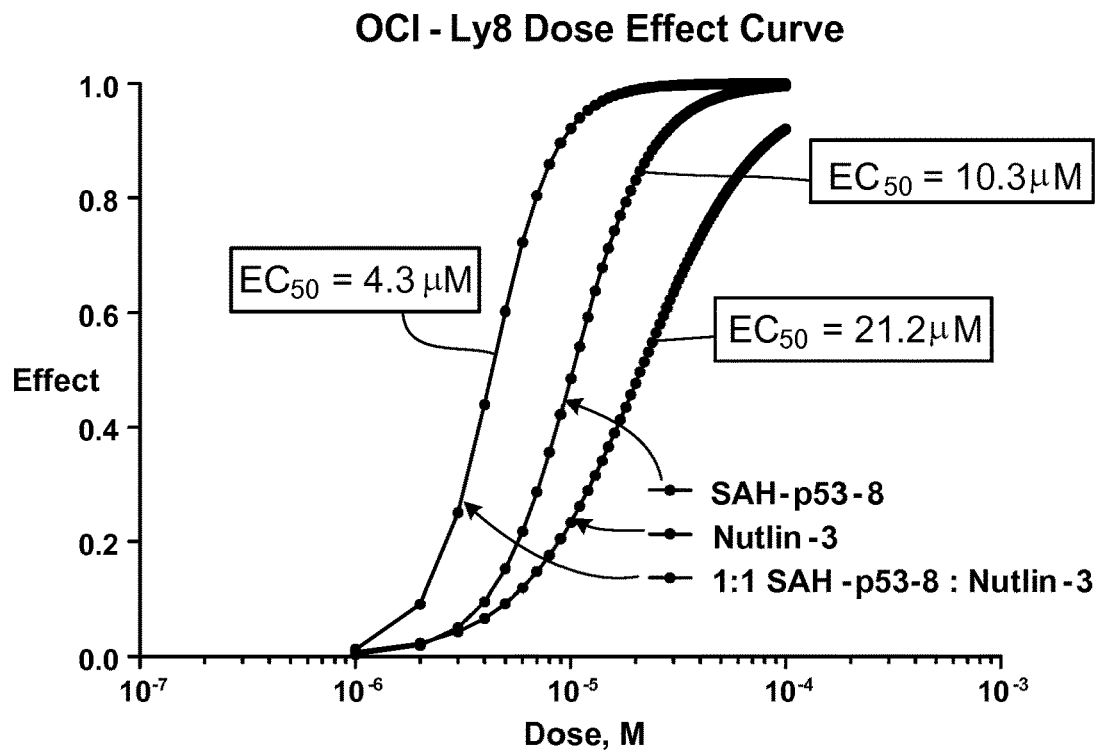
FIGS. 10E-10G are synergy graphs showing that SAH-p53-8 and Nutlin-3 exhibit synergistic anti-tumor activity in lymphoma and melanoma.
Figure 10F:
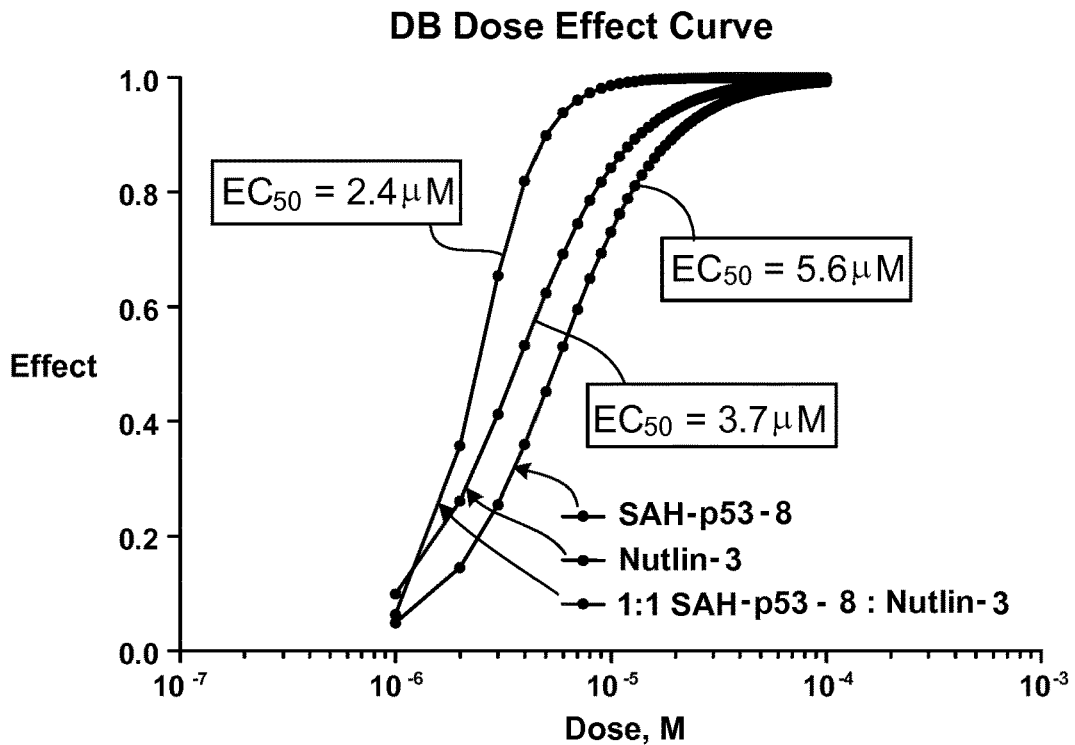
Figure 10G:
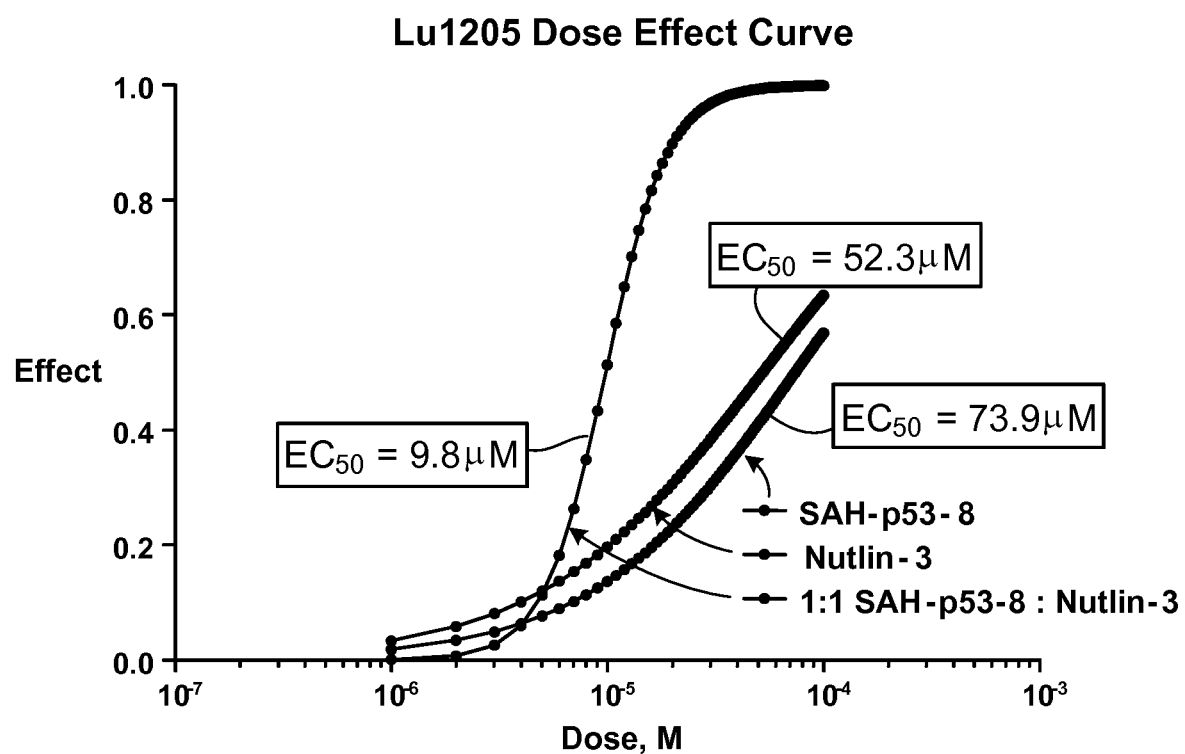
Figure 11A:
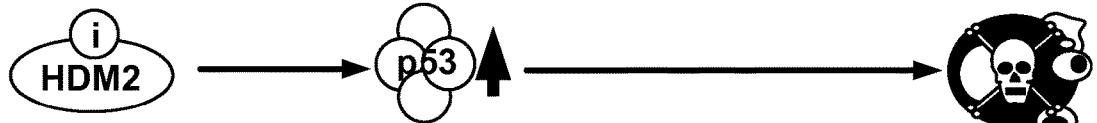
FIGS. 11A-11E are cartoons depicting treatment strategies for cancers identified to express p53 and HDM2 (A), p53 and HDMX (C), and p53, HDM2, and HDMX. (B) and (D) show treatment strategies that will fail.
Figure 11B:
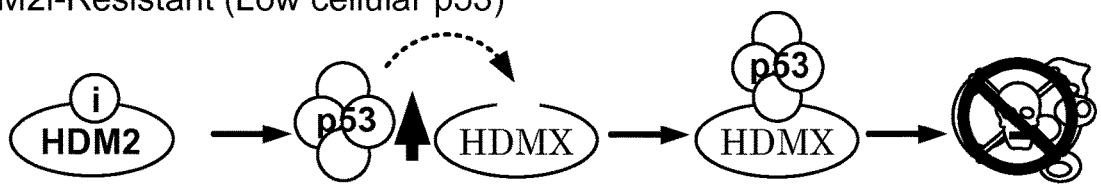
Figure 11C:
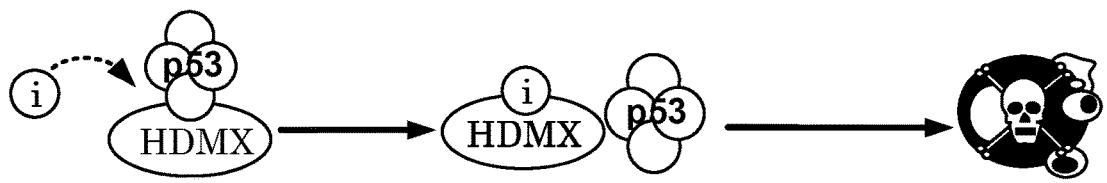
Figure 11D:
Figure 11E:
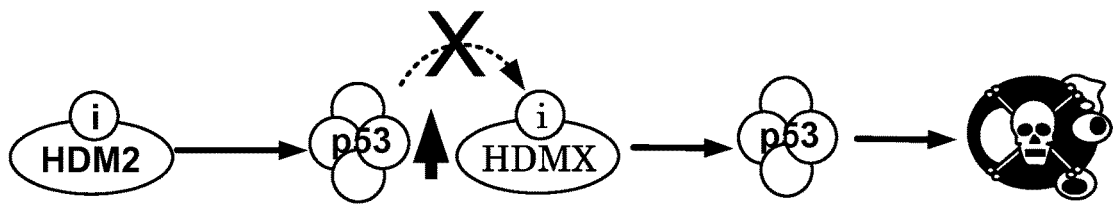

(2008)). As shown in FIG. 8, whereas Nutlin-3 can elevate p53 levels in MCF-7 cells, this increase in p53 coincides with the appearance of the inhibitory p53-HDMX complex, limiting Nutlin-3 cytotoxicity. However, as shown herein, by employing Nutlin-3, MCF-7 cells were pharmacologically transformed into a JEG-3-like state that manifests increased abundance of p53 in complex with HDMX (see FIGS. 9-10). More specifically, when combined, SAH-p53-8 and Nutlin-3 sensitize one another in a dose-responsive fashion (see FIGS. 9A-9B). As shown in FIG. 10A, synergy was confirmed using the CalcuSyn dose-effect analysis described by Chou (Pharmacol. Rev., 58:621-681 (2006)). The enhanced cytotoxicity observed upon co-treatment with SAH-p53-8 correlates with its blockade of p53-HDMX complex formation shown in FIG. 9A, consistent with the added capacity of SAH-p53-8 to target HDMX, a key source of resistance in MCF-7 cells. Further, as shown in FIG. 10B, Nutlin-3 does not synergize with SAH-p53-8 in JEG-3 cells, since endogenous p53 levels are already elevated. Conversely, when HDMX and p53 expression levels are low and the cellular phenotype is instead driven by HDM2 expression, as in SJSA-1 cells, co-treatment with SAH-p53-8 provides no added benefit to Nutlin-3 (see FIG. 10C). However, induction of HDMX expression in this isogenic cell line completely alters the synergy results rendering Nutlin-3 ineffective as a single agent, restoring susceptibility to SAH-p53-8, and re-establishing the synergistic benefit of combining Nutlin-3 with SAH-p53-8 treatment (see FIG. 10D). Further examples of synergistic anti-tumor activity upon combining SAH-p53-8 and Nutlin-3 are also shown for lymphoma and melanoma cancer cells (FIG. 10E-G).

These synergy analyses provide a mechanistic framework for determining how to optimally apply HDM2- and HDMX-targeting agents to reactivate the p53 pathway in cancer. Indeed, HDMX targeting is maximally effective when p53 levels are naturally or pharmacologically increased, as reflected by the presence of detectable p53-HDMX complexes, a potentially valuable biomarker for predicting therapeutic efficacy and monitoring the pharmacodynamic effects of treatment.

As shown herein, SAH-p53-8 binds to HDMX with high affinity in vitro and in vivo. As a result of this binding, SAH-p53-8 reduces p53-HDMX interaction, and thereby restores the p53 pathway, as evidenced, for example, by transcriptional upregulation of p53 targets and reduction of tumor cell viability both in vitro and in vivo (e.g., in animal models).

The data presented herein also makes apparent that therapeutic strategies for cancer treatment can be developed or improved by characterizing levels of certain proteins in tumor cells. For example, such methods include, e.g., confirming the expression of functional p53 (including wild type p53 expression and mutant p53 expression as long as the mutant p53 retains some function (e.g., p53 function sufficient to reduce viability of a cancer cell when the cell is exposed to one or more of the treatments disclosed herein)) and HDMX and/or HDM2 in a tumor cell (e.g., a tumor cell in a subject or a tumor cell obtained from a subject (e.g., a tumor cell in a biopsy sample). Such methods are described in more detail below.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a cancer expressing both HDM2 and HDMX in a human subject in need thereof, the method comprising:

administering to the human subject a HDMX modulating agent and a HDM2 modulating agent, wherein the HDMX modulating agent comprises an internally cross-linked polypeptide comprising at least nine contiguous amino acids of the amino acid sequence $Xaa_1$-$Xaa_2$-$Xaa_3$-$Xaa_4$-$Xaa_5$-$Phe_6$-$Xaa_7$-$Xaa_8$-$Xaa_9$-$Trp_{10}$-$Xaa_{11}$-$Xaa_{12}$-$Leu_{13}$-$Xaa_{14}$-$Xaa_{15}$-$Xaa_{16}$ (SEQ ID NO: 22), wherein the internally cross-linked polypeptide includes $Phe_6$, $Trp_{10}$, and $Leu_{13}$, and wherein:

$Xaa_1$ is Leu or Gln, or is missing;
$Xaa_2$ is Ser or is missing;
$Xaa_3$ is Gln or is missing;
$Xaa_4$ is Glu, Gln, or a hydrophobic amino acid;
$Xaa_5$ is Thr or Ala;
$Phe_6$ is Phe;
$Xaa_7$ is Ser or a stapling amino acid;
$Xaa_8$ is Asp or Asn;
$Xaa_9$ is Leu or a hydrophobic amino acid;
$Trp_{10}$ is Trp;
$Xaa_{11}$ is Lys, a positively charged amino acid, or a hydrophobic amino acid;
$Xaa_{12}$ is Leu, Lys, or Ala;
$Leu_{13}$ is Leu;
$Xaa_{14}$ is Pro or a stapling amino acid;
$Xaa_{15}$ is Glu, Gln, or Ala;
$Xaa_{16}$ is Asn or is missing;

wherein the side chains of at least two amino acids of the amino acid sequence separated by two, three, or six amino acids are replaced by an internal cross-link, and wherein the internally cross-linked polypeptide binds HDMX, is alpha helical, is neutral to positively charged, is cell permeable, and is not ubiquitinylated; and wherein the HDM2 modulating agent is Nutlin, a spiro-oxindole, a benzodiazepinedione, a terphenyl-based helical mimetic, a miniature protein, or a HDM2 targeting microRNA.

2. The method of claim 1, wherein the HDMX modulating agent is an internally cross-linked polypeptide comprising at least nine contiguous amino acids of the amino acid sequence $Xaa_1$-$Xaa_2$-$Xaa_3$-$Xaa_4$-$Xaa_5$-$Phe_6$-$Xaa_7$-$Xaa_8$-$Xaa_9$-$Trp_{10}$-$Xaa_{11}$-$Xaa_{12}$-$Leu_{13}$-$Xaa_{14}$-$Xaa_{15}$-$Xaa_{16}$ (SEQ ID NO: 22), wherein the internally cross-linked polypeptide includes $Phe_6$, $Trp_{10}$, and $Leu_{13}$, and wherein:

$Xaa_1$ is Gln;
$Xaa_2$ is Ser;
$Xaa_3$ is Gln;
$Xaa_4$ is Gln;
$Xaa_5$ is Thr;
$Phe_6$ is Phe;
$Xaa_7$ is a stapling amino acid;
$Xaa_8$ is Asn;
$Xaa_9$ is Leu;
$Trp_{10}$ is Trp;
$Xaa_{11}$ is Arg;
$Xaa_{12}$ is Leu;
$Leu_{13}$ is Leu;
$Xaa_{14}$ is a stapling amino acid;
$Xaa_{15}$ is Gln; and
$Xaa_{16}$ is Asn.

3. The method of claim 1, wherein the HDMX modulating agent comprises the amino acid sequence of SEQ ID NO: 10, except having 1, 2, or 3 amino acid substitutions.

4. The method of claim 1, further comprising administering the HDMX modulating agent and the HDM2 modulating agent with a pharmaceutically acceptable carrier, adjuvant, or vehicle.

5. The method of claim 1, further comprising administering the HDMX modulating agent and the HDM2 modulating agent with an additional therapeutic agent, in amounts effective for achieving a modulation of disease or disease symptoms.

6. The method of claim 1, wherein the HDMX modulating agent comprises the amino acid sequence of SEQ ID NO: 10.

7. The method of claim 1, wherein the HDMX modulating agent consists of the amino acid sequence of SEQ ID NO: 10.

8. A method for increasing p53 activity in a cell expressing both HDM2 and HDMX and in which p53 activity is not substantially increased upon treatment with a HDM2 modulating agent, the method comprising:

contacting the cell with a HDMX modulating agent and a HDM2 modulating agent, thereby increasing p53 activity in the cell, wherein the HDMX modulating agent is an internally cross-linked polypeptide comprising the amino acid sequence of SEQ ID NO: 10, except having 0-13 amino acid substitutions, wherein positions 6, 10, and 13 of SEQ ID NO: 10 are not substituted and positions 7 and 14 of SEQ ID NO: 10 are stapling amino acids, and wherein the internally cross-linked polypeptide binds HDMX, is alpha helical, is neutral to positively charged, is cell permeable, and is not ubiquitinylated, and wherein the HDM2 modulating agent is Nutlin, a spiro-oxindole, a benzodiazepinedione, a terphenyl-based helical mimetic, a miniature protein, or a HDM2 targeting microRNA.

9. A method of treating a cancer expressing functional p53 and also expressing both HDM2 and HDMX in a human subject in need thereof, the method comprising administering to the human subject a HDMX modulating agent and a HDM2 modulating agent, wherein the HDMX modulating agent is an internally cross-linked polypeptide comprising the amino acid sequence of SEQ ID NO: 10, except having 0-13 amino acid substitutions, wherein positions 6, 10, and 13 of SEQ ID NO: 10 are not substituted and positions 7 and 14 of SEQ ID NO: 10 are stapling amino acids, and wherein the internally cross-linked polypeptide binds HDMX, is alpha helical, is neutral to positively charged, is cell permeable, and is not ubiquitinylated, and wherein the HDM2 modulating agent is Nutlin, a spiro-oxindole, a benzodiazepinedione, a terphenyl-based helical mimetic, a miniature protein, or a HDM2 targeting microRNA.

10. The method of claim 9, further comprising administering to the human subject an additional therapeutic agent, in amounts effective for achieving a modulation of disease or disease symptoms.

11. The method of claim 1, wherein the HDM2 modulating agent is Nutlin 3.

12. The method of claim 1, wherein the HDM2 modulating agent is a spiro-oxindole, benzodiazepinedione, or a terphenyl-based helical mimetic.

13. The method of claim 11, wherein the Nutlin-3 is Nutlin-3a.

14. The method of claim 1, wherein the miniature protein is p53AD$_{15-31}$.

15. The method of claim 1, wherein the HDM2 modulating agent is a HDM2 targeting microRNA.

16. The method of claim 15, wherein the HDM2 targeting microRNA is miRNA miR-192.

17. The method of claim 8, wherein the HDM2 modulating agent is Nutlin 3.

18. The method of claim 9, wherein the internally cross-linked polypeptide comprises the amino acid sequence of SEQ ID NO: 10 except having 0-10 amino acid substitutions.

19. The method of claim 9, wherein the internally cross-linked polypeptide comprises the amino acid sequence of SEQ ID NO: 10 except having 0-6 amino acid substitutions.

20. The method of claim 9, wherein the internally cross-linked polypeptide comprises the amino acid sequence of SEQ ID NO: 10 except having 0-3 amino acid substitutions.

21. The method of claim 9, wherein the cancer is a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

22. The method of claim 9, wherein the HDM2 modulating agent is Nutlin 3.

23. The method of claim 9, wherein the HDM2 modulating agent is a spiro-oxindole, a benzodiazepinedione, or a terphenyl-based helical mimetic.

24. The method of claim 22, wherein the Nutlin-3 is Nutlin-3a.

25. The method of claim 9, wherein the miniature protein is p53AD$_{15-31}$.

26. The method of claim 9, wherein the HDM2 modulating agent is a HDM2 targeting microRNA.

27. The method of claim 26, wherein the HDM2 targeting microRNA is miRNA miR-192.

28. The method of claim 9, wherein the HDMX modulating agent comprises the amino acid sequence of SEQ ID NO: 10 and the HDM2 modulating agent is Nutlin 3.

29. The method of claim 28, wherein the Nutlin-3 is Nutlin-3a.

* * * * *

SEQUENCE LISTING

```
<160> NUMBER OF SEQ ID NOS: 33

<210> SEQ ID NO 1
<211> LENGTH: 393
<212> TYPE: PRT
<213> ORGANISM: Homo sapiens

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125
```

```
Ala Leu Asn Lys Met Phe Cys Gln Leu Ala Lys Thr Cys Pro Val Gln
        130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
        180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 2
<211> LENGTH: 16
<212> TYPE: PRT
<213> ORGANISM: Homo sapiens

<400> SEQUENCE: 2

Leu Ser Gln Glu Thr Phe Ser Asp Leu Trp Lys Leu Leu Pro Glu Asn
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any cross-linked amino acid in the R8
      orientation
<220> FEATURE:
<221> NAME/KEY: MOD_RES
<222> LOCATION: (16)..(16)
<223> OTHER INFORMATION: Any cross-linked amino acid in the S5
```

-continued orientation

<400> SEQUENCE: 3

Leu Ser Gln Glu Thr Phe Ser Asp Xaa Trp Lys Leu Leu Pro Glu Xaa
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any cross-linked amino acid in the R8
      orientation
<220> FEATURE:
<221> NAME/KEY: MOD_RES
<222> LOCATION: (12)..(12)
<223> OTHER INFORMATION: Any cross-linked amino acid in the S5
      orientation

<400> SEQUENCE: 4

Leu Ser Gln Glu Xaa Phe Ser Asp Leu Trp Lys Xaa Leu Pro Glu Asn
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any cross-linked amino acid in the R8
      orientation
<220> FEATURE:
<221> NAME/KEY: MOD_RES
<222> LOCATION: (11)..(11)
<223> OTHER INFORMATION: Any cross-linked amino acid in the S5
      orientation

<400> SEQUENCE: 5

Leu Ser Gln Xaa Thr Phe Ser Asp Leu Trp Xaa Leu Leu Pro Glu Asn
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cross-linked amino acid in the R8
      orientation
<220> FEATURE:
<221> NAME/KEY: MOD_RES
<222> LOCATION: (14)..(14)
<223> OTHER INFORMATION: Any cross-linked amino acid in the S5
      orientation

<400> SEQUENCE: 6

Leu Ser Gln Glu Thr Phe Xaa Asp Leu Trp Lys Leu Leu Xaa Glu Asn
1               5                   10                  15

```
<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cross-linked amino acid in the R8
      orientation
<220> FEATURE:
<221> NAME/KEY: MOD_RES
<222> LOCATION: (14)..(14)
<223> OTHER INFORMATION: Any cross-linked amino acid in the S5
      orientation

<400> SEQUENCE: 7

Leu Ser Gln Glu Thr Phe Xaa Asn Leu Trp Lys Leu Leu Xaa Gln Asn
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cross-linked amino acid in the R8
      orientation
<220> FEATURE:
<221> NAME/KEY: MOD_RES
<222> LOCATION: (14)..(14)
<223> OTHER INFORMATION: Any cross-linked amino acid in the S5
      orientation

<400> SEQUENCE: 8

Leu Ser Gln Gln Thr Phe Xaa Asn Leu Trp Arg Leu Leu Xaa Gln Asn
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cross-linked amino acid in the R8
      orientation
<220> FEATURE:
<221> NAME/KEY: MOD_RES
<222> LOCATION: (14)..(14)
<223> OTHER INFORMATION: Any cross-linked amino acid in the S5
      orientation

<400> SEQUENCE: 9

Gln Ser Gln Gln Thr Phe Xaa Asn Leu Trp Lys Leu Leu Xaa Gln Asn
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<221> NAME/KEY: MOD_RES
<222> LOCATION: (7)..(7)
<223> OTHER INFORMATION: Any cross-linked amino acid in the R8
      orientation
<220> FEATURE:
<221> NAME/KEY: MOD_RES
<222> LOCATION: (14)..(14)
<223> OTHER INFORMATION: Any cross-linked amino acid in the R8
      orientation

<400> SEQUENCE: 10

Gln Ser Gln Gln Thr Phe Xaa Asn Leu Trp Arg Leu Leu Xaa Gln Asn
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cross-linked amino acid in the R8
      orientation
<220> FEATURE:
<221> NAME/KEY: MOD_RES
<222> LOCATION: (11)..(11)
<223> OTHER INFORMATION: Any cross-linked amino acid in the R8
      orientation

<400> SEQUENCE: 11

Gln Ser Gln Gln Thr Phe Xaa Asn Leu Trp Xaa Leu Leu Pro Gln Asn
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any cross-linked amino acid in the R8
      orientation
<220> FEATURE:
<221> NAME/KEY: MOD_RES
<222> LOCATION: (7)..(7)
<223> OTHER INFORMATION: Any cross-linked amino acid in the R8
      orientation

<400> SEQUENCE: 12

Gln Ser Xaa Gln Thr Phe Xaa Asn Leu Trp Arg Leu Leu Pro Gln Asn
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cross-linked amino acid in the R8
      orientation
<220> FEATURE:

```
<221> NAME/KEY: MOD_RES
<222> LOCATION: (14)..(14)
<223> OTHER INFORMATION: Any cross-linked amino acid in the S5
      orientation

<400> SEQUENCE: 13

Gln Ser Gln Gln Thr Ala Xaa Asn Leu Trp Arg Leu Leu Xaa Gln Asn
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cross-linked amino acid in the R8
      orientation
<220> FEATURE:
<221> NAME/KEY: MOD_RES
<222> LOCATION: (14)..(14)
<223> OTHER INFORMATION: Any cross-linked amino acid in the S5
      orientation

<400> SEQUENCE: 14

Gln Ser Gln Gln Thr Phe Xaa Asn Leu Trp Arg Lys Lys Xaa Gln Asn
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cross-linked amino acid in the R8
      orientation
<220> FEATURE:
<221> NAME/KEY: MOD_RES
<222> LOCATION: (14)..(14)
<223> OTHER INFORMATION: Any cross-linked amino acid in the R8
      orientation

<400> SEQUENCE: 15

Leu Ser Gln Ala Ala Phe Xaa Ala Leu Trp Ala Leu Leu Xaa Ala Asn
1               5                   10                  15

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any cross-linked amino acid in the R8
      orientation
<220> FEATURE:
<221> NAME/KEY: MOD_RES
<222> LOCATION: (11)..(11)
<223> OTHER INFORMATION: Any cross-linked amino acid in the R8
      orientation

<400> SEQUENCE: 16
```

```
Gln Thr Phe Xaa Asn Leu Trp Arg Leu Leu Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any cross-linked amino acid in the R8
      orientation
<220> FEATURE:
<221> NAME/KEY: MOD_RES
<222> LOCATION: (11)..(11)
<223> OTHER INFORMATION: Any cross-linked amino acid in the R8
      orientation

<400> SEQUENCE: 17

Gln Thr Phe Xaa Asp Leu Trp Arg Leu Leu Xaa
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any cross-linked amino acid in the R8
      orientation
<220> FEATURE:
<221> NAME/KEY: MOD_RES
<222> LOCATION: (5)..(5)
<223> OTHER INFORMATION: Any cross-linked amino acid in the R8
      orientation

<400> SEQUENCE: 18

Xaa Thr Phe Ser Xaa Leu Trp Lys Leu Leu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any cross-linked amino acid in the R8
      orientation
<220> FEATURE:
<221> NAME/KEY: MOD_RES
<222> LOCATION: (8)..(8)
<223> OTHER INFORMATION: Any cross-linked amino acid in the R8
      orientation

<400> SEQUENCE: 19

Glu Thr Phe Xaa Asp Leu Trp Xaa Leu Leu
1               5                   10

<210> SEQ ID NO 20
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any cross-linked amino acid in the R8
      orientation
<220> FEATURE:
<221> NAME/KEY: MOD_RES
<222> LOCATION: (8)..(8)
<223> OTHER INFORMATION: Any cross-linked amino acid in the R8
      orientation

<400> SEQUENCE: 20

Gln Thr Phe Xaa Asn Leu Trp Xaa Leu Leu
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any cross-linked amino acid in the R8
      orientation
<220> FEATURE:
<221> NAME/KEY: MOD_RES
<222> LOCATION: (5)..(5)
<223> OTHER INFORMATION: Any cross-linked amino acid in the R8
      orientation

<400> SEQUENCE: 21

Xaa Ser Gln Glu Xaa Phe Ser Asn Leu Trp Lys Leu Leu
1               5                   10

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Gln or absent
<220> FEATURE:
<221> NAME/KEY: MOD_RES
<222> LOCATION: (2)..(3)
<223> OTHER INFORMATION: May or may not be present
<220> FEATURE:
<221> NAME/KEY: MOD_RES
<222> LOCATION: (4)..(4)
<223> OTHER INFORMATION: Glu, Gln or Ala
<220> FEATURE:
<221> NAME/KEY: MOD_RES
<222> LOCATION: (5)..(5)
<223> OTHER INFORMATION: Thr or Ala
<220> FEATURE:
<221> NAME/KEY: MOD_RES
<222> LOCATION: (6)..(6)
<223> OTHER INFORMATION: Phe or a conservative substitution thereof
<220> FEATURE:
<221> NAME/KEY: MOD_RES
<222> LOCATION: (8)..(8)
<223> OTHER INFORMATION: Asp, Asn or any amino acid other than Asp or
      Glu
<220> FEATURE:
<221> NAME/KEY: MOD_RES
```

```
<222> LOCATION: (10)..(10)
<223> OTHER INFORMATION: Trp or a conservative substitution thereof
<220> FEATURE:
<221> NAME/KEY: MOD_RES
<222> LOCATION: (11)..(11)
<223> OTHER INFORMATION: Lys or a positively charged amino acid
<220> FEATURE:
<221> NAME/KEY: MOD_RES
<222> LOCATION: (12)..(12)
<223> OTHER INFORMATION: Leu, Lys or Ala
<220> FEATURE:
<221> NAME/KEY: MOD_RES
<222> LOCATION: (13)..(13)
<223> OTHER INFORMATION: Leu or a conservative substitution thereof
<220> FEATURE:
<221> NAME/KEY: MOD_RES
<222> LOCATION: (14)..(14)
<223> OTHER INFORMATION: May or may not be present
<220> FEATURE:
<221> NAME/KEY: MOD_RES
<222> LOCATION: (15)..(15)
<223> OTHER INFORMATION: Glu, Gln or Ala or any amino acid other than
      Asp or Glu or absent
<220> FEATURE:
<221> NAME/KEY: MOD_RES
<222> LOCATION: (16)..(16)
<223> OTHER INFORMATION: May or may not be present
<220> FEATURE:
<221> NAME/KEY: misc_feature
<222> LOCATION: (1)..(16)
<223> OTHER INFORMATION: The side chains of at least two amino acids
      separated by two, three or six amino acids are replaced by an
      internal cross-link

<400> SEQUENCE: 22

Xaa Ser Gln Xaa Xaa Xaa Ser Xaa Leu Xaa Xaa Xaa Xaa Pro Xaa Asn
1               5                   10                  15

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: Glu, Gln or Ala
<220> FEATURE:
<221> NAME/KEY: MOD_RES
<222> LOCATION: (3)..(3)
<223> OTHER INFORMATION: Thr or Ala
<220> FEATURE:
<221> NAME/KEY: MOD_RES
<222> LOCATION: (4)..(4)
<223> OTHER INFORMATION: Phe or a conservative substitution thereof
<220> FEATURE:
<221> NAME/KEY: MOD_RES
<222> LOCATION: (6)..(6)
<223> OTHER INFORMATION: Asp, Asn or any amino acid other than Asp or
      Glu
<220> FEATURE:
<221> NAME/KEY: MOD_RES
<222> LOCATION: (8)..(8)
<223> OTHER INFORMATION: Trp or a conservative substitution thereof
<220> FEATURE:
<221> NAME/KEY: MOD_RES
<222> LOCATION: (9)..(9)
<223> OTHER INFORMATION: Lys or a positively charged amino acid
<220> FEATURE:
<221> NAME/KEY: MOD_RES
<222> LOCATION: (10)..(10)
```

```
<223> OTHER INFORMATION: Leu, Lys or Ala
<220> FEATURE:
<221> NAME/KEY: MOD_RES
<222> LOCATION: (11)..(11)
<223> OTHER INFORMATION: Leu or a conservative substitution thereof
<220> FEATURE:
<221> NAME/KEY: misc_feature
<222> LOCATION: (1)..(11)
<223> OTHER INFORMATION: The side chains of at least two amino acids
      separated by two, three or six amino acids are replaced by an
      internal cross-link

<400> SEQUENCE: 23

Gln Xaa Xaa Xaa Ser Xaa Leu Xaa Xaa Xaa Xaa
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Ser Phe Ala Glu Tyr Trp Asn Leu Leu Ser Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Thr Phe Glu His Tyr Trp Ala Gln Leu Thr Ser
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Ser Asn Leu Trp Arg Leu Leu Pro Gln Asn
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Ser Gln Gln Thr Phe Ser Asn Leu Trp Arg Leu Leu Pro Gln Asn
1               5                   10                  15

<210> SEQ ID NO 28
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 28

Xaa Ser Gln Xaa Thr Phe Xaa Xaa Leu Trp Xaa Leu Leu Xaa Xaa Asn
1               5                   10                  15

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 29

Gln Xaa Thr Phe Xaa Xaa Leu Trp Xaa Leu Leu
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid or not present wherein this
      region may encompass 0 to 5 residues
<220> FEATURE:
<221> NAME/KEY: MOD_RES
<222> LOCATION: (7)..(9)
<223> OTHER INFORMATION: Any amino acid or not present wherein this
      region may encompass 0 to 3 residues
<220> FEATURE:
<221> NAME/KEY: MOD_RES
<222> LOCATION: (11)..(12)
<223> OTHER INFORMATION: Any amino acid or not present wherein this
      region may encompass 0 to 2 residues
<220> FEATURE:
<221> NAME/KEY: MOD_RES
```

```
<222> LOCATION: (14)..(16)
<223> OTHER INFORMATION: Any amino acid or not present wherein this
      region may encompass 0 to 3 residues

<400> SEQUENCE: 30

Xaa Xaa Xaa Xaa Xaa Phe Xaa Xaa Xaa Trp Xaa Xaa Leu Xaa Xaa Xaa
 1               5                  10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: May or may not be present
<220> FEATURE:
<221> NAME/KEY: MOD_RES
<222> LOCATION: (6)..(6)
<223> OTHER INFORMATION: Phe or a conservative substitution thereof
<220> FEATURE:
<221> NAME/KEY: MOD_RES
<222> LOCATION: (10)..(10)
<223> OTHER INFORMATION: Trp or a conservative substitution thereof
<220> FEATURE:
<221> NAME/KEY: MOD_RES
<222> LOCATION: (13)..(13)
<223> OTHER INFORMATION: Leu or a conservative substitution thereof
<220> FEATURE:
<221> NAME/KEY: MOD_RES
<222> LOCATION: (14)..(16)
<223> OTHER INFORMATION: May or may not be present

<400> SEQUENCE: 31

Leu Ser Gln Glu Thr Xaa Ser Asp Leu Xaa Lys Leu Xaa Pro Glu Asn
 1               5                  10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cross-linked amino acid in the R8
      orientation
<220> FEATURE:
<221> NAME/KEY: MOD_RES
<222> LOCATION: (14)..(14)
<223> OTHER INFORMATION: Any cross-linked amino acid in the S5
      orientation

<400> SEQUENCE: 32

Gln Ser Gln Gln Thr Phe Xaa Asn Leu Trp Arg Leu Leu Xaa Gln Asn
 1               5                  10                  15

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 33

His His His His His His
1               5
```